United States Patent
Adams et al.

(10) Patent No.: US 9,896,680 B2
(45) Date of Patent: Feb. 20, 2018

(54) COMPOSITIONS AND METHODS COMPRISING ASPARTYL-TRNA SYNTHETASES HAVING NON-CANONICAL BIOLOGICAL ACTIVITIES

(71) Applicant: aTyr Pharma, Inc., San Diego, CA (US)

(72) Inventors: Ryan A. Adams, San Diego, CA (US); Fei Hong, San Diego, CA (US); Ji Zhao, San Diego, CA (US); Kristi Piehl, San Diego, CA (US); Eva R. Armour, San Diego, CA (US); Kenny D'Arigo, San Diego, CA (US); Leslie A. Greene, San Diego, CA (US); Eve Merriman, San Diego, CA (US)

(73) Assignee: aTyr Pharma, Inc., San Diego, CA (US)

( * ) Notice: Subject to any disclaimer, the term of this patent is extended or adjusted under 35 U.S.C. 154(b) by 0 days.

(21) Appl. No.: 14/703,627

(22) Filed: May 4, 2015

(65) Prior Publication Data

US 2016/0230163 A1  Aug. 11, 2016

Related U.S. Application Data

(63) Continuation of application No. 12/751,358, filed on Mar. 31, 2010, now abandoned.

(60) Provisional application No. 61/165,194, filed on Mar. 31, 2009.

(51) Int. Cl.

| | | |
|---|---|---|
| *A61K 38/00* | (2006.01) | |
| *C12N 9/00* | (2006.01) | |
| *C12Q 1/25* | (2006.01) | |
| *G01N 33/573* | (2006.01) | |
| *C07K 16/00* | (2006.01) | |

(52) U.S. Cl.
CPC .............. *C12N 9/93* (2013.01); *C07K 16/00* (2013.01); *C12Q 1/25* (2013.01); *G01N 33/573* (2013.01); *A61K 38/00* (2013.01); *C07K 2319/30* (2013.01); *C07K 2319/33* (2013.01); *C12Y 601/01012* (2013.01); *G01N 2500/00* (2013.01)

(58) Field of Classification Search
None
See application file for complete search history.

(56) References Cited

U.S. PATENT DOCUMENTS

| | | | |
|---|---|---|---|
| 6,225,060 | B1 | 5/2001 | Clark et al. |
| 6,255,090 | B1 | 7/2001 | Famodu et al. |
| 6,265,188 | B1 | 7/2001 | Brown et al. |
| 6,428,960 | B1 | 8/2002 | Clark et al. |
| 6,548,060 | B1 | 4/2003 | Kim |
| 6,903,189 | B2 | 6/2005 | Schimmel et al. |
| 7,067,126 | B2 | 6/2006 | Schimmel et al. |
| 7,196,068 | B2 | 3/2007 | Kim et al. |
| 7,273,844 | B2 | 9/2007 | Schimmel et al. |
| 7,413,885 | B2 | 8/2008 | Schimmel et al. |
| 7,459,529 | B2 | 12/2008 | Kim |
| 7,476,651 | B2 | 1/2009 | Schimmel et al. |
| 7,521,215 | B2 | 4/2009 | Schimmel et al. |
| 7,528,106 | B2 | 5/2009 | Friedlander et al. |
| 7,745,391 | B2 | 6/2010 | Mintz et al. |
| 7,901,917 | B2 | 3/2011 | Schimmel et al. |
| 7,902,165 | B2 | 3/2011 | Kim |
| 8,003,780 | B2 | 8/2011 | Kim et al. |
| 8,017,593 | B2 | 9/2011 | Schimmel et al. |
| 8,026,088 | B2 | 9/2011 | Yang |
| 8,101,566 | B2 | 1/2012 | Schimmel et al. |
| 8,148,125 | B2 | 4/2012 | Schimmel et al. |
| 2002/0182666 | A1 | 12/2002 | Schimmel et al. |
| 2003/0017564 | A1 | 1/2003 | Schimmel et al. |
| 2003/0082575 | A1 | 5/2003 | Schultz et al. |
| 2003/0158400 | A1 | 8/2003 | Tang et al. |
| 2003/0165921 | A1 | 9/2003 | Tang et al. |
| 2003/0166241 | A1 | 9/2003 | Famodu et al. |
| 2003/0215827 | A1 | 11/2003 | Yue et al. |
| 2004/0018505 | A1 | 1/2004 | Lee et al. |
| 2004/0048290 | A1 | 3/2004 | Lee et al. |
| 2004/0101879 | A1 | 5/2004 | Seidel-Dugan et al. |
| 2004/0152079 | A1 | 8/2004 | Schimmel et al. |
| 2005/0196754 | A1 | 9/2005 | Drmanac et al. |
| 2006/0024288 | A1 | 2/2006 | Glidden |
| 2006/0046250 | A1 | 3/2006 | Kim |
| 2006/0078553 | A1 | 4/2006 | Glidden |
| 2007/0048322 | A1 | 3/2007 | Schimmel et al. |
| 2007/0061916 | A1 | 3/2007 | Kovalic et al. |
| 2007/0111238 | A1 | 5/2007 | Jamieson et al. |
| 2007/0224201 | A1 | 9/2007 | Wu et al. |
| 2009/0221794 | A1 | 9/2009 | Kim et al. |
| 2009/0227662 | A1 | 9/2009 | Schimmel et al. |

(Continued)

FOREIGN PATENT DOCUMENTS

| | | |
|---|---|---|
| CN | 1341725 | 3/2002 |
| CN | 1341727 | 3/2002 |

(Continued)

OTHER PUBLICATIONS

Veronese and Harris, Advanced Drug Delivery Reviews 54: 453-456, 2002.*
International Preliminary Report on Patentability for International Application No. PCT/US2009/048915, dated Jan. 5, 2011.
International Search Report and Written Opinion for International Application No. PCT/US2009/048915, dated Nov. 2, 2009.
Office Action for U.S. Appl. No. 12/482,151, dated Oct. 11, 2011, 43 pages.

(Continued)

*Primary Examiner* — Richard G Hutson
(74) *Attorney, Agent, or Firm* — Cooley LLP

(57) ABSTRACT

Isolated aspartyl-tRNA synthetase polypeptides and polynucleotides having non-canonical biological activities are provided, as well as compositions and methods related thereto.

9 Claims, 20 Drawing Sheets

(56) References Cited

U.S. PATENT DOCUMENTS

| | | |
|---|---|---|
| 2009/0285792 A1 | 11/2009 | Friedlander et al. |
| 2010/0003230 A1 | 1/2010 | Glidden |
| 2010/0028352 A1 | 2/2010 | Greene et al. |
| 2010/0048413 A1 | 2/2010 | Arcus et al. |
| 2010/0092434 A1 | 4/2010 | Belani et al. |
| 2010/0138941 A1 | 6/2010 | Kim et al. |
| 2010/0297149 A1 | 11/2010 | Zhou et al. |
| 2010/0310576 A1 | 12/2010 | Adams et al. |
| 2011/0110917 A1 | 5/2011 | Schimmel et al. |
| 2011/0117572 A1 | 5/2011 | Kim et al. |
| 2011/0136119 A1 | 6/2011 | Kim et al. |
| 2011/0150885 A1 | 6/2011 | Watkins et al. |
| 2011/0189195 A1 | 8/2011 | Kim et al. |
| 2011/0250701 A1 | 10/2011 | Kim et al. |
| 2011/0256119 A1 | 10/2011 | Kim et al. |
| 2012/0004185 A1 | 1/2012 | Greene |
| 2012/0015383 A1 | 1/2012 | Park et al. |
| 2012/0058133 A1 | 3/2012 | Whitman et al. |
| 2012/0064082 A1 | 3/2012 | Watkins et al. |
| 2013/0108630 A1 | 5/2013 | Watkins et al. |
| 2013/0224174 A1 | 8/2013 | Greene et al. |
| 2013/0273045 A1 | 10/2013 | Watkins et al. |
| 2013/0280230 A1 | 10/2013 | Greene et al. |

FOREIGN PATENT DOCUMENTS

| | | |
|---|---|---|
| CN | 1352242 | 6/2002 |
| CN | 1352252 | 6/2002 |
| EP | 0785265 | 7/1997 |
| EP | 0893494 | 1/1999 |
| EP | 0893496 | 1/1999 |
| EP | 0897004 | 2/1999 |
| EP | 1275720 | 1/2003 |
| EP | 1300468 | 4/2003 |
| EP | 1377305 | 1/2009 |
| EP | 1776138 | 10/2009 |
| EP | 1274834 | 7/2010 |
| JP | 2008-508349 | 3/2008 |
| WO | WO 1997/026351 | 7/1997 |
| WO | WO 1997/039017 | 10/1997 |
| WO | WO 1999/045130 | 9/1999 |
| WO | WO 2001/074841 | 10/2001 |
| WO | WO 2001/075067 | 10/2001 |
| WO | WO 2001/075078 | 10/2001 |
| WO | WO 2001/090330 | 11/2001 |
| WO | WO 2001/094568 | 12/2001 |
| WO | WO 2002/055663 | 7/2002 |
| WO | WO 2002/059323 | 8/2002 |
| WO | WO 2002/067970 | 9/2002 |
| WO | WO 2003/009813 | 2/2003 |
| WO | WO 2003/080648 | 10/2003 |
| WO | WO 2003/094862 | 11/2003 |
| WO | WO 2004/030615 | 4/2004 |
| WO | WO 2005/019258 | 3/2005 |
| WO | WO 2005/102395 | 11/2005 |
| WO | WO 2005/117954 | 12/2005 |
| WO | WO 2006/016217 | 2/2006 |
| WO | WO 2006/057500 | 6/2006 |
| WO | WO 2007/064941 | 6/2007 |
| WO | WO 2007/139397 | 12/2007 |
| WO | WO 2008/007818 | 1/2008 |
| WO | WO 2008/016356 | 2/2008 |
| WO | WO 2008/021290 | 2/2008 |
| WO | WO 2008/133359 | 11/2008 |
| WO | WO 2009/114623 | 9/2009 |
| WO | WO 2009/152247 | 12/2009 |
| WO | WO 2009/158649 | 12/2009 |
| WO | WO 2010/021415 | 2/2010 |
| WO | WO 2010/041892 | 4/2010 |
| WO | WO 2010/041913 | 4/2010 |
| WO | WO 2010/090471 | 8/2010 |
| WO | WO 2010/096170 | 8/2010 |
| WO | WO 2010/099477 | 9/2010 |
| WO | WO 2010/107825 | 9/2010 |
| WO | WO 2010/120509 | 10/2010 |
| WO | WO 2011/072265 | 6/2011 |
| WO | WO 2011/072266 | 6/2011 |
| WO | WO 2011/097031 | 8/2011 |
| WO | WO 2012/009289 | 1/2012 |

OTHER PUBLICATIONS

Office Action for U.S. Appl. No. 12/482,151, dated Mar. 18, 2011, 11 pages.
International Preliminary Report on Patentability for International Application No. PCT/US2009/046910, dated Dec. 13, 2010.
International Search Report and Written Opinion for International Application No. PCT/US2009/046910, dated Mar. 4, 2010.
Office Action for European Patent Application No. 06838844.6, dated Apr. 9, 2009.
Office Action for U.S. Appl. No. 12/085,884, dated Jan. 20, 2011.
International Preliminary Report on Patentability for International Application No. PCT/US2006/046106, dated Jun. 4, 2008.
International Search Report and Written Opinion for International Application No. PCT/US2006/046106, dated Aug. 9, 2007.
Supplementary European Search Report for European Application No. 10746935.5, dated Oct. 26, 2012.
Office Action for U.S. Appl. No. 13/203,831, dated Oct. 7, 2013, 20 pages.
International Preliminary Report on Patentability for International Application No. PCT/US2010/025642, dated Aug. 30, 2011.
International Search Report and Written Opinion for International Application No. PCT/US2010/025642, dated Oct. 29, 2010.
Supplementary European Search Report for European Application No. 10764856.0, dated Sep. 5, 2012.
Office Action for U.S. Appl. No. 12/751,358, dated Dec. 2, 2014.
Office Action for U.S. Appl. No. 12/751,358, dated Jun. 11, 2014.
Office Action for U.S. Appl. No. 12/751,358, dated Oct. 3, 2011.
Office Action for U.S. Appl. No. 12/751,358, dated Mar. 3, 2011.
International Preliminary Report on Patentability for International Application No. PCT/US2010/029377, dated Oct. 4, 2011.
International Search Report and Written Opinion for International Application No. PCT/US2010/029377, dated Jan. 26, 2011.
International Preliminary Report on Patentability for International Application No. PCT/US2010/027525, dated Sep. 20, 2011.
International Search Report and Written Opinion for International Application No. PCT/US2010/027525, dated Jan. 10, 2011.
International Search Report and Written Opinion for International Application No. PCT/US2010/059964, dated Aug. 25, 2011.
International Preliminary Report on Patentability for International Application No. PCT/US2010/059964, dated Jun. 12, 2012.
International Preliminary Report on Patentability for International Application No. PCT/US2010/059963, dated Jun. 12, 2012, 18 pages.
International Search Report and Written Opinion for International Application No. PCT/US2010/059963, dated May 12, 2011.
International Search Report and Written Opinion for International Application No. PCT/US2011/000210, dated Aug. 12, 2011.
Notice of Allowance for U.S. Appl. No. 13/809,750, dated Oct. 17, 2014, 10 pages.
International Search Report and Written Opinion for International Application No. PCT/US2011/043596, dated Feb. 29, 2012.
International Preliminary Report on Patentability for International Application No. PCT/US2011/043596, dated Jan. 15, 2013.
International Search Report and Written Opinion for International Application No. PCT/US2012/068282, dated Apr. 1, 2013.
International Search Report and Written Opinion for International Application No. PCT/US2012/068296, dated Apr. 19, 2013.
Adams, M. D. et al., "The genome sequence of drosophila melanogaster," Science, 287(5961):2185-2195 (2000).
Aderem, A. et al., "Toll-like receptors in the induction of the innate immune response," Nature, 406:782-787 (2000).
Amaar, Y. G. et al., "Cloning and characterization of the C.elegans histidyl-tRNA synthetase gene," Nucleic Acids Research, 21(18):4344-4347 (1993).

(56) References Cited

OTHER PUBLICATIONS

Antonellis, A. et al., "The Role of Aminoacyl-tRNA Synthetases in Genetic Diseases," Annual Review of Genomics and Human Genetics, 9(1):87-107 (2008).
Brightbill, H. D. et al., "Toll-like receptors: molecular mechanisms of the mammalian immune response," Immunology, 101:1-10 (2000).
Broun, P. et al., "Catalytic plasticity of fatty acid modification enzymes underlying chemical diversity of plant lipids," Science, 282:1315-1317 (1998).
Brown, M. V. et al., "Mammalian aminoacyl-tRNA synthetases: Cell signaling functions of the protein translation machinery," Vascular Pharmacology, 52(1-2):21-26 (2010).
Car, B. D. et al., "Interferon y Receptor Deficient Mice Are Resistant to Endotoxic Shock," J. Exp. Med., 179:1437-1444 (1994).
Cheong et al., "Structure of the N-terminal extension of human aspartyl-tRNA synthetase: implications for its biological function," The International Journal of Biochemistry & Cell Biology, 35:1548-1557 (2003).
Chica, R. A. et al., "Semi-rational approaches to engineering enzyme activity: combining the benefits of directed evolution and rational design," Curr. Opin. Biotechnol., 16:378-384 (2005).
Delgado, C. et al., "The uses and properties of PEG-linked proteins," Critical Reviews in Therapeutic Drug Carrier Systems, 9(3,4):249-304 (1992).
Devos, D. et al., "Practical limits of function prediction," Proteins: Structure, Function, and Genetics, 41:98-107 (2000).
Eriani, G. et al., "Cytoplasmic aspartyl-tRNA synthetase from *Saccharomyces cerevisiae*. Study of its functional organisation by deletion analysis," European Journal of Biochemistry, 200(2):337-343 (1991).
Escalante, C., et al., "Expression of human aspartyl-tRNA synthetase in COS cells," Molecular and Cellular Biochemistry, 140(1):55-63 (1994).
Escalante, C. et al., "Expression of Human Aspartyl-tRNA Synthetase in *Escherichia coli*: Functional Analysis of the N-Terminal Putative Amphiphilic Helix," The Journal of Biological Chemistry, 268(8):6014-6023 (1993).
Ewalt, K. L. et al., "Activation of Angiogenic Signaling Pathways by Two Human tRNA Synthetases," Biochemistry, 41(45):13344-13349 (2002).
Frommhold, D. et al., "Sialyltransferase ST3Gal-IV controls CXCR2-mediated firm leukocyte arrest during inflammation," Journal of Experimental Medicine, 205(6):1435-1446 (2008).
GenBank Accession No. AA131122, Nov. 27, 1996.
GenBank Accession No. AA281081, Apr. 2, 1997.
GenBank Accession No. AA355758, Apr. 21, 1997.
GenBank Accession No. A1985978, Aug. 31, 1999.
GenBank Accession No. AV685924, Sep. 25, 2000.
GenBank Accession No. AW070887, Oct. 13, 1999.
GenBank Accession No. BE695954, Sep. 11, 2000.
GenBank Accession No. BF437672, Nov. 29, 2000.
GenBank Accession No. BF526055, Dec. 4, 2000.
GenBank Accession No. BG700836, May 7, 2001.
GenBank Accession No. BI559642, Sep. 4, 2001.
GenBank Accession No. BI599431, Sep. 5, 2001.
GenBank Accession No. BM827507, Mar. 6, 2002.
GenBank Accession No. BQ002750, Mar. 26, 2002.
GenBank Accession No. BU599828, Sep. 19, 2002.
GenBank Accession No. CA865450, Dec. 20, 2002.
GenBank Accession No. CA865692, Dec. 20, 2002.
GenBank Accession No. CD694017, Jun. 25, 2003.
GenBank Accession No. CR749809, Oct. 7, 2008.
GenBank Accession No. J05032, published Apr. 27, 1993.
GenBank Accession No. Q7QD89, Anopheles gambiae Sequence Committee, submitted Apr. 2002, [Retrieved from the Internet Apr. 24, 2007], <URL:http://www.ncbi.nlm.nih.gov/entrez/viewer.fcgi?db=protein&val=74803944>.
GenBank Accession No. Q9VV60, published May 1, 2000.

Goldgur, Y. et al., "The crystal structure of phenylalanyl-tRNA synthetase from Thermus thermophilus complexed with cognate tRNA," Structure, 5(1):59-68 (1997).
Greenberg, Y. et al., "The novel fragment of tyrosyl tRNA synthetase, mini-TyrRS, is secreted to induce an angiogenic response in endothelial cells," FASEB Journal, 22(5):1597-1605 (2008).
Guijarro, J. I. et al., "Structure and Dynamics of the Anticodon Arm Binding Domain of Bacillus stearothermophilus Tyrosyl-tRNA Synthetase," Structure, 10(3):311-317 (2002).
Guo, M. et al., "Functional expansion of human tRNA synthetases achieved by structural inventions," FEBS Letters, 584(2):434-442 (2010).
Guo, M. et al., "New functions of aminoacyl-tRNA synthetases beyond translation," Nature Reviews Molecular Cell Biology, 11:668-674 (2010).
Hausmann, C. D. et al., "Aminoacyl-tRNA synthetase complexes: molecular multitasking revealed," FEMS Microbiol. Rev., 32(4):705-721 (2008).
Hou, Y-M. et al., "Sequence determination and modeling of structural motifs for the smallest monomeric aminoacyl-tRNA synthetase," Proc. Nat. Acad. Sci., 88(3):976-980 (1991).
Ivakhno, S. S. et al., "Cytokine-Like Activities of Some Aminoacyl-tRNA Synthetases and Auxiliary p43 Cofactor of Aminoacylation Reaction and Their Role in Oncogenesis," Exp. Oncol., 26(4):250-255 (2004).
Jacobo-Molina, A. et al., "cDNA Sequence, Predicted Primary Structure, and Evolving Amphiphilic Helix of Human Aspartyl-tRNA Synthetase," Journal of Biological Chemistry, 264(28):16608-16612 (1989).
Jura, M. et al., "Comprehensive Insight into human aminoacyl-tRNA synthetases as autoantigens in idiopathic inflammatory myopathies," Critical Reviews in Immunology, 27(6):559-572 (2007).
Kapoor, M. et al., "Mutational separation of aminoacylation and cytokine activities of human tyrosyl-tRNA synthetase," Chemistry & Biology, 16(5):531-539 (2009).
Kimchi-Sarfaty, C. et al., "A 'Silent' polymorphism in the MDR1 gene changes substrate specificty," Science, 315:525-528 (2007).
Kise, Y. et al., "A short peptide insertion crucial for angiostatic activity of human tryptophanyl-tRNA synthetase," Nature Structural & Molecular Biology, 11(2):149-156 (2004).
Kochendoerfer, G. G., "Site-specific polymer modification of therapeutic proteins," Current Opinion in Chemical Biology, 9:555-560 (2005).
Kovaleski, B. J. et al.,"In vitro characterization of the interaction between HIV-1 Gag and human lysyl-tRNA synthetase," J. Bio. Chem., 281(28):19449-19456 (2006).
Levine, S. M. et al., "Anti-aminoacyl tRNA synthetase immune responses: insights into the pathogenesis of the idiopathic inflammatory myopathies," Current Opinion in Rheumatology, 15(6):708-713 (2003).
Link, A. J. et al., "Discovery of aminoacyl-tRNA synthetase activity through cell-surface display of noncanonical amino acids, " Proc. Nat. Acad. Sci., 103(27):10180-10185 (2006).
Lorber, Bernard, et al., "Properties of N-terminal truncated yeast aspartyl-tRNA synthetase and structural characteristics of the cleaved domain," Eur. J. Biochem. 174, pp. 155-161 (1988).
Mirande, M. et al., "Engineering mammalian aspartyl-tRNA synthetase to probe structural features mediating its association with the multisynthetase complex," Eur. J. Biochem., 203(3):459-466 (1992).
Nackley, A. G. et al., "Human Caechol-O-Methytransferase haplotypes modulate protein expression by altering mRNA secondary structure," Science, 314:1930-1933 (2006).
NCBI Accession No. NP001340, Feb. 27, 2011.
Ngo, J. T. et al., "Computational complexity, protein structure prediction, and the Levinthal paradox," In the Protein Folding Problem and Tertiary Structure Prediction, Merz et al. (ed.), Birkhauser, Boston, MA, pp. 433 and 492-495 (1994).

(56) References Cited

OTHER PUBLICATIONS

Nichols, R. C. et al., "Human isoleucyl-tRNA synthetase: sequence of the cDNA, alternative mRNA splicing, and the characteristics of an unusually long C-terminal extension," Gene, 155(2):299-304 (1995).
Park, S. G., et al., "Aminoacyl tRNA synthetases and their connections to disease," PNAS, 105(32):11043-11049 (2008).
Park, S. G. et al., "Dose-dependent biphasic activity of tRNA synthetase-associating factor, p43, in angiogenesis," The Journal of Biological Chemistry, 277(47):45243-45248 (2002).
Park, S. G. et al., "Human lysyl-tRNA syntetase is secreted to trigger proinflammatory response," PNAS, 102(18):6356-6361 (2005).
Park, S. G. et al., "Is there an answer? Do aminoacyl-tRNA synthetases have biological functions other than in protein biosynthesis?" IUBMB Life, 58(9):556-558 (2006).
Quesniaux, V. F.J. et al., "Hematopoiesis, including lymphocyte developmet and maturation," Principles of Immunopharmacology, pp. 3-17 (2005).
Reed, V. S. et al., "Characterization of a Novel N-terminal Peptide in Human Aspartyl-tRNA Synthetase," Journal of Biological Chemistry, 269(52):32937-32941 (1994).
Rho, S. B. et al., "Genetic dissection of protein-protein interactions in multi-tRNA synthetase complex," Proc. Natl. Acad. Sci. USA, 96:4488-4493 (1999).
Richardson, R. M. et al., "Role of the cytoplasmic tails of CXCR1 and CXCR2 in mediating leukocyte migration, activation, and regulation," Journal of Immunology, 170(6):2904-2911 (2003).
Sato et al., "Synergy and Cross-Tolerance Between Toll-Like Receptor (TLR) 2- and TLR4-Mediated Signaling Pathways," The Journal of Immunology, 165:7096-7101 (2000).
Sauna, Z. E. et al., "Silent polymorhisms speak: How they affect pharmacogenomics and the treatment of cancer," Cancer Res., 67(20):9609-9612 (2007).
Seburn, K. L. et al., "An active dominant mutation of glycyl-tRNA synthetase causes neuropathy in a Charcot-Marie-Tooth 2D mouse model," Neuron, 51(6):715-726 (2006).
Sen, S. et al., "Developments in directed evolution for improving enzyme functions," Appl. Biochem. Biotechnol., 143:212-223 (2007).
Smith, D. F. et al., "Leukocyte phosphoinositide-3 kinase γ is required for chemokine-induced, sustained adhesion under flow in vivo," Journal of Leukocyte Biology, 80(6):1491-1499 (2006).
Traves, S. L. et al., "Specific CXC but not CC chemokines cause elevated monocyte migration in COPD: a role for $CXCR_2$," Journal of Leukocyte Biology, 76(2):441-450 (2004).
Veronese, F. M. et al., "Preface: Introduction and overview of peptide and protein pegylation," Advanced Drug Delivery Reviews, 54:453-456 (2002).
Wakasugi, K. et al., "Two distinct cytokines released from a human aminoacyl-tRNA synthetase," Science, 284:147-151 (1999).
Wakasugi, K. et al., "A human aminoacyl-tRNA synthetase as a regulator of angiogenesis," PNAS USA, 99(1):173-177 (2002).
Wakasugi, K. et al., "Induction of angiogenesis by a frament of human tyrosyl-tRNA synthetase," The Journal of Biological Chemistry, 277(23):20124-20126 (2002).
Wan et al., "Epitope Map for a Growth Hormone Receptor Agonist Monoclonal Antibody, MAb 263," Molecular Endocrinology, 17(11):2240-2250 (2003).
Whisstock, J. C. et al., "Prediction of protein function from protein sequence," Q. Rev. Biophysics., 36(3):307-340 (2003).
Wishart, M. J. et al., "A single mutation converts a novel phosphotyrosine binding domain into a dual-specificity phosphatase," J. Biol. Chem., 270(45):26782-26785 (1995).
Witkowski, A. et al., "Conversion of β-ketoacyl synthase to a Malonyl Decarboxylase by replacement of the active cysteine with glutamine," Biochemistry, 38:11643-11650 (1999).
Xie, W. et al., "Long-range structural effects of a Charcot-Marie-Tooth disease-causing mutation in human glycyl-tRNA synthetase," PNAS, 104(24):9976-9981 (2007).
Yang, X-L et al., "Crystal structure of a human aminoacyl-tRNA synthetase cytokine," PNAS, 99(24):15369-15374 (2002).
Yang, X-L et al., "Relationship of two human tRNA synthetases used in cell signaling," Trends in Biochemical Sciences, 29(5):250-256 (2004).
Yang, X-L et al., "Gain-of-Function Mutational Activation of Human tRNA Synthetase Procytokine," Chemistry & Biology, 14(12):1323-1333 (2007).
Yu, Y. et al., "Crystal structure of human tryptophanyl-tRNA synthetase catalytic fragment," The Journal of Biological Chemistry, 279(9):8378-8388 (2004).
Zalipsky, S. et al., "Use of functionalized poly(ethylene glycol)s for modification of polypeptides," Polyethylene glycol chemistry: Biotechnical and Biomedical Applications, pp. 347-370, Plenum Press, New York (1992).
Zhou, Q. et al., "Orthogonal use of a human tRNA synthetase active site to achieve multifunctionality," Nature Structural & Molecular Biology, 17(1):57-62 (2010).
Zwijnenburg, P. J. G. et al., B-1426, "Tyrosyl tRNA synthetase is a chemotactic factor in cerebrospinal fluid from patients with bacterial meningitis," Abstracts of the 42nd Interscience Conference on Antimicrobial Agents and Chemotherapy, San Diego, California, Sep. 27-30, 2002, Session 156(B), p. 55.

\* cited by examiner

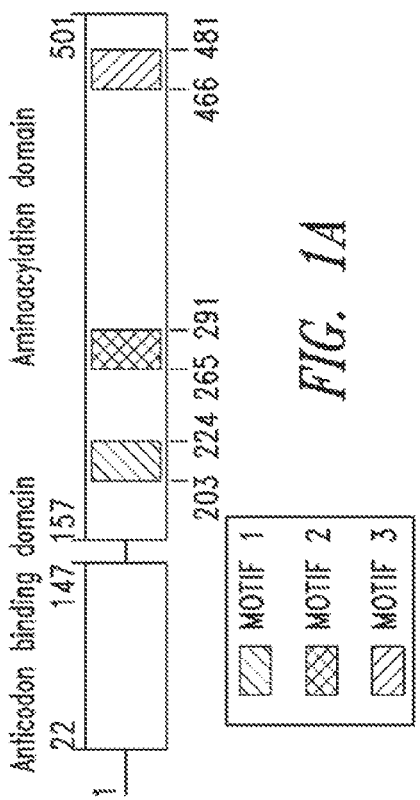
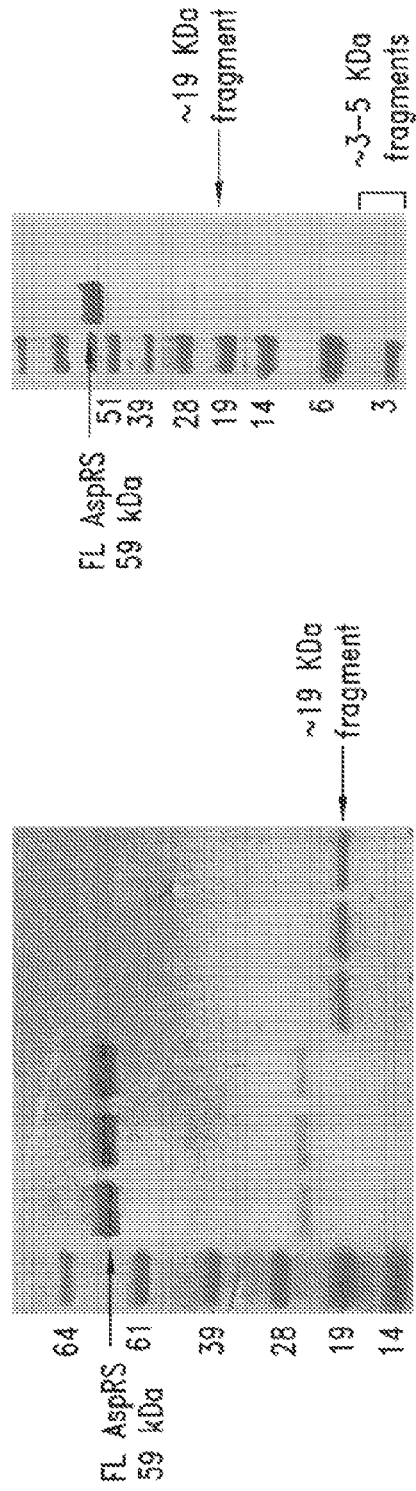
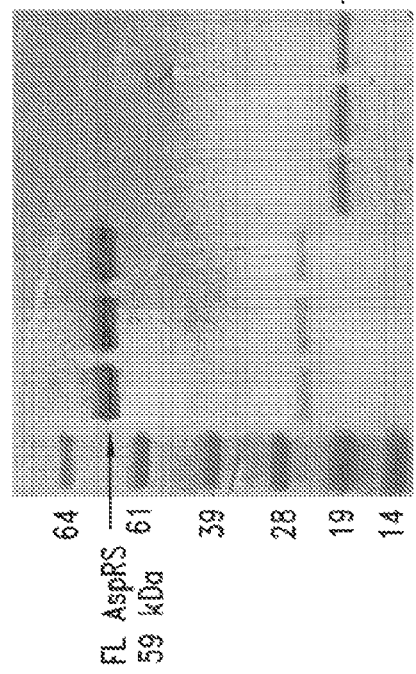
FIG. 1A
FIG. 1B
FIG. 1C
FIG. 1D

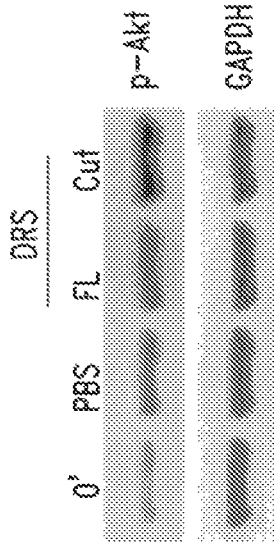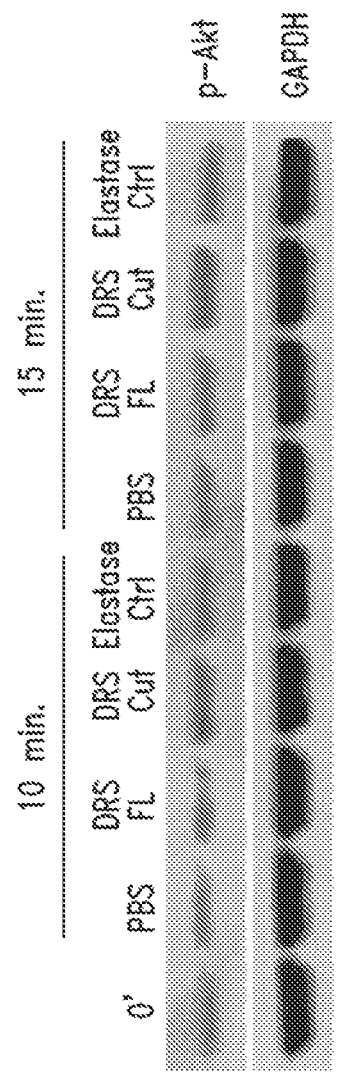
FIG. 2A
FIG. 2B

SEQUENCE LISTING

```
<160> NUMBER OF SEQ ID NOS: 23

<210> SEQ ID NO 1
<211> LENGTH: 501
<212> TYPE: PRT
<213> ORGANISM: Homo sapiens

<400> SEQUENCE: 1

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45
```

-continued

Arg Asp Leu Thr Ile Gln Lys Ala Asp Glu Val Val Trp Val Arg Ala
    50              55              60

Arg Val His Thr Ser Arg Ala Lys Gly Lys Gln Cys Phe Leu Val Leu
65              70              75              80

Arg Gln Gln Phe Asn Val Gln Ala Leu Val Ala Val Gly Asp His
            85              90              95

Ala Ser Lys Gln Met Val Lys Phe Ala Ala Asn Ile Asn Lys Glu Ser
        100             105             110

Ile Val Asp Val Glu Gly Val Arg Lys Val Asn Gln Lys Ile Gly
        115             120             125

Ser Cys Thr Gln Gln Asp Val Glu Leu His Val Gln Lys Ile Tyr Val
    130             135             140

Ile Ser Leu Ala Glu Pro Arg Leu Pro Leu Gln Leu Asp Asp Ala Val
145             150             155             160

Arg Pro Glu Ala Glu Gly Glu Gly Arg Ala Thr Val Asn Gln
            165             170             175

Asp Thr Arg Leu Asp Asn Arg Val Ile Asp Leu Arg Thr Ser Thr Ser
        180             185             190

Gln Ala Val Phe Arg Leu Gln Ser Gly Ile Cys His Leu Phe Arg Glu
    195             200             205

Thr Leu Ile Asn Lys Gly Phe Val Glu Ile Gln Thr Pro Lys Ile Ile
    210             215             220

Ser Ala Ala Ser Glu Gly Gly Ala Asn Val Phe Thr Val Ser Tyr Phe
225             230             235             240

Lys Asn Asn Ala Tyr Leu Ala Gln Ser Pro Gln Leu Tyr Lys Gln Met
            245             250             255

Cys Ile Cys Ala Asp Phe Glu Lys Val Phe Ser Ile Gly Pro Val Phe
            260             265             270

Arg Ala Glu Asp Ser Asn Thr His Arg His Leu Thr Glu Phe Val Gly
    275             280             285

Leu Asp Ile Glu Met Ala Phe Asn Tyr His Tyr His Glu Val Met Glu
    290             295             300

Glu Ile Ala Asp Thr Met Val Gln Ile Phe Lys Gly Leu Gln Glu Arg
305             310             315             320

Phe Gln Thr Glu Ile Gln Thr Val Asn Lys Gln Phe Pro Cys Glu Pro
            325             330             335

Phe Lys Phe Leu Glu Pro Thr Leu Arg Leu Glu Tyr Cys Glu Ala Leu
            340             345             350

Ala Met Leu Arg Glu Ala Gly Val Glu Met Gly Asp Glu Asp Leu
    355             360             365

Ser Thr Pro Asn Glu Lys Leu Leu Gly His Leu Val Lys Glu Lys Tyr
    370             375             380

Asp Thr Asp Phe Tyr Ile Leu Asp Lys Tyr Pro Leu Ala Val Arg Pro
385             390             395             400

Phe Tyr Thr Met Pro Asp Pro Arg Asn Pro Lys Gln Ser Asn Ser Tyr
            405             410             415

Asp Met Phe Met Arg Gly Glu Glu Ile Leu Ser Gly Ala Gln Arg Ile
            420             425             430

His Asp Pro Gln Leu Leu Thr Glu Arg Ala Leu His His Gly Ile Asp
    435             440             445

Leu Glu Lys Ile Lys Ala Tyr Ile Asp Ser Phe Arg Phe Gly Ala Pro
    450             455             460

```
Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
                485                 490                 495

Lys Arg Leu Thr Pro
            500

<210> SEQ ID NO 2
<211> LENGTH: 2322
<212> TYPE: DNA
<213> ORGANISM: Homo sapiens

<400> SEQUENCE: 2
atctcgagat agccgcagct ctcgcgatct ttctggagcc gcacctccac gcggagtccg    60
agcgcgtgtg ctgagacccc agggtcggga gggcggagac tgggagggag ggagaagccc   120
ctttggcctg ccttacggaa gcctgcgagg gagggtggtg tccactgccc agttccgtgt   180
cccgatgccc agcgccagcg ccagccgcaa gagtcaggag aagccgcggg agatcatgga   240
cgcggcggaa gattatgcta agagagatat ggaatatct tcaatgatac aatcacaaga    300
aaaaccagat cgagttttgg ttcgggttag agacttgaca atacaaaaag ctgatgaagt   360
tgtttgggta cgtgcaagag ttcatacaag cagagctaaa gggaaacagt gcttcttagt   420
cctacgtcag cagcagttta atgtccaggc tcttgtggcg gtgggagacc atgcaagcaa   480
gcagatggtt aaatttgctg ccaacatcaa caaagagagc attgtggatg tagaaggtgt   540
tgtgagaaaa gtgaatcaga aaattggaag ctgtacacag caagacgttg agttacatgt   600
tcagaagatt tatgtgatca gtttggctga accccgtctg cccctgcagc tggatgatgc   660
tgttcggcct gaggcagaag gagaagagga aggaagagct actgttaacc aggatacaag   720
attagacaac agagtcattg atcttaggac atcaactagt caggcagtct tccgtctcca   780
gtctggcatc tgccatctct tccgagaaac tttaattaac aaaggttttg tggaaatcca   840
aactcctaaa attatttcag ctgccagtga aggaggagcc aatgttttta ctgtgtcata   900
ttttaaaaat aatgcatacc tggctcagtc cccacagcta taagcaaa tgtgcatttg    960 tgctgatttt gagaaggttt tctctattgg accagtattc agagcggaag actctaatac  1020
ccatagacat ctaactgagt ttgttggttt ggacattgaa atggctttta attaccatta  1080
ccacgaagtt atggaagaaa ttgctgacac catggtacaa atattcaaag acttcaaga   1140 aaggtttcag actgaaattc aaacagtgaa taaacagttc ccatgtgagc cattcaaatt  1200
tttggagcca actctaagac tagaatattg tgaagcattg gctatgctta gggaagctgg  1260
agtcgaaatg ggagatgaag acgatctgag cacaccaaat gaaaagctgt gggtcatttt  1320
ggtaaaggaa aagtatgata cagattttta tattcttgat aaatatccat ggctgtaag   1380 acctttctat accatgcctg acccaagaaa tcccaaacag tccaactctt acgatatgtt  1440
catgagagga gaagaaatat tgtcaggagc tcaaagaata catgatcctc aactgctaac  1500
agagagagct ttacatcatg gaattgattt ggagaaaatt aaggcttaca ttgattcctt  1560
ccgctttgga gccctcctc atgctggtgg aggcattgga ttggaacgag ttactatgct   1620
gtttctggga ttgcataatg ttcgtcagac ctccatgttc cctcgtgatc ccaaacgact  1680
cactccttaa attcacactt tgccacttaa ctccagtgtg gatgacagag cgagaccctg  1740
cctcaaaaaa aaaaaaaaaa aagaaagcc acacttattc ttttcagtaa cctgctagtg   1800
cacaggctgt actttaggta cttaaaatat gcactagaat aaatttgcaa ggccctaaaa  1860
```

-continued

```
tatcactgtt attttttggag taattcagta taggttcgtt taaaagagat ttttataact    1920
tcagacatgc atcagtagga aataacttga gaaattcata tggttatgtt acaaattcat    1980
attctgttac tacagtaaac gttaagagtt ttaaacagtt aagattgtac aattttcctt    2040
cttttctata ttacaagggc cccagtgtta atgtcttaga ttttcagtat ttgaacttat    2100
ttttttaaat tctgtcattg agataagaat aattcaggta gcatctgaaa ttttaatgaa    2160
tgtataattg gcatatcatg gaaaattaac cagaaagtat cagttcttaa aagttatgcc    2220
tagaaattat gtaaagctaa actactggtt agaaagtatt cagtgtaata ttgtattaat    2280
ttgttaaatt ctaaacttga atttcaataa aattttaaag ct                       2322
```

<210> SEQ ID NO 3
<211> LENGTH: 32
<212> TYPE: PRT
<213> ORGANISM: Homo sapiens

<400> SEQUENCE: 3

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

<210> SEQ ID NO 4
<211> LENGTH: 32
<212> TYPE: PRT
<213> ORGANISM: Rattus norvegicus

<400> SEQUENCE: 4

Met Pro Ser Ala Asn Ala Ser Arg Lys Gly Gln Glu Lys Pro Arg Glu
1               5                   10                  15

Ile Val Asp Ala Ala Glu Asp Tyr Ala Lys Glu Arg Tyr Gly Val Ser
            20                  25                  30

<210> SEQ ID NO 5
<211> LENGTH: 11
<212> TYPE: PRT
<213> ORGANISM: Artificial Sequence
<220> FEATURE:
<223> OTHER INFORMATION: Consensus sequence of the positively charged
      residues of the AspRS amphiphilic helix
<220> FEATURE:
<221> NAME/KEY: VARIANT
<222> LOCATION: 5, 9, 10
<223> OTHER INFORMATION: Xaa = Any non-positively charged amino acid

<400> SEQUENCE: 5

Leu Ser Lys Lys Xaa Leu Lys Lys Xaa Xaa Lys
1               5                   10

<210> SEQ ID NO 6
<211> LENGTH: 25
<212> TYPE: PRT
<213> ORGANISM: Anopheles gambiae

<400> SEQUENCE: 6

Glu Glu Pro Val Gly Ala Gly Ala Glu Ala Thr Ser Lys Lys Ala Ala
1               5                   10                  15

Lys Lys Ala Ala Lys Asp Ala Glu Lys
            20                  25

<210> SEQ ID NO 7
<211> LENGTH: 27

```
<212> TYPE: PRT
<213> ORGANISM: Ixodes scapularis

<400> SEQUENCE: 7

Asp Glu Asn Ala Ala Leu Gly Pro Asp Gly Gln Pro Leu Ser Lys Lys
1               5                   10                  15

Ala Leu Lys Lys Gln Ala Lys Glu Gln Glu Lys
            20                  25

<210> SEQ ID NO 8
<211> LENGTH: 19
<212> TYPE: PRT
<213> ORGANISM: Lottia gigantea

<400> SEQUENCE: 8

Asp Gly Lys Pro Thr Ser Lys Lys Gly Leu Lys Lys Gln Gln Lys Glu
1               5                   10                  15

Ala Glu Lys

<210> SEQ ID NO 9
<211> LENGTH: 27
<212> TYPE: PRT
<213> ORGANISM: Helobdella robusta

<400> SEQUENCE: 9

Asn Val Ser Glu Ala Val Gly Gly Asp Asp Lys Pro Thr Ser Lys Lys
1               5                   10                  15

Ala Leu Lys Lys Gln Gln Lys Glu Ala Glu Lys
            20                  25

<210> SEQ ID NO 10
<211> LENGTH: 23
<212> TYPE: PRT
<213> ORGANISM: Xenopus trapicalis

<400> SEQUENCE: 10

Ser Ala Ala Ser Glu Glu Gln Ala Gln Ser Lys Lys Ala Leu Lys Lys
1               5                   10                  15

Gln Gln Lys Glu Ala Glu Lys
            20

<210> SEQ ID NO 11
<211> LENGTH: 26
<212> TYPE: PRT
<213> ORGANISM: Takifugu rubripes

<400> SEQUENCE: 11

Ser Cys Phe Ser Ala Ala Glu Ala Glu Gln Ala Gln Ser Lys Lys Gly
1               5                   10                  15

Leu Lys Lys Gln Gln Lys Glu Ala Glu Lys
            20                  25

<210> SEQ ID NO 12
<211> LENGTH: 26
<212> TYPE: PRT
<213> ORGANISM: Tetraodon nigroviridis

<400> SEQUENCE: 12

Asp Val Lys Gly Ala Ala Glu Glu Gln Ala Gln Ser Lys Lys Gly
1               5                   10                  15

Leu Lys Lys Gln Gln Lys Glu Ala Glu Lys
            20                  25
```

<210> SEQ ID NO 13
<211> LENGTH: 27
<212> TYPE: PRT
<213> ORGANISM: Gasterosteus aculeatus

<400> SEQUENCE: 13

Glu Ala Pro Gly Ala Thr Glu Glu Gln Gln Ala Gln Ser Lys Lys
1               5                   10                  15

Gly Leu Lys Lys Gln Gln Lys Glu Ala Glu Lys
            20                  25

<210> SEQ ID NO 14
<211> LENGTH: 23
<212> TYPE: PRT
<213> ORGANISM: Gallus gallus

<400> SEQUENCE: 14

Pro Ser Ala Ala Gly Arg Gly Gln Gly Lys Asp Arg Arg Pro Asp Asn
1               5                   10                  15

Glu Glu Gln Pro Ala Ala Asp
            20

<210> SEQ ID NO 15
<211> LENGTH: 21
<212> TYPE: PRT
<213> ORGANISM: Bos taurus

<400> SEQUENCE: 15

Pro Ser Ala Ser Ala Ser Arg Lys Ser Gln Glu Lys Pro Arg Glu Ile
1               5                   10                  15

Met Asp Ala Ala Glu
            20

<210> SEQ ID NO 16
<211> LENGTH: 20
<212> TYPE: PRT
<213> ORGANISM: Rattus norvegicus

<400> SEQUENCE: 16

Pro Ser Ala Asn Ala Ser Arg Lys Ser Gln Glu Lys Pro Arg Glu Ile
1               5                   10                  15

Asp Ala Ala Glu
            20

<210> SEQ ID NO 17
<211> LENGTH: 21
<212> TYPE: PRT
<213> ORGANISM: Mus musculus

<400> SEQUENCE: 17

Pro Ser Ala Ser Ala Ser Arg Lys Ser Gln Glu Lys Pro Arg Glu Ile
1               5                   10                  15

Met Asp Ala Ala Glu
            20

<210> SEQ ID NO 18
<211> LENGTH: 21
<212> TYPE: PRT
<213> ORGANISM: Procavia capensis

<400> SEQUENCE: 18

```
Pro Ser Ala Ser Ala Gly Arg Lys Asn Gln Glu Lys Pro Arg Glu Ile
1               5                   10                  15

Met Asp Ala Ala Glu
            20

<210> SEQ ID NO 19
<211> LENGTH: 21
<212> TYPE: PRT
<213> ORGANISM: Monodephis domestica

<400> SEQUENCE: 19

Pro Ser Ala Ile Ala Ser Arg Lys Thr Gln Glu Lys Pro Arg Glu Ile
1               5                   10                  15

Met Asp Ala Ala Glu
            20

<210> SEQ ID NO 20
<211> LENGTH: 21
<212> TYPE: PRT
<213> ORGANISM: Tarius syrichta

<400> SEQUENCE: 20

Pro Ser Ala Ser Ala Ser Arg Arg Ser Gln Glu Lys Pro Arg Glu Ile
1               5                   10                  15

Met Asp Ala Ala Glu
            20

<210> SEQ ID NO 21
<211> LENGTH: 21
<212> TYPE: PRT
<213> ORGANISM: Pongo abelii

<400> SEQUENCE: 21

Pro Ser Ala Ser Ala Ser Arg Lys Ser Gln Glu Lys Pro Arg Glu Ile
1               5                   10                  15

Met Asp Ala Ala Glu
            20

<210> SEQ ID NO 22
<211> LENGTH: 21
<212> TYPE: PRT
<213> ORGANISM: Pan troglodytes

<400> SEQUENCE: 22

Pro Ser Ala Asp Ala Ser Arg Lys Ser Gln Glu Lys Pro Arg Glu Ile
1               5                   10                  15

Met Asp Ala Ala Glu
            20

<210> SEQ ID NO 23
<211> LENGTH: 21
<212> TYPE: PRT
<213> ORGANISM: Homo sapiens

<400> SEQUENCE: 23

Pro Ser Ala Ser Ala Cys Arg Lys Ser Gln Glu Lys Pro Arg Glu Ile
1               5                   10                  15

Met Asp Ala Ala Glu
            20
```

COMPOSITIONS AND METHODS COMPRISING ASPARTYL-TRNA SYNTHETASES HAVING NON-CANONICAL BIOLOGICAL ACTIVITIES

CROSS REFERENCE TO RELATED APPLICATIONS

This application is a Continuation of U.S. application Ser. No. 12/751,358, filed Mar. 31, 2010; which claims the benefit under 35 U.S.C. § 119(e) of U.S. Provisional Patent Application No. 61/165,194, filed Mar. 31, 2009, which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ATYR-01202US_ST25_SEQ_LISTING.txt. The text file is 13 KB, was created on May 4, 2015, and is being submitted electronically via EFS-Web.

BACKGROUND OF THE INVENTION

Field of the Invention

The present invention relates generally to forms of aspartyl-tRNA synthetase (AspRS) polypeptides, compositions comprising such polypeptides, and methods of using same.

Description of the Related Art

Aminoacyl-tRNA synthetases, which catalyze the aminoacylation of tRNA molecules, are essential for decoding genetic information during the process of translation. In higher eukaryotes, aminoacyl-tRNA synthetases associate with other polypeptides to form supramolecular multienzyme complexes. Each of the eukaryotic tRNA synthetases consists of a core enzyme, which is closely related to the prokaryotic counterpart of the tRNA synthetase, and an additional domain that is appended to the amino-terminal or carboxyl-terminal end of the core enzyme. Human tyrosyl-tRNA synthetase (TyrRS), for example, has a carboxyl-terminal domain that is not part of prokaryotic and lower eukaryotic TyrRS molecules.

Several aminoacyl-tRNA synthetases have been demonstrated to have non-canonical functions distinct from their involvement in translation. For example, Mini-tyrosyl tRNA synthetase (mini-TyrRS), the N-terminal domain of TyrRS which corresponds to amino acid residues 1-364 and is cleaved by polymorphonuclear cell elastase and plasmin, is a member of the aminoacyl tRNA synthetase "AARS" multifunction cytokine-like proteins and peptides. In vitro, Mini-TyrRS has been shown to stimulate neutrophil activation and chemotaxis, endothelial cell proliferation and migration, and is pro-angiogenic in chick chorioallantoic membrane (CAM) and mouse matrigel assays. Mini-TyrRS has an ELR motif that, like CXC-chemokines such as IL-8, confers its chemokine and angiogenic activities. Like other ELR-containing cytokines, mutation of this motif inhibits mini-TyrRS binding and stimulation of leukocytes and angiogenesis.

In addition, truncated forms or TrpRS have been demonstrated to have angiogenic properties. In normal human cells, there are two forms of TrpRS that can be detected: a major form consisting of the full-length molecule (amino acid residues 1-471) and a minor truncated form. The minor form is generated by the deletion of an amino-terminal domain through alternative splicing of the pre-mRNA. The amino-terminus of miniTrpRS has been determined to be the methionine residue at position 48 of the full-length TrpRS molecule. Alternatively, truncated TrpRS can be generated by proteolysis. For example, bovine TrpRS is highly expressed in the pancreas and is secreted into the pancreatic juice, thus resulting in the production of a truncated TrpRS molecule. Additional studies indicate that mini-TrpRS inhibits VEGF-induced cell proliferation and migration (Wakasugi et al., Proc. Natl. Acad. Sci. 99: 173-177 (2002)). In particular, a chick CAM assay shows that mini TrpRS blocks angiogenic activity of VEGF. In contrast, the full-length TrpRS does not inhibit angiogenesis. Thus, removal of the first 48 amino acid residues exposes the anti-angiogenic activity of TrpRS. Therefore, as with TyrRS, certain forms of TrpRS possess activities other than the aminoacylation of tRNA.

Given these observations of non-canonical and therapeutically relevant activities associated alternative forms of TyrRS and TrpRS, there is a need to identify biologically relevant forms and/or activities of other aminoacyl-tRNA synthetase proteins in order to exploit the full therapeutic potential of this family of proteins. Accordingly, the present invention addresses these needs and offers other related advantages.

SUMMARY OF THE INVENTION

The present invention stems from the discovery that certain aspartyl-tRNA synthetase (AspRS) polypeptides possess non-canonical biological activities of therapeutic relevance. Therefore, according to one aspect, the present invention provides isolated AspRS polypeptides having at least one non-canonical biological activity, as well active fragments and variants thereof which substantially retain said non-canonical activity. "Non-canonical" activity," as used herein, refers generally to an activity possessed by a AspRS polypeptide of the invention that is other than aminoacylation and, more specifically, other than the addition of aspartic acid onto a tRNA$^{Asp}$ molecule. As detailed herein, in certain embodiments, a non-canonical biological activity exhibited by a AspRS polypeptide of the invention may include, but is not limited to, modulation of cell proliferation, modulation of apoptosis, modulation of inflammation, modulation of cell differentiation, modulation of angiogenesis, modulation of cell binding, modulation of Akt-mediated cell signaling, modulation of cellular metabolism, modulation of cytokine production or activity, and modulation of toll-like receptor signaling, and the like.

In certain embodiments, the AspRS polypeptide of the invention is a contiguous fragment of a full length mammalian AspRS protein. In a more specific embodiment, the AspRS polypeptide is a contiguous fragment of the human AspRS protein sequence set forth in SEQ ID NO: 1. Illustratively, the fragments may be of essentially any length, provided they are not full length and further provided they retain at least one non-canonical biological activity of interest. In certain illustrative embodiments, a AspRS polypeptide of the invention will range in size from about 20-50, 20-100, 20-200, 20-300, 20-400, or 20-500 amino acids in length. In other embodiments, the AspRS polypeptide of the invention will range in size from about 50-100, 50-200, 50-300, 50-400, or 50-500 amino acids in length. In other embodiments, the AspRS polypeptide of the invention will range in size from about 100-200, 100-300, 100-400, or 100-500 amino acids in length. In still other illustrative embodiments, the AspRS polypeptide of the invention will range in size from about 200-300, 200-400, or 200-500 amino acids in length.

In further embodiments of the invention, an AspRS polypeptide comprises an active variant (i.e., retains at least one non-canonical biological activity of interest) of a fragment of an AspRS protein sequence, such as the human AspRS protein sequence set forth in SEQ ID NO: 1. In a more specific embodiment, the active variant is a polypeptide having at least 70%, 80%, 90%, 95% or 99% identity along its length to a human aspartyl-tRNA synthetase sequence set forth in SEQ ID NO: 1.

Other embodiments of the invention provide AspRS splice variants and point mutants, whether naturally or non-naturally occurring, that possess one or more non-canonical activities. In certain embodiments, the AspRS comprises an amphiphilic helix domain.

In a more specific embodiment of the invention, an AspRS polypeptide comprises a fragment of the human AspRS sequence of SEQ ID NO: 1, consisting essentially of amino acid residues 1-154, 1-171, 1-174, 1-31, 399-425, 413-476 or 397-425, or an active fragment or variant thereof that substantially retains at least one non-canonical biological activity of interest.

In other specific embodiments, the AspRS polypeptide is not a polypeptide as set forth in NCBI Accession No. NP001340.

According to another aspect of the invention, there are provided fusion proteins comprising at least one AspRS polypeptide as described herein and a heterologous fusion partner.

According to another aspect of the invention, there are provided isolated polynucleotides encoding the polypeptides and fusion proteins as described herein, as well as expression vectors comprising such polynucleotides, and host cell comprising such expression vectors. Also included are oligonucleotides that specifically hybridize to an AspRS polynucleotide. In certain embodiments, the oligonucleotide is a primer, a probe, or an antisense oligonucleotide. Other embodiments relate to RNAi agents that target an AspRS polynucleotide.

According to another aspect of the invention, there are provided binding agents (e.g., antibodies and antigen-binding fragments thereof) that have binding specificity for an AspRS polypeptide of the invention, or one of its cellular binding partners. In certain embodiments, the binding agent is an antibody, an antigen-binding fragment thereof, a peptide, a peptide mimetic, a small molecule, or an aptamer. In some embodiments, the binding agent antagonizes a non-canonical activity of the AspRS polypeptide. In other embodiments, the binding agent agonizes a non-canonical activity of the AspRS polypeptide.

According to yet another aspect of the invention, there are provided compositions, e.g., pharmaceutical compositions, comprising physiologically acceptable carriers and at least one of the isolated polypeptides, fusion proteins, binding agents such as antibodies, isolated polynucleotides, expression vectors, host cells, etc., of the invention, as described herein.

Certain embodiments relate to methods of determining presence or levels of an AspRS polypeptide in a sample, comprising contacting the sample with one or binding agents that specifically bind to an AspRS polypeptide as described herein, detecting the presence or absence of the binding agent, and thereby determining the presence or levels of the AspRS polypeptide. Certain embodiments include methods of determining presence or levels of an AspRS polypeptide in a sample, comprising introducing the sample into a molecular detector that is capable of specifically identifying an AspRS polypeptide as described herein, and thereby determining the presence or levels of the AspRS polypeptide. In specific embodiments, the molecular detector is a mass spectrometer (MS). Certain embodiments include comparing the presence or levels of the AspRS protein fragment to a control sample or a predetermined value. Some embodiments include characterizing the state of the sample to distinguish it from the control. In specific embodiments, the sample and control comprise a cell or tissue, and the method comprises distinguishing between cells or tissues of different species, cells of different tissues or organs, cells at different cellular developmental states, cells at different cellular differentiation states, or healthy and diseased cells.

Also included are methods of identifying a compound that specifically binds to an AspRS polypeptide, or one or more of its cellular binding partners, comprising a) combining the AspRS polypeptide or its cellular binding partner or both with at least one test compound under suitable conditions, and b) detecting binding of the AspRS polypeptide or its cellular binding partner or both to the test compound, thereby identifying a compound that specifically binds to the AspRS polypeptide or its cellular binding partner or both. In certain embodiments, the test compound is a polypeptide or peptide, an antibody or antigen-binding fragment thereof, a peptide mimetic, or a small molecule. In some embodiments, the test compound agonizes a non-canonical biological activity of the AspRS polypeptide or its cellular binding partner. In other embodiments, the test compound antagonizes a non-canonical biological activity of the AspRS polypeptide or its cellular binding partner. Also included are compounds identified by any of the methods provided herein.

Also provided by the present invention, in other aspects, are methods for modulating a cellular activity by contacting a cell or tissue with a composition of the invention, as described herein, wherein the cellular activity to be modulated is selected from the group consisting of cell migration, cell proliferation, apoptosis, inflammation, cell differentiation, angiogenesis, modulation of cell binding, Akt-mediated cell signaling, cellular metabolism, cytokine production, and toll-like receptor signaling, and the like. In certain embodiments, the cellular activity is cytokine production. In specific embodiments, the cytokine is any one or more of IL1-β, IL-6, IL-8, IL-10, IL-12p40, MIP1-α, MIP-1β, GRO-α, MCP-1, or IL-1ra. In some embodiments, the cellular activity is toll-like receptor (TLR) signaling. In particular embodiments, the TLR is TLR2, TLR4, or both. Certain embodiments include methods of stimulating an innate immune response. In some embodiments, the cell is in a subject.

In other aspects, the present invention provides methods for treating a disease, disorder or other condition in a subject in need thereof by administering a composition according to the present invention. By way of illustration, such diseases, disorders or conditions may include, but are not limited to, inflammatory diseases, autoimmune diseases, neoplastic diseases (e.g., cancers), metabolic diseases, neurological diseases, infections, cardiovascular diseases, and diseases associated with abnormal angiogenesis.

BRIEF DESCRIPTION OF SEQUENCE IDENTIFIERS

SEQ ID NO: 1 is the full length amino acid sequence of human aspartyl-tRNA synthetase (AspRS).

SEQ ID NO: 2 is a nucleic acid sequence encoding the AspRS polypeptide of SEQ ID NO: 1.

SEQ ID NO:3 is the amino acid sequence of a 32 amino acid human AspRS peptide.

SEQ ID NO:4 is the amino acid sequence of a 32 amino acid rat AspRS peptide.

SEQ ID NO:5 is a consensus sequence of the positively charged residues of the AspRS amphiphilic helix.

SEQ ID NO:6 is the amino acid sequence of a portion of an *anopheles* mosquito AspRS N-terminal helix.

SEQ ID NO:7 is the amino acid sequence of a portion of a deer tick AspRS N-terminal helix.

SEQ ID NO:8 is the amino acid sequence of a portion of an owl limpet AspRS N-terminal helix.

SEQ ID NO:9 is the amino acid sequence of a portion of a leach AspRS N-terminal helix.

SEQ ID NO:10 is the amino acid sequence of a portion of a *Xenopus* AspRS N-terminal helix.

SEQ ID NO:11 is the amino acid sequence of a portion of a Japanese puffer fish AspRS N-terminal helix.

SEQ ID NO:12 is the amino acid sequence of a portion of a green spotted puffer AspRS N-terminal helix.

SEQ ID NO:13 is the amino acid sequence of a portion of the stickleback AspRS N-terminal helix.

SEQ ID NO:14 is the amino acid sequence of a portion of a chicken AspRS N-terminal helix.

SEQ ID NO:15 is the amino acid sequence of a portion of a bovine AspRS N-terminal helix.

SEQ ID NO:16 is the amino acid sequence of a portion of a rat AspRS N-terminal helix.

SEQ ID NO:17 is the amino acid sequence of a portion of a mouse AspRS N-terminal helix.

SEQ ID NO:18 is the amino acid sequence of a portion of a rock hyrax AspRS N-terminal helix.

SEQ ID NO:19 is the amino acid sequence of a portion of an opossum AspRS N-terminal helix.

SEQ ID NO:20 is the amino acid sequence of a portion of a tarsier AspRS N-terminal helix.

SEQ ID NO:21 is the amino acid sequence of a portion of an orangutan AspRS N-terminal helix.

SEQ ID NO:22 is the amino acid sequence of a portion of a chimpanzee AspRS N-terminal helix.

SEQ ID NO:23 is the amino acid sequence of a portion of a human AspRS N-terminal helix.

BRIEF DESCRIPTION OF THE DRAWINGS

FIGS. 1A-1D show (A) the domain structure and (B) amino acid sequence of AspRS (SEQ ID NO:1), and (C and D) illustrate the SDS-PAGE separation of fragments of AspRS generated by controlled proteolysis of the full-length AspRS protein with human neutrophil elastase. FIG. 1C is an SDS-PAGE gel, 4-12% MOPS, showing full-length AspRS and digestion with PMN elastase. FIG. 1D is an SDS-PAGE gel, 12% MES, showing full-length AspRS and digestion with PMN elastase.

FIGS. 2A-2B demonstrate the activation of Akt in endothelial cells (bAEC) treated with AspRS (also referred to as DRS) fragments of the invention. FIG. 2A shows phosphorylation of Akt induced by treatment with pool of elastase generated AspRS fragments, and FIG. 2B shows a time course of Akt phosphorylation by cut pools of AspRS.

FIG. 7A shows the experimental set-up to assay cell migration using a boudin chamber, and FIG. 1B shows that RAW 264.7 macrophage cells migrate in a dose-dependent manner towards the D1 fragment.

FIG. 12A shows the steps by which RAW264.7 mouse macrophages were subjected to SDS-PAGE analysis; protein bands were cut out and analyzed by LC MS/MS and an N-terminal fragment of AspRS was identified as D1. FIG. 12B shows that the appended N-terminus of AspRS is an evolved domain. FIG. 12C shows the crystal structure of full length dimeric human AspRS solved to a resolution of 1.9 Å; the N-terminal tRNA anticodon-binding domain, the aminoacylation domain, and the 30 amino acid linker connecting the D1 fragment and the aminoacylation domain are indicated.

FIG. 13A shows in vivo TNF-α and IL-10 serum levels from mice injected intravenously with 10 mg/kg D1. Mice show an increase in TNF-α after 2 hours that is quickly cleared by 6 hours while IL-10 levels continue to increase. FIG. 13B shows in vitro TNF-α & IL-10 release from PBMCs after 4 & 24 hours respectively. Cells show an increase with D1 (250 nM) treatment but not with full-length AspRS (250 nM); LPS (10 EU) also shows a strong TNF-α response. The flow cytometry analysis in FIG. 13C reveals D1 binding to 83% of primary monocytes and 14% of the total lymphocyte population. Within primary lymphocytes, D1 binds to 76% of CD19+ B-cells.

FIG. 14A shows that D1 activates NF-kB in RAW264.7 mouse macrophages; RAW-Blue cells encoding an NF-κB-inducible secreted embryonic alkaline phosphatase reporter gene showed a dose dependent activation of NF-κB with D1 as compared to the lack of activation by AspRS. As shown in FIG. 14B, D1 (1 µM) activates both TLR2 and TLR4 over-expressing HEK293 cells whereas AspRS (1 µM) did not show activity; stably transfected HEK293 cells expressing either TLR2 or TLR4 with an NF-κB-inducible reporter demonstrated that D1 can induce NF-κB activation. In FIG. 14C, flow cytometry shows that D1 binds HEK cells over-expressing TLR2 or TLR4, but does not bind to control cells.

FIG. 15C shows an increase in in vitro TNF-α & IL-10 release from PBMCs after 24 treatment with D1 (50 nM) but not with full-length AspRS (50 nM) or with the Δ22 mutant (50 nM); the charge mutants (AAA and SKK) also show decreased activity. FIG. 15D illustrates how D1 can be released from macrophage cells and binds to monocytes, T-cells and B-cells via TLR2 and TLR4 receptors to elicit an early proinflammatory response of TNF-α release, followed by an anti-inflammatory response of IL-10 release.

In FIG. 16A, mammalian expressed D1 induces cytokine secretion in peripheral blood mononuclear cells. D1 was expressed with a conventional secretion sequence in HEK293 cells. Conditioned media containing secreted D1 was collected, concentrated and incubated with PBMC; D1 containing media induced TNF-α release which was not observed in mock transfected media. As shown in FIG. 16B, D1 activity is independent of endotoxin contamination; D1 cytokine release was unaltered in the presence of polymyxin B, an inactivator of endotoxin, whereas lipopolysaccharide (LPS) was completely inhibited. FIG. 16C shows that D1 digestion by proteinase K abolishes PBMC cytokine stimulating ability. D1 was digested completely by overnight treatment with proteinase K, and digested D1 was added to PBMC and TNF-α secretion was measured by ELISA.

DETAILED DESCRIPTION OF THE INVENTION

Figure 3:
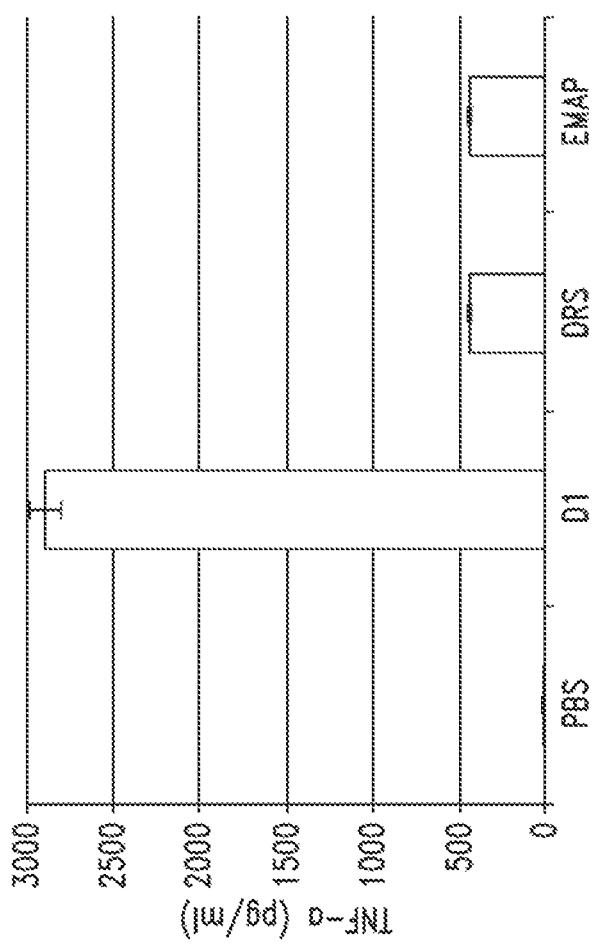
FIG. 3 shows the increased secretion of TNF-α by peripheral blood mononuclear cells (PBMCs) treated with an AspRS fragment of the invention, D1, in comparison to TNF-α secretion by PBMCs treated with either full-length AspRS (DRS) or the positive control, endothelial-monocyte-activating polypeptide II (EMAP). PBMCs were treated for 24 hours with D1, DRS, or EMAP II protein and assayed for TNF-α secretion.

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* (2nd Edition, 1989); Maniatis et al., *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); *A Practical Guide to Molecular Cloning* (B. Perbal, ed., 1984).

All publications, patents and patent applications cited herein are hereby incorporated by reference in their entirety.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

As used in this specification and the appended claims, the singular forms "a," "an" and "the" include plural references unless the content clearly dictates otherwise. By way of example, "an element" means one element or more than one element.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

An "agonist" refers to a molecule that intensifies or mimics the non-canonical biological activity of an AspRS. Agonists may include proteins, nucleic acids, carbohydrates, small molecules, or any other compound or composition that modulates the activity of an AspRS either by directly interacting with the AspRS or its binding partner, or by acting on components of the biological pathway in which the AspRS participates. Included are partial and full agonists.

The term "antagonist" refers to a molecule that inhibits or attenuates the non-canonical biological activity of an AspRS. Antagonists may include proteins such as antibodies, nucleic acids, carbohydrates, small molecules, or any other compound or composition that modulates the activity of an AspRS or its binding partner, either by directly interacting with the AspRS or its binding partner or by acting on components of the biological pathway in which the AspRS participates. Included are partial and full antagonists.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

As used herein, the terms "function" and "functional" and the like refer to a biological, enzymatic, or therapeutic function.

By "gene" is meant a unit of inheritance that occupies a specific locus on a chromosome and consists of transcriptional and/or translational regulatory sequences and/or a coding region and/or non-translated sequences (i.e., introns, 5' and 3' untranslated sequences).

"Homology" refers to the percentage number of amino acids that are identical or constitute conservative substitutions. Homology may be determined using sequence comparison programs such as GAP (Deveraux et al., 1984, *Nucleic Acids Research* 12, 387-395), which is incorporated herein by reference. In this way sequences of a similar or substantially different length to those cited herein could be compared by insertion of gaps into the alignment, such gaps being determined, for example, by the comparison algorithm used by GAP.

The term "host cell" includes an individual cell or cell culture that can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a recombinant host cell.

By "isolated" is meant material that is substantially or essentially free from components that normally accompany it in its native state. For example, an "isolated polynucleotide," as used herein, includes a polynucleotide that has been purified from the sequences that flank it in its naturally-occurring state, e.g., a DNA fragment which has been removed from the sequences that are normally adjacent to the fragment. Alternatively, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances.

The term "mRNA" or sometimes refer by "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. A cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

"Non-canonical" activity as used herein, refers generally to an activity possessed by an AspRS polypeptide of the invention that is other than aminoacylation and, more specifically, other than the addition of its cognate amino acid onto its cognate tRNA molecule. Non-limiting examples of non-canonical activities include RNA-binding, amino acid-binding, modulation of cell proliferation, modulation of cell migration, modulation of cell differentiation (e.g., hematopoiesis), modulation of apoptosis or other forms of cell death, modulation of cell signaling, modulation of angiogenesis, modulation of cell binding, modulation of cellular metabolism, modulation of cytokine production or activity, modulation of cytokine receptor activity, modulation of inflammation, and the like.

The term "modulating" includes "increasing" or "stimulating," as well as "decreasing" or "reducing," typically in a statistically significant or a physiologically significant amount as compared to a control. An "increased" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the amount produced by no composition (the absence of an agent or compound) or a control composition. A "decreased" or reduced amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease in the amount produced by no composition (the absence of an agent or compound) or a control composition, including all integers in between. Other examples of "statistically significant" amounts are described herein.

By "obtained from" is meant that a sample such as, for example, a polynucleotide extract or polypeptide extract is isolated from, or derived from, a particular source of the subject. For example, the extract can be obtained from a tissue or a biological fluid isolated directly from the subject. "Derived" or "obtained from" can also refer to the source of a polypeptide or polynucleotide sequence. For instance, an AspRS sequence of the present invention may be "derived" from the sequence information of an AspRS proteolytic fragment or AspRS splice variant, or a portion thereof, whether naturally-occurring or artificially generated, and may thus comprise, consist essentially of, or consist of that sequence.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

A "splice junction" as used herein includes the region in a mature mRNA transcript or the encoded polypeptide where the 3' end of a first exon joins with the 5' end of a second exon. The size of the region may vary, and may include 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 or more (including all integers in between) nucleotide or amino acid residues on either side of the exact residues where the 3' end of one exon joins with the 5' end of another exon. An "exon" refers to a nucleic acid sequence that is represented in the mature form of an RNA molecule after either portions of a precursor RNA (introns) have been removed by cis-splicing or two or more precursor RNA molecules have been ligated by trans-splicing. The mature RNA molecule can be a messenger RNA or a functional form of a non-coding RNA such as rRNA or tRNA. Depending on the context, an exon can refer to the sequence in the DNA or its RNA transcript. An "intron" refers to a non-coding nucleic acid region within a gene, which is not translated into a protein. Non-coding intronic sections are transcribed to precursor mRNA (pre-mRNA) and some other RNAs (such as long noncoding RNAs), and subsequently removed by splicing during the processing to mature RNA.

A "splice variant" refers to a mature mRNA and its encoded protein that are produced by alternative splicing, a process by which the exons of the RNA (a primary gene transcript or pre-mRNA) are reconnected in multiple ways during RNA splicing. The resulting different mRNAs may be translated into different protein isoforms, allowing a single gene to code for multiple proteins.

A "subject," as used herein, includes any animal that exhibits a symptom, or is at risk for exhibiting a symptom, which can be treated or diagnosed with an AspRS polynucleotide or polypeptide of the invention. Suitable subjects (patients) include laboratory animals (such as mouse, rat, rabbit, or guinea pig), farm animals, and domestic animals or pets (such as a cat or dog). Non-human primates and, preferably, human patients, are included.

"Treatment" or "treating," as used herein, includes any desirable effect on the symptoms or pathology of a disease or condition that can be effected by the non-canonical activities of an AspRS polynucleotide or polypeptide, as described herein, and may include even minimal changes or improvements in one or more measurable markers of the disease or condition being treated. Also included are treatments that relate to non-AspRS therapies, in which an AspRS sequence described herein provides a clinical marker of treatment. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

By "vector" or "nucleic acid construct" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated.

The terms "wild-type" and "naturally occurring" are used interchangeably to refer to a gene or gene product that has the characteristics of that gene or gene product when isolated from a naturally occurring source. A wild-type gene or gene product (e.g., a polypeptide) is that which is most frequently observed in a population and is thus arbitrarily designed the "normal" or "wild-type" form of the gene.

Aspartyl-tRNA Synthetase Polypeptides

The present invention relates generally to isolated AspRS polypeptides, polynucleotides encoding such polypeptides, binding agents that bind such polypeptides, analogs, variants and fragments of such polypeptides, etc., as well as compositions and methods of using any of the foregoing. Therefore, according to one aspect of the invention, there are provided AspRS polypeptides having non-canonical activities of therapeutic relevance, as well as compositions comprising the same.

The terms "polypeptide," "peptide," and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

Polypeptides are not limited to a specific length, but, in the context of the present invention, typically represent a fragment of a full length protein, and may include post-translational modifications, for example, glycosylations, acetylations, phosphorylations and the like, as well as other modifications known in the art, both naturally occurring and non-naturally occurring. Polypeptides and proteins of the invention may be prepared using any of a variety of well known recombinant and/or synthetic techniques, illustrative examples of which are further discussed below.

The recitation "polypeptide variant" refers to polypeptides that are distinguished from a reference AspRS polypeptide (e.g., SEQ ID NO: 1, or any of its fragments such as D1, including fragments that consist of amino acid residues 1-154, 1-171, 1-174, 1-177, 1-31, 399-425, 413-476 or 397-425 of SEQ ID NO:1) by the addition, deletion, and/or substitution of at least one amino acid residue, and which typically retain at least one non-canonical activity, as described herein. In certain embodiments, a polypeptide variant is distinguished from a reference polypeptide by one or more substitutions, which may be conservative or non-conservative, as described herein and known in the art. In certain embodiments, the polypeptide variant comprises conservative substitutions and, in this regard, it is well understood in the art that some amino acids may be changed to others with broadly similar properties without changing the nature of the activity of the polypeptide.

Polypeptide variants encompassed by the present invention will typically exhibit at least about 70%, 75%, 80%, 85%, 90%, 91%, 92%, 93%, 94%, 95%, 96%, 97%, 98%, or 99% identity (determined as described below), along their lengths, to the corresponding region of a wild-type mammalian AspRS protein, such as SEQ ID NO: 1, or any of its fragments such as D1, including fragments that consist of amino acid residues 1-154, 1-171, 1-174, 1-177, 1-31, 399-425, 413-476 or 397-425 of SEQ ID NO:1. Also included are sequences differing from the reference AspRS sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150 or more amino acids but which retain the properties of a reference AspRS polypeptide, such as a non-canonical activity. In certain embodiments, the amino acid additions or deletions occur at the C-terminal end and/or the N-terminal end of SEQ ID NO:1 or fragments thereof that consist of amino acid residues 1-154, 1-171, 1-174, 1-177, 1-31, 399-425, 413-476 or 397-425 of SEQ ID NO:1. In certain embodiments, the amino acid additions include 1, 2, 3, 4, 5, 6, 7, 8, 9, 10, 11, 12, 13, 14, 15, 16, 17, 18, 19, 20, 30, 40, 50 or more wild-type residues (i.e., from the corresponding full-length AARS polypeptide) that are proximal to the C-terminal end and/or the N-terminal end of these AspRS fragments.

In other embodiments, variant polypeptides differ from the corresponding AspRS reference sequences by at least 1% but less than 20%, 15%, 10% or 5% of the residues. (If this comparison requires alignment, the sequences should be aligned for maximum similarity. "Looped" out sequences from deletions or insertions, or mismatches, are considered differences.) The differences are, suitably, differences or changes at a non-essential residue or a conservative substitution.

Also included are biologically active "fragments" of the AspRS reference polypeptides. Representative biologically active fragments generally participate in an interaction, e.g., an intramolecular or an inter-molecular interaction. An intermolecular interaction can be a specific binding interaction or an enzymatic interaction. An inter-molecular interaction can be between an AspRS polypeptide and a cellular binding partner, such as a cellular receptor or other host molecule that participates in the non-canonical activity of the AspRS polypeptide.

Typically, biologically active fragments comprise a domain or motif with at least one activity of an AspRS reference polypeptide and may include one or more (and in some cases all) of the various active domains, and include fragments having a non-canonical activity. In some cases, biologically active fragments of an AspRS polypeptide have a biological activity that is unique to the particular, truncated fragment, such that the full-length AspRS polypeptide may not have that activity. In certain cases, the biological activity may be revealed by separating the biologically active AspRS polypeptide fragment from the other full-length AspRS polypeptide sequences, or by altering certain residues of the full-length AspRS wild-type polypeptide sequence to unmask the biologically active domains. For example, in certain illustrative embodiments, an AspRS polypeptide may comprise all or a portion of an amphiphilic helix, as illustrated herein (see, e.g., SEQ ID NO:3), and/or a region of positive charged residues (see, e.g., SEQ ID NO:5). In certain embodiments, the amphiphilic helix is a 22 amino acid region, as described herein.

A biologically active fragment of an AspRS reference polypeptide can be a polypeptide fragment which is, for example, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 220, 240, 250, 260, 280, 300 or more contiguous or non-contiguous amino acids, including all integers in between, of the amino acid sequences set forth SEQ ID NO:1. In other illustrative embodiments, an AspRS fragment of SEQ ID NO:1 may range in size from about 20-30, 20-40, 20-50, 20-60, 20-70, 20-80, 20-90, 20-100, 20-125, 20-150 or 20-175 amino acids in length. In other embodiments, the fragment will range in size from about 30-40, 30-50, 30-60, 30-70, 30-80, 30-90, 30-100, 30-125, 30-150 or 30-175 amino acids in length. In other embodiments, the fragment will range in size from about 40-50, 40-60, 40-70, 40-80, 40-90, 40-100, 40-125, 40-150 or 40-175 amino acids in length. In still other illustrative embodiments, the fragment will range in size from about 50-60, 50-70, 50-80, 50-90, 50-100, 50-125, 50-150 or 50-175 amino acids in length.

In certain embodiments, the AspRS polypeptide is a truncated AspRS polypeptide. A "truncated" AspRS, as used herein, refers to an aspartyl-tRNA synthetase protein which is shorter than its corresponding full length AspRS protein, for example, due to removal of amino acids from its N- and/or C-terminal ends. The extent of the truncation, that is, the number of N- and/or C-terminal amino acid residues removed from a full length AspRS protein can vary considerably while still providing desired cellular effects when administered to a cell, tissue or subject, as described herein. In certain embodiments, at least about 5, 10, 15, 20, 25, 50, 75, 100, 150, 200, 250, 300, 350 amino acids, or more, including all intermediate lengths, are truncated from the N- and/or C-terminus of a full length mammalian AspRS protein. Intermediate lengths are intended to include all integers therebetween, for example, 6, 7, 8, etc., 51, 52, 53, etc., 201, 202, 203, etc. Suitably, the biologically-active fragment has no less than about 1%, 10%, 25%, or 50% of a non-canonical biologically-activity of an AspRS reference polypeptide.

Also included are proteolytic fragments of an AspRS polypeptide, which can be characterized, identified, or derived according to a variety of techniques. For instance, proteolytic fragments can be identified in vitro, such as by incubating full-length or other AspRS polypeptides with selected proteases, or they can be identified endogenously (i.e., in vivo). In certain embodiments, protein fragments such as endogenous proteolytic fragments can be generated or identified, for instance, by recombinantly expressing full-length or other AspRS polypeptides in a selected microorganism or eukaryotic cell that has been either modified to contain one or more selected proteases, or that naturally contains one or more proteases that are capable of acting on a selected AspRS polypeptide, and isolating and characterizing the endogenously produced protein fragments therefrom.

In certain embodiments, protein fragments such as endogenous (e.g., naturally-occurring) proteolytic fragments can be generated or identified, for instance, from various cellular fractions (e.g., cytosolic, membrane, nuclear) and/or growth medium of various cell-types, including, for example, macrophages such as RAW macrophages (e.g., RAW 264.7 macrophages), T-cells, including primary T-cells and T-cell lines such as Jurkats, and natural killer (NK) cells, among others. In certain embodiments, protein fragments such as endogenous proteolytic fragments, however generated, can be identified by techniques such as mass-spectrometry, or equivalent techniques. Once an in vitro or endogenously identified protein fragment has been generated or identified, it can be mapped or sequenced, and, for example, cloned into an expression vector for recombinant production, or produced synthetically.

A wide variety of proteases can be used to produce, identify, derive, or characterize the sequence of AspRS proteolytic fragments. Generally, proteases are usually classified according to three major criteria: (i) the reaction catalysed, (ii) the chemical nature of the catalytic site, and (iii) the evolutionary relationship, as revealed by the structure. General examples of proteases or proteinases, as classified by mechanism of catalysis, include aspartic proteases, serine proteases, cysteine proteases, and metalloproteases.

Most aspartic proteases belong to the pepsin family. This family includes digestive enzymes, such as pepsin and chymosin, as well as lysosomal cathepsins D and processing enzymes such as renin, and certain fungal proteases (e.g., penicillopepsin, rhizopuspepsin, endothiapepsin). A second family of aspartic proteases includes viral proteinases such as the protease from the AIDS virus (HIV), also called retropepsin.

Serine proteases include two distinct families. First, the chymotrypsin family, which includes the mammalian enzymes such as chymotrypsin, trypsin, elastase, and kallikrein, and second, the substilisin family, which includes the bacterial enzymes such as subtilisin. The general 3D structure between these two families is different, but they have the same active site geometry, and catalysis proceeds via the same mechanism. The serine proteases exhibit different substrate specificities, differences which relate mainly to amino acid substitutions in the various enzyme subsites (substrate residue interacting sites). Some serine proteases have an extended interaction site with the substrate whereas others have a specificity that is restricted to the P1 substrate residue.

The cysteine protease family includes the plant proteases such as papain, actinidin, and bromelain, several mammalian lysosomal cathepsins, the cytosolic calpains (calcium-activated), as well as several parasitic proteases (e.g., *Trypanosoma, Schistosoma*). Papain is the archetype and the best studied member of the family. Recent elucidation of the X-ray structure of the Interleukin-1-beta Converting Enzyme has revealed a novel type of fold for cysteine proteinases.

The metalloproteases are one of the older classes of proteases, found in bacteria, fungi, and higher organisms. They differ widely in their sequences and their 3D structures, but the great majority of enzymes contain a zinc atom that is catalytically active. In some cases, zinc may be replaced by another metal such as cobalt or nickel without loss of proteolytic activity. Bacterial thermolysin has been well characterized and its crystallographic structure indicates that zinc is bound by two histidines and one glutamic acid. Many metalloproteases contain the sequence motif HEXXH, which provides two histidine ligands for the zinc. The third ligand is either a glutamic acid (thermolysin, neprilysin, alanyl aminopeptidase) or a histidine (astacin, serralysin).

In certain illustrative embodiments, truncated AspRS polypeptides may be produced using any of a variety of proteolytic enzymes using techniques known and available in the art. Illustrative proteases include, for example, achromopeptidase, aminopeptidase, ancrod, angiotensin converting enzyme, bromelain, calpain, calpain I, calpain II, carboxypeptidase A, carboxypeptidase B, carboxypeptidase G, carboxypeptidase P, carboxypeptidase W, carboxypeptidase Y, caspase 1, caspase 2, caspase 3, caspase 4, caspase 5, caspase 6, caspase 7, caspase 8, caspase 9, caspase 10, caspase 11, caspase 12, caspase 13, cathepsin B, cathepsin C, cathepsin D, cathepsin E, cathepsin G, cathepsin H, cathepsin L, chymopapain, chymase, chymotrypsin, clostripain, collagenase, complement C1r, complement C1s, complement Factor D, complement factor I, cucumisin, dipeptidyl peptidase IV, elastase (leukocyte), elastase (pancreatic), endoproteinase Arg-C, endoproteinase Asp-N, endoproteinase Glu-C, endoproteinase Lys-C, enterokinase, factor Xa, ficin, furin, granzyme A, granzyme B, HIV Protease, IGase, kallikrein tissue, leucine aminopeptidase (general), leucine aminopeptidase (cytosol), leucine aminopeptidase (microsomal), matrix metalloprotease, methionine aminopeptidase, neutrase, papain, pepsin, plasmin, prolidase, pronase E, prostate specific antigen, protease alkalophilic from *Streptomyces griseus*, protease from *Aspergillus*, protease from *Aspergillus saitoi*, protease from *Aspergillus sojae*, protease (*B. licheniformis*) (alkaline or alcalase), protease from *Bacillus polymyxa*, protease from *Bacillus* sp., protease from *Rhizopus* sp., protease S, proteasomes, proteinase from *Aspergillus oryzae*, proteinase 3, proteinase A, proteinase K, protein C, pyroglutamate aminopeptidase, rennin, streptokinase, subtilisin, thermolysin, thrombin, tissue plasminogen activator, trypsin, tryptase and urokinase.

Certain embodiments relate to isolated AspRS polypeptides, comprising, consisting essentially of, or consisting of amino acid sequences that have been derived from endogenous, naturally-occurring AspRS polypeptide fragments, and pharmaceutical compositions comprising said fragments, and methods of use thereof. In certain embodiments, as noted above, the sequences of AspRS protein fragments such as endogenous proteolytic fragments can be generated or identified, for instance, from various cellular fractions (e.g., cytosolic, membrane, nuclear) and/or conditioned medium from various cell-types, including primary cells and cell lines. Examples of such cell types include, without limitation, immune cells such as monocytes, dendritic cells, macrophages (e.g., RAW 264.7 macrophages; see Example 5), neutrophils, eosinophils, basophils, and lymphocytes, such as B-cells and T-cells (e.g., CD4+ helper and CD8+ killer cells), including primary T-cells and T-cell lines such as Jurkat T-cells, as well as natural killer (NK) cells.

In certain embodiments, AspRS protein fragments can be identified by techniques such as mass-spectrometry, or equivalent techniques. Merely by way of illustration and not limitation, in certain embodiments the proteomes from various cell types, tissues, or body fluids from a variety of physiological states (e.g., hyposia, diet, age, disease) or fractions thereof may be separated by 1D SDS-PAGE and the gel lanes cut into bands at fixed intervals; after which the bands may be optionally digested with an appropriate protease, such as trypsin, to release the peptides, which may then be analyzed by 1D reverse phase LC-MS/MS. The resulting proteomic data may be integrated into so-called peptographs, which plot, in the left panel, sequence coverage for a given protein in the horizontal dimension (N to C terminus, left to right) versus SDS-PAGE migration in the vertical dimension (high to low molecular weight, top to bottom). The specific peptide fragments can then be sequenced or mapped. In certain embodiments, the AspRS reference fragment may be characterized by its unique molecular weight, as compared, for example, to the molecular weight of the corresponding full-length AspRS.

As noted above, a polypeptide variant may differ from an AspRS polypeptide of the invention in one or more substitutions, deletions, additions and/or insertions. Such variants may be naturally occurring or may be synthetically generated, for example, by modifying one or more of the above polypeptide sequences of the invention and evaluating their biological activity as described herein using any of a number of techniques well known in the art.

In other illustrative embodiments, the variant may be a splice variant, whether naturally or non-naturally occurring, wherein the polypeptide possesses at least one non-canonical activity, e.g., as described herein. In other illustrative embodiments, the variant contains one or more point mutations relative to the wild type AspRS polypeptide sequence, whether naturally or non-naturally occurring, wherein the polypeptide possesses at least one non-canonical activity, e.g., as described herein.

In certain embodiments, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant of an AspRS polypeptide of the invention, one skilled in the art, for example, can change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that generally defines that protein's biological functional activity, certain amino acid sequence substitutions can be made in a protein sequence, and, of course, its underlying DNA coding sequence, and nevertheless obtain a protein with like properties. It is thus contemplated that various changes may be made in the polypeptide sequences of the disclosed compositions, or corresponding DNA sequences which encode said polypeptides without appreciable loss of their desired utility or activity.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |

TABLE 1-continued

| Amino Acids | | | Codons |
|---|---|---|---|
| Tryptophan | Trp | W | UGG |
| Tyrosine | Tyr | Y | UAC UAU |

In making such changes, the hydropathic index of amino acids may also be considered. The importance of the hydropathic amino acid index in conferring interactive biologic function on a protein is generally understood in the art (Kyte and Doolittle, 1982, incorporated herein by reference). For example, it is known that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetylmethyl-, thio- and other modified forms of adenine, cytidine, guanine, thymine and uridine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on secondary structure and hydropathic nature of the polypeptide.

Polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted, for example, using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology vol.* 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Nat'l Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Nat'l Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

Examples of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one illustrative approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

In certain embodiments of the invention, there are provided fusion polypeptides, and polynucleotides encoding fusion polypeptides. Fusion polypeptides refer to AspRS polypeptides of the invention that have been covalently linked, either directly or indirectly via an amino acid linker, to one or more heterologous polypeptide sequences (fusion partners). The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order.

The fusion partner may be designed and included for essentially any desired purpose provided they do not adversely affect the desired activity of the polypeptide. For example, in one embodiment, a fusion partner comprises a sequence that assists in expressing the protein (an expression enhancer) at higher yields than the native recombinant protein. Other fusion partners may be selected so as to increase the solubility of the protein or to enable the protein to be targeted to desired intracellular compartments. Still further fusion partners include affinity tags, which facilitate purification of the protein.

More generally, fusion to heterologous sequences, such as an Fc fragment, may be utilized to remove unwanted characteristics or to improve the desired characteristics (e.g., pharmacokinetic properties) of an AspRS polypeptide. For example, fusion to a heterologous sequence may increase chemical stability, decrease immunogenicity, improve in vivo targeting, and/or increase half-life in circulation of an AspRS polypeptide.

Fusion to heterologous sequences may also be used to create bi-functional fusion proteins, such as bi-functional proteins that are not only possess a selected non-canonical activity through the AspRS polypeptide, but are also capable of modifying (i.e., stimulating or inhibiting) other pathways through the heterologous polypeptide. Examples of such pathways include, but are not limited to, various immune system-related pathways, such as innate or adaptive immune activation pathways, or cell-growth regulatory pathways, such as angiogenesis. In certain aspects, the heterologous polypeptide may act synergistically with the AspRS polypeptide to modulate a cellular pathway in a subject. Examples of heterologous polypeptides that may be utilized to create a bi-functional fusion protein include, but are not limited to, thrombopoietin, cytokines (e.g., IL-11), chemokines, and various hematopoietic growth factors, in addition to biologically active fragments and/or variants thereof.

Fusion proteins may generally be prepared using standard techniques. For example, DNA sequences encoding the polypeptide components of a desired fusion may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures, if desired. Such a peptide linker sequence is incorporated into the fusion protein using standard techniques well known in the art. Certain peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39 46 (1985); Murphy et al., *Proc. Natl. Acad. Sci. USA* 83:8258 8262 (1986); U.S. Pat. Nos. 4,935,233 and. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

In general, polypeptides and fusion polypeptides (as well as their encoding polynucleotides) are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

In still other embodiments, an AspRS polypeptide of the invention may be part of a dimer. Dimers may include, for example, homodimers between two identical AspRS polypeptides, heterodimers between two different AspRS polypeptides (e.g., a full-length AspRS polypeptide and a truncated AspRS polypeptide or two different truncated AspRS polypeptides), and/or heterodimers between an AspRS polypeptide and a heterologous polypeptide. The monomers and/or dimmers may be soluble and may be isolated or purified to homogeneity. Certain heterodimers, such as those between an AspRS polypeptide and a heterologous polypeptide, may be bi-functional.

Also included are monomers of AspRS polypeptides, including isolated AspRS monomers that do not substantially dimerize with themselves (homodomerize) or with a second AspRS polypeptide (heterodimerize), whether due to one or more substitutions, truncations, deletions, additions, chemical modifications, or a combination of these alterations. In certain embodiments, monomeric AspRS polypeptides possess biological activities, including non-canonical activities, which are not possessed by dimeric or multimeric AspRS polypeptide complexes.

In other embodiments, an AspRS polypeptide of the invention may be part of a multi-unit complex. A multi-unit complex of the present invention can include, for example, at least 2, 3, 4, or 5 or more monomers. The monomers and/or multi-unit complexes of the present invention may be soluble and may be isolated or purified to homogeneity. Monomer units of a multi-unit complex may be different, homologous, substantially homologous, or identical to one another. However, a multi-unit complex of the invention includes at least one monomer comprising an AspRS polypeptide as described herein or, in other embodiments, at least two or more AspRS polypeptides as described herein.

Covalently linked monomers can be linked directly (by bonds) or indirectly (e.g., via a linker). For directly linking the polypeptide monomers herein, it may be beneficial to modify the polypeptides herein to enhance dimerization. For example, one or more amino acid residues of an AspRS polypeptide may be modified by the addition or substation by one or more cysteines. Methods for creating amino acid substitutions, such as cysteine substitutions, or other modifications to facilitate linking, are well known to those skilled in the art.

Certain embodiments of the present invention also contemplate the use of modified AspRS polypeptides, including modifications that improve desired characteristics of an AspRS polypeptide, as described herein. Illustrative modifications of AspRS polypeptides of the invention include, but are not limited to, chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Exemplary modifications also include pegylation of an AspRS polypeptide (see, e.g., Veronese and Harris, *Advanced Drug Delivery Reviews* 54: 453-456, 2002, herein incorporated by reference).

In certain aspects, chemoselective ligation technology may be utilized to modify truncated AspRS polypeptides of the invention, such as by attaching polymers in a site-specific and controlled manner. Such technology typically relies on the incorporation of chemoselective anchors into the protein backbone by either chemical or recombinant means and subsequent modification with a polymer carrying a complementary linker. As a result, the assembly process and the covalent structure of the resulting protein-polymer conjugate may be controlled, enabling the rational optimization of drug properties, such as efficacy and pharmacokinetic properties (see, e.g., Kochendoerfer, *Current Opinion in Chemical Biology* 9:555-560, 2005).

The AspRS polypeptides described herein may be prepared by any suitable procedure known to those of skill in the art, such as by recombinant techniques. For example, AspRS polypeptides may be prepared by a procedure including the steps of: (a) preparing a construct comprising a polynucleotide sequence that encodes an AspRS polypeptide and that is operably linked to a regulatory element; (b) introducing the construct into a host cell; (c) culturing the host cell to express the AspRS polypeptide; and (d) isolating the AspRS polypeptide from the host cell. Recombinant AspRS polypeptides can be conveniently prepared using standard protocols as described for example in Sambrook, et al., (1989, supra), in particular Sections 16 and 17; Ausubel et al., (1994, supra), in particular Chapters 10 and 16; and Coligan et al., Current Protocols in Protein Science (John Wiley & Sons, Inc. 1995-1997), in particular Chapters 1, 5 and 6.

In addition to recombinant production methods, polypeptides of the invention, and fragments thereof, may be produced by direct peptide synthesis using solid-phase techniques (Merrifield, *J. Am. Chem. Soc.* 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the desired molecule.

Polynucleotide Compositions

The present invention also provides isolated polynucleotides that encode the AspRS polypeptides of the invention, as well as compositions comprising such polynucleotides. Also included within the AspRS polynucleotides of the present invention are primers, probes, antisense oligonucleotides, and RNA interference agents that comprise all or a portion of the AspRS reference polynucleotides, which are complementary to all or a portion of these reference polynucleotides, or which specifically hybridize to these reference polynucleotides, as described herein.

As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be recognized by the skilled artisan, polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an AspRS or a portion thereof) or may comprise a variant, or a biological functional equivalent of such a sequence. Polynucleotide variants may contain one or more substitutions, additions, deletions and/or insertions, as further described below, preferably such that the desired activity of the encoded polypeptide is not substantially diminished relative to the unmodified polypeptide. The effect on the activity of the encoded polypeptide may generally be assessed as described herein.

In additional embodiments, the present invention provides isolated polynucleotides comprising various lengths of contiguous stretches of sequence identical to or complementary to an aspartyl-tRNA synthetase, wherein the isolated polynucleotides encode an AspRS as described herein. For example, polynucleotides are provided by this invention that encode at least about 100, 150, 200, 250, 300, 350, 400, 450 or 500, or more, contiguous amino acid residues of an AspRS polypeptide of the invention, as well as all intermediate lengths. It will be readily understood that "intermediate lengths", in this context, means any length between the quoted values, such as 101, 102, 103, etc.; 151, 152, 153, etc.; 201, 202, 203, etc.

The polynucleotides of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed; with the total length preferably being limited by the ease of preparation and use in the intended recombinant DNA protocol.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention, for example polynucleotides that are optimized for human and/or primate codon selection. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides and fusions thereof may be prepared, manipulated and/or expressed using any of a variety of well established techniques known and available in the art. For example, polynucleotide sequences which encode polypeptides of the invention, or fusion proteins or functional equivalents thereof, may be used in recombinant DNA molecules to direct expression of an AspRS polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, expression and/or activity of the gene product.

In order to express a desired polypeptide, a nucleotide sequence encoding the polypeptide, or a functional equivalent, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (1989), and Ausubel et al., Current Protocols in Molecular Biology (1989).

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems, such as viral-based expression systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf. et al., *Results Probl. Cell Differ.* 20:125-162 (1994)).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., *Cell* 11:223-232 (1977)) and adenine phosphoribosyltransferase (Lowy et al., *Cell* 22:817-823 (1990)) genes which can be employed in tk- or aprt-cells, respectively. Also, antimetabolite, antibiotic or herbicide resistance can be used as the basis for selection; for example, dhfr which confers resistance to methotrexate (Wigler et al., *Proc. Natl. Acad. Sci. U.S.A.* 77:3567-70 (1980)); npt, which confers resistance to the aminoglycosides, neomycin and G-418 (Colbere-Garapin et al., *J. Mol. Biol.* 150:1-14 (1981)); and als or pat, which confer resistance to chlorsulfuron and phosphinotricin acetyltransferase, respectively (Murry, supra).

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). These and other assays are described, among other places, in Hampton et al., *Serological Methods, a Laboratory Manual* (1990) and Maddox et al., *J. Exp. Med.* 158:1211-1216 (1983).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins.

According to another aspect of the invention, polynucleotides encoding polypeptides of the invention may be delivered to a subject in vivo, e.g., using gene therapy techniques. Gene therapy refers generally to the transfer of heterologous nucleic acids to the certain cells, target cells, of a mammal, particularly a human, with a disorder or conditions for which such therapy is sought. The nucleic acid is introduced into the selected target cells in a manner such that the heterologous DNA is expressed and a therapeutic product encoded thereby is produced.

Various viral vectors that can be utilized for gene therapy as taught herein include adenovirus, herpes virus, vaccinia, adeno-associated virus (AAV), or, preferably, an RNA virus such as a retrovirus. Preferably, the retroviral vector is a derivative of a murine or avian retrovirus, or is a lentiviral vector. The preferred retroviral vector is a lentiviral vector. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of additional retroviral vectors can incorporate multiple genes. All of these vectors can transfer or incorporate a gene for a selectable marker so that transduced cells can be identified and generated. By inserting a zinc finger derived-DNA binding polypeptide sequence of interest into the viral vector, along with another gene that encodes the ligand for a receptor on a specific target cell, for example, the vector may be made target specific. Retroviral vectors can be made target specific by inserting, for example, a polynucleotide encoding a protein (dimer). Illustrative targeting may be accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the zinc finger-nucleotide binding protein polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsulation. Helper cell lines which have deletions of the packaging signal include but are not limited to .PSI.2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

"Non-viral" delivery techniques for gene therapy can also be used including, for example, DNA-ligand complexes, adenovirus-ligand-DNA complexes, direct injection of DNA, $CaPO_4$ precipitation, gene gun techniques, electroporation, liposomes, lipofection, and the like. Any of these methods are widely available to one skilled in the art and would be suitable for use in the present invention. Other suitable methods are available to one skilled in the art, and it is to be understood that the present invention can be accomplished using any of the available methods of transfection. Lipofection can be accomplished by encapsulating an isolated DNA molecule within a liposomal particle and contacting the liposomal particle with the cell membrane of the target cell. Liposomes are self-assembling, colloidal particles in which a lipid bilayer, composed of amphiphilic molecules such as phosphatidyl serine or phosphatidyl choline, encapsulates a portion of the surrounding media such that the lipid bilayer surrounds a hydrophilic interior. Unilammellar or multilammellar liposomes can be constructed such that the interior contains a desired chemical, drug, or, as in the instant invention, an isolated DNA molecule.

Certain embodiments include polynucleotides that hybridize to a reference AspRS polynucleotide sequence, or to their complements, under stringency conditions described below. As used herein, the term "hybridizes under low stringency, medium stringency, high stringency, or very high stringency conditions" describes conditions for hybridization and washing. Guidance for performing hybridization reactions can be found in Ausubel et al., (1998, supra), Sections 6.3.1-6.3.6. Aqueous and non-aqueous methods are described in that reference and either can be used.

Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at room temperature. One embodiment of low stringency conditions includes hybridization in 6× sodium chloride/sodium citrate (SSC) at about 45° C., followed by two washes in 0.2×SSC, 0.1% SDS at least at 50° C. (the temperature of the washes can be increased to 55° C. for low stringency conditions).

Medium stringency conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridization at 42° C., and about 0.01 M to about 0.02 M salt for washing at 55° C.

High stringency conditions also may include 1% BSA, 1 mM EDTA, 0.5 M NaHPO$_4$ (pH 7.2), 7% SDS for hybridization at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C. One embodiment of very high stringency conditions includes hybridizing in 0.5 M sodium phosphate, 7% SDS at 65° C., followed by one or more washes in 0.2×SSC, 1% SDS at 65° C.

Other stringency conditions are well known in the art and a skilled artisan will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104.

While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, the $T_m$ of a perfectly matched duplex of DNA may be predicted as an approximation by the formula: $T_m=81.5+16.6$ ($\log_{10}$ M)+0.41 (% G+C)−0.63 (% formamide)−(600/length) wherein: M is the concentration of Na$^+$, preferably in the range of 0.01 molar to 0.4 molar; % G+C is the sum of guanosine and cytosine bases as a percentage of the total number of bases, within the range between 30% and 75% G+C; % formamide is the percent formamide concentration by volume; length is the number of base pairs in the DNA duplex. The $T_m$ of a duplex DNA decreases by approximately 1° C. with every increase of 1% in the number of randomly mismatched base pairs. Washing is generally carried out at $T_m$−15° C. for high stringency, or $T_m$−30° C. for moderate stringency.

In one example of a hybridization procedure, a membrane (e.g., a nitrocellulose membrane or a nylon membrane) containing immobilized DNA is hybridized overnight at 42° C. in a hybridization buffer (50% deionized formamide, 5×SSC, 5×Denhardt's solution (0.1% ficoll, 0.1% polyvinylpyrrolidone and 0.1% bovine serum albumin), 0.1% SDS and 200 mg/mL denatured salmon sperm DNA) containing a labeled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2×SSC and 0.1% SDS solution for 12 min at 65-68° C.

Embodiments of the present invention also include oligonucleotides, whether for detection, amplification, antisense therapies, or other purpose. For these and related purposes, the term "oligonucleotide" or "oligo" or "oligomer" is intended to encompass a singular "oligonucleotide" as well as plural "oligonucleotides," and refers to any polymer of two or more of nucleotides, nucleosides, nucleobases or related compounds used as a reagent in the amplification methods of the present invention, as well as subsequent detection methods. The oligonucleotide may be DNA and/or RNA and/or analogs thereof.

The term oligonucleotide does not necessarily denote any particular function to the reagent, rather, it is used generically to cover all such reagents described herein. An oligonucleotide may serve various different functions, e.g., it may function as a primer if it is capable of hybridizing to a complementary strand and can further be extended in the presence of a nucleic acid polymerase, it may provide a promoter if it contains a sequence recognized by an RNA polymerase and allows for transcription, and it may function to prevent hybridization or impede primer extension if appropriately situated and/or modified. An oligonucleotide may also function as a probe, or an antisense agent. An oligonucleotide can be virtually any length, limited only by its specific function, e.g., in an amplification reaction, in detecting an amplification product of the amplification reaction, or in an antisense or RNA interference application. Any of the oligonucleotides described herein can be used as a primer, a probe, an antisense oligomer, or an RNA interference agent.

The term "primer" as used herein refers to a single-stranded oligonucleotide capable of acting as a point of initiation for template-directed DNA synthesis under suitable conditions defined, for example, by buffer and temperature, in the presence of four different nucleoside triphosphates and an agent for polymerization, such as a DNA or RNA polymerase or reverse transcriptase. The length of the primer, in any given case, depends on, for example, the intended use of the primer, and generally ranges from about 15 to 30 nucleotides, although shorter and longer primers may be used. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein refers to a surface-immobilized molecule that can be recognized by a particular target. See, e.g., U.S. Pat. No. 6,582,908 for an example of arrays having all possible combinations of probes with 10, 12, and more bases. Probes and primers as used herein typically comprise at least 10-15 contiguous nucleotides of a known sequence. In order to enhance specificity, longer probes and primers may also be employed, such as probes and primers that comprise at least 20, 25, 30, 40, 50, 60, 70, 80, 90, 100, or at least 150 nucleotides of an AspRS reference sequence or its complement. Probes and primers may be considerably longer than these examples, and it is understood that any length supported by the knowledge in the art and the specification, including the tables, figures, and Sequence Listing, may be used.

Methods for preparing and using probes and primers are described in the references, for example Sambrook, J. et al. (1989) Molecular Cloning: A Laboratory Manual, 2.sup.nd ed., vol. 1-3, Cold Spring Harbor Press, Plainview N.Y.; Ausubel, F. M. et al. (1987) Current Protocols in Molecular Biology, Greene Publ. Assoc. & Wiley-Intersciences, New York N.Y.; Innis, M. et al. (1990) PCR Protocols. A Guide to Methods and Applications, Academic Press, San Diego Calif. PCR primer pairs can be derived from a known sequence, for example, by using computer programs intended for that purpose such as Primer (Version 0.5, 1991, Whitehead Institute for Biomedical Research, Cambridge Mass.).

Oligonucleotides for use as primers or probes may be selected using software known in the art. For example, OLIGO 4.06 software is useful for the selection of PCR primer pairs of up to 100 nucleotides each, and for the analysis of oligonucleotides and larger polynucleotides of up to 5,000 nucleotides from an input polynucleotide sequence of up to 32 kilobases. The Primer3 primer selection program (available to the public from the Whitehead Institute/MIT Center for Genome Research, Cambridge Mass.) allows the user to input a "mispriming library," in which sequences to avoid as primer binding sites are user-specified. The oligonucleotides and polynucleotide fragments identified by any of the above selection methods are useful in hybridization technologies, for example, as PCR or sequencing primers, microarray elements, or specific probes to identify fully or partially complementary polynucleotides in a sample of nucleic acids. Methods of oligonucleotide selection are not limited to those described herein.

The terms "antisense oligomer" or "antisense compound" or "antisense oligonucleotide" are used interchangeably and refer to a sequence of cyclic subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid:oligomer heteroduplex within the target sequence, and typically thereby prevent translation of that RNA. Also included are methods of use thereof to modulate expression of a selected AspRS transcript, such as a splice variant or proteolytic fragment, and/or its corresponding polypeptide.

Antisense oligonucleotides may contain between about 8 and 40 subunits, typically about 8-25 subunits, and preferably about 12 to 25 subunits. In certain embodiments, oligonucleotides may have exact sequence complementarity to the target sequence or near complementarity, as defined below. In certain embodiments, the degree of complementarity between the target and antisense targeting sequence is sufficient to form a stable duplex. The region of complementarity of the antisense oligomers with the target RNA sequence may be as short as 8-11 bases, but is preferably 12-15 bases or more, e.g., 12-20 bases, or 12-25 bases, including all integers in between these ranges. An antisense oligomer of about 14-15 bases is generally long enough to have a unique complementary sequence in targeting the selected AspRS transcript.

In certain embodiments, antisense oligomers as long as 40 bases may be suitable, where at least a minimum number of bases, e.g., 10-12 bases, are complementary to the target sequence. In general, however, facilitated or active uptake in cells is optimized at oligomer lengths less than about 30. For certain oligomers, described further below, an optimum balance of binding stability and uptake generally occurs at lengths of 18-25 bases. Included are antisense oligomers (e.g., PNAs, LNAs, 2'-OMe, MOE, morpholinos) that consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases, in which at least about 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 contiguous or non-contiguous bases are complementary to their AspRS target sequence, or variants thereof.

In certain embodiments, antisense oligomers may be 100% complementary to the AspRS nucleic acid target sequence, or it may include mismatches, e.g., to accommodate variants, as long as a heteroduplex formed between the oligomer and AspRS nucleic acid target sequence is sufficiently stable to withstand the action of cellular nucleases and other modes of degradation which may occur in vivo. Oligomer backbones which are less susceptible to cleavage by nucleases are discussed below. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the AspRS nucleic acid target sequence, it is effective to stably and specifically bind to the target sequence, such that a biological activity of the nucleic acid target, e.g., expression of AspRS protein(s), is modulated.

The stability of the duplex formed between an oligomer and a target sequence is a function of the binding Tm and the susceptibility of the duplex to cellular enzymatic cleavage. The Tm of an antisense oligonucleotide with respect to complementary-sequence RNA may be measured by conventional methods, such as those described by Hames et al., *Nucleic Acid Hybridization*, IRL Press, 1985, pp. 107-108 or as described in Miyada C. G. and Wallace R. B., 1987, Oligonucleotide hybridization techniques, *Methods Enzymol.* Vol. 154 pp. 94-107. In certain embodiments, antisense oligomer may have a binding Tm, with respect to a complementary-sequence RNA, of greater than body temperature and preferably greater than 50° C. Tm's in the range 60-80° C. or greater are preferred. According to well known principles, the Tm of an oligomer compound, with respect to a complementary-based RNA hybrid, can be increased by increasing the ratio of C:G paired bases in the duplex, and/or by increasing the length (in base pairs) of the heteroduplex.

Antisense oligomers can be designed to block or inhibit translation of mRNA or to inhibit natural pre-mRNA splice processing, or induce degradation of targeted mRNAs, and may be said to be "directed to" or "targeted against" a target sequence with which it hybridizes. In certain embodiments, the target sequence may include any coding or non-coding sequence of an AspRS mRNA transcript, and may thus by within an exon or within an intron. In certain embodiments, the target sequence is relatively unique or exceptional among AspRS s and is selective for reducing expression of a selected AspRS proteolytic fragment or splice variant. In certain embodiments, the target site includes a 3' or 5' splice site of a pre-processed mRNA, or a branch point. The target sequence for a splice site may include an mRNA sequence having its 5' end 1 to about 25 to about 50 base pairs downstream of a splice acceptor junction or upstream of a splice donor junction in a preprocessed mRNA. An oligomer is more generally said to be "targeted against" a biologically relevant target, such as reference AspRS polynucleotide, when it is targeted against the nucleic acid of the target in the manner described herein.

A "subunit" of an oligonucleotide refers to one nucleotide (or nucleotide analog) unit. The term may refer to the nucleotide unit with or without the attached intersubunit linkage, although, when referring to a "charged subunit", the charge typically resides within the intersubunit linkage (e.g., a phosphate or phosphorothioate linkage or a cationic linkage).

The cyclic subunits of an oligonucleotide may be based on ribose or another pentose sugar or, in certain embodiments, alternate or modified groups. Examples of modified oligonucleotide backbones include, without limitation, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Also contemplated are peptide nucleic acids (PNAs), locked nucleic acids (LNAs), 2'-O-Methyl oligonucleotides (2'-OMe), 2'-methoxyethoxy oligonucleotides (MOE), morpholinos, among other oligonucleotides known in the art.

The purine or pyrimidine base pairing moiety is typically adenine, cytosine, guanine, uracil, thymine or inosine. Also included are bases such as pyridin-4-one, pyridin-2-one, phenyl, pseudouracil, 2,4,6-trime115thoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetyltidine, 5-(carboxyhydroxymethyl)uridine, 5'-carboxymethylaminomethyl-2-thiouridine, 5-carboxymethylaminomethyluridine, β-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonyhnethyluridine, 5-methyloxyuridine, 5-methyl-2-thiouridine, 2-methylthio-N6-isopentenyladenosine, β-D-mannosylqueosine, uridine-5-oxyacetic acid, 2-thiocytidine, threonine derivatives and others (Burgin et al., 1996, Biochemistry, 35, 14090; Uhlman & Peyman, supra). By "modified bases" in this aspect is meant nucleotide bases other than adenine (A), guanine (G), cytosine (C), thymine (T), and uracil (U), as illustrated above; such bases can be used at any position in the antisense molecule. Persons skilled in the art will appreciate that depending on the uses of the oligomers, Ts and Us are interchangeable. For instance, with other antisense chemistries such as 2'-O-methyl antisense oligonucleotides that are more RNA-like, the T bases may be shown as U.

An oligonucleotide is typically complementary to a target sequence, such as a target DNA or RNA. The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity (100%) between the nucleic acids. The degree of complementarity between nucleic acid strands has significant effects on the efficiency and strength of hybridization between nucleic acid strands. While perfect complementarity is often desired, some embodiments can include one or more but preferably 20, 19, 18, 17, 16, 15, 14, 13, 12, 11, 10, 9, 8, 7, 6, 5, 4, 3, 2, or 1 mismatches with respect to the target sequence. Variations at any location within the oligomer are included. In certain embodiments, variations in sequence near the termini of an oligomer are generally preferable to variations in the interior, and if present are typically within about 10, 9, 8, 7, 6, 5, 4, 3, 2, or 1 nucleotides of the 5' and/or 3' terminus.

The term "target sequence" refers to a portion of the target RNA against which the oligonucleotide is directed, that is, the sequence to which the oligonucleotide will hybridize by Watson-Crick base pairing of a complementary sequence. In certain embodiments, the target sequence may be a contiguous region of an AspRS mRNA (e.g., a unique splice junction of an AspRS mRNA), or may be composed of non-contiguous regions of the mRNA.

The term "targeting sequence" or in certain embodiments "antisense targeting sequence" refers to the sequence in an oligonucleotide that is complementary (meaning, in addition, substantially complementary) to the target sequence in the DNA or RNA target molecule. The entire sequence, or only a portion, of the antisense compound may be complementary to the target sequence. For example, in an oligonucleotide having 20-30 bases, about 6, 7, 8, 9, 10, 11, 12, 13, 14, 15, 16, 17, 18, 19, 20, 21, 22, 23, 24, 25, 26, 27, 28, or 29 may be targeting sequences that are complementary to the target region. Typically, the targeting sequence is formed of contiguous bases, but may alternatively be formed of non-contiguous sequences that when placed together, e.g., from opposite ends of the oligonucleotide, constitute sequence that spans the target sequence.

Target and targeting sequences are described as "complementary" to one another when hybridization occurs in an antiparallel configuration. A targeting sequence may have "near" or "substantial" complementarity to the target sequence and still function for the purpose of the present invention, that is, it may still be functionally "complementary."

An oligonucleotide "specifically hybridizes" to a target polynucleotide if the oligomer hybridizes to a target (e.g., an AspRS reference polynucleotide or its complement) under physiological conditions, with a Tm substantially greater than 45° C., preferably at least 50° C., and typically 60° C.-80° C. or higher. Such hybridization preferably corresponds to stringent hybridization conditions. At a given ionic strength and pH, the Tm is the temperature at which 50% of a target sequence hybridizes to a complementary polynucleotide. Again, such hybridization may occur with "near" or "substantial" complementarity of the antisense oligomer to the target sequence, as well as with exact complementarity.

The terms specifically binds or specifically hybridizes refer generally to an oligonucleotide probe or polynucleotide sequence that not only binds to its intended target gene sequence in a sample under selected hybridization conditions, but does not bind significantly to other target sequences in the sample, and thereby discriminates between its intended target and all other targets in the target pool. A probe that specifically hybridizes to its intended target sequence may also detect concentration differences under the selected hybridization conditions, as described herein.

As noted above, certain oligonucleotides provided herein include peptide nucleic acids (PNAs). Also included are "locked nucleic acid" subunits (LNAs). The structures of LNAs are known in the art: for example, Wengel, et al., Chemical Communications (1998) 455; Tetrahedron (1998) 54, 3607, and Accounts of Chem. Research (1999) 32, 301); Obika, et al., Tetrahedron Letters (1997) 38, 8735; (1998) 39, 5401, and Bioorganic Medicinal Chemistry (2008)16, 9230. Certain oligonucleotides may comprise morpholino-based subunits bearing base-pairing moieties, joined by uncharged or substantially uncharged linkages. The terms "morpholino oligomer" or "PMO" (phosphoramidate- or phosphorodiamidate morpholino oligomer) refer to an oligonucleotide analog composed of morpholino subunit structures, where (i) the structures are linked together by phosphorus-containing linkages, one to three atoms long, preferably two atoms long, and preferably uncharged or cationic, joining the morpholino nitrogen of one subunit to a 5' exocyclic carbon of an adjacent subunit, and (ii) each morpholino ring bears a purine or pyrimidine or an equivalent base-pairing moiety effective to bind, by base specific hydrogen bonding, to a base in a polynucleotide.

In certain embodiments, oligonucleotides can be prepared by stepwise solid-phase synthesis, employing methods detailed in the references cited above, and below with respect to the synthesis of oligonucleotides having a mixture or uncharged and cationic backbone linkages. In some cases, it may be desirable to add additional chemical moieties to the oligonucleotide, e.g., to enhance pharmacokinetics or to facilitate capture or detection of the compound. Such a moiety may be covalently attached, typically to a terminus of the oligomer, according to standard synthetic methods. For example, addition of a polyethylene glycol moiety or other hydrophilic polymer, e.g., one having 10-100 monomeric subunits, may be useful in enhancing solubility. One or more charged groups, e.g., anionic charged groups such as an organic acid, may enhance cell uptake.

A variety of detectable molecules may be used to render an oligonucleotide detectable, such as a radioisotopes, fluorochromes, dyes, enzymes, nanoparticles, chemiluminescent markers, biotin, or other monomer known in the art that can be detected directly (e.g., by light emission) or indirectly (e.g., by binding of a fluorescently-labeled antibody).

Certain embodiments relate to RNA interference (RNAi) agents that target one or more mRNA transcripts of an AspRS reference polynucleotide, including fragments and variants thereof. Also included are methods of use thereof to modulate the levels of a selected AspRS transcript, such as an AspRS splice variant or proteolytic fragment.

The term "double-stranded" means two separate nucleic acid strands comprising a region in which at least a portion of the strands are sufficiently complementary to hydrogen bond and form a duplex structure. The term "duplex" or "duplex structure" refers to the region of a double stranded molecule wherein the two separate strands are substantially complementary, and thus hybridize to each other. "dsRNA" refers to a ribonucleic acid molecule having a duplex structure comprising two complementary and anti-parallel nucleic acid strands (i.e., the sense and antisense strands). Not all nucleotides of a dsRNA must exhibit Watson-Crick base pairs; the two RNA strands may be substantially complementary. The RNA strands may have the same or a different number of nucleotides.

The strands of a dsRNA are sufficiently complementary to hybridize to form a duplex structure. In certain embodiments, the complementary RNA strand may be less than 30 nucleotides, less than 25 nucleotides in length, or even 19 to 24 nucleotides in length. In certain aspects, the complementary nucleotide sequence may be 20-23 nucleotides in length, or 22 nucleotides in length.

In certain embodiments, at least one of the RNA strands comprises a nucleotide overhang of 1 to 4 nucleotides in length. In other embodiments, one or both of the strands are blunt-ended. In certain embodiments, the dsRNA may further comprise at least one chemically modified nucleotide.

Certain embodiments of the present invention may comprise microRNAs. Micro-RNAs represent a large group of small RNAs produced naturally in organisms, some of which regulate the expression of target genes. Micro-RNAs are formed from an approximately 70 nucleotide single-stranded hairpin precursor transcript by Dicer. (V. Ambros et al. Current Biology 13:807, 2003).

Certain embodiments may also employ short-interfering RNAs (siRNA). Each strand of an siRNA agent can be equal to or less than 35, 30, 25, 24, 23, 22, 21, 20, 19, 18, 17, 16, or 15 nucleotides in length. The strand is preferably at least 19 nucleotides in length. For example, each strand can be between 21 and 25 nucleotides in length. Preferred siRNA agents have a duplex region of 17, 18, 19, 29, 21, 22, 23, 24, or 25 nucleotide pairs, and one or more overhangs, preferably one or two 3' overhangs, of 2-3 nucleotides.

A "single strand RNAi agent" as used herein, is an RNAi agent which is made up of a single molecule. It may include a duplexed region, formed by intra-strand pairing, e.g., it may be, or include, a hairpin or pan-handle structure. A single strand RNAi agent is at least 14, and more preferably at least 15, 20, 25, 29, 35, 40, or 50 nucleotides in length. It is preferably less than 200, 100, or 60 nucleotides in length.

Hairpin RNAi modulating agents may have a duplex region equal to or at least 17, 18, 19, 29, 21, 22, 23, 24, or 25 nucleotide pairs. The duplex region may preferably be equal to or less than 200, 100, or 50, in length. Certain ranges for the duplex region are 15-30, 17 to 23, 19 to 23, and 19 to 21 nucleotides pairs in length. The hairpin may have a single strand overhang or terminal unpaired region, preferably the 3', and preferably of the antisense side of the hairpin. In certain embodiments, overhangs are 2-3 nucleotides in length.

The present invention further encompasses oligonucleotides employing ribozymes. Also included are vector delivery systems that are capable of expressing the AspRS-targeting sequences described herein. Included are vectors that express siRNA or other duplex-forming RNA interference molecules. Exemplary delivery systems may include viral vector systems (i.e., viral-mediated transduction) including, but not limited to, retroviral (e.g., lentiviral) vectors, adenoviral vectors, adeno-associated viral vectors, and herpes viral vectors, among others known in the art.

Oligonucleotides and RNAi agents that target one or more portions of an AspRS polynucleotide reference sequence or its complement may be used in any of the therapeutic, diagnostic, or drug screening methods described herein and apparent to persons skilled in the art.

Antibody Compositions, Fragments Thereof and Other Binding Agents

According to another aspect, the present invention further provides binding agents, such as antibodies, antigen-binding fragments thereof, soluble receptors, small molecules, aptamers etc., that exhibit binding specificity for a polypeptide disclosed herein, or to a portion, variant or derivative thereof, and methods of using same. Preferably, such binding agents are effective for modulating one or more of the non-canonical activities mediated by an AspRS polypeptide of the invention. In certain embodiments, for example, the binding agent is one that binds to an AspRS polypeptide of the invention and inhibits its ability to bind to one or more of its cellular binding partners. Accordingly, such binding agents may be used to treat or prevent diseases, disorders or other conditions that are mediated by an AspRS polypeptide of the invention by antagonizing it activity.

An antibody, or antigen-binding fragment thereof, is said to "specifically bind," "immunologically bind," and/or is "immunologically reactive" to a polypeptide of the invention if it reacts at a detectable level (within, for example, an ELISA assay) with the polypeptide, and does not react detectably with unrelated polypeptides under similar conditions.

Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, e.g., Davies et al. (1990) Annual Rev. Biochem. 59:439-473.

An "antigen-binding site," or "binding portion" of an antibody, refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

A binding agent may be, for example, a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. Monoclonal antibodies specific for a polypeptide of interest may be prepared, for example, using the technique of Kohler and Milstein, *Eur. J. Immunol.* 6:511-519, 1976, and improvements thereto. The polypeptides of this invention may be used in the purification process in, for example, an affinity chromatography step.

An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H::V_L$ heterodimer including an antigen-binding site which retains much of the antigen recognition and binding capabilities of the native antibody molecule. Inbar et al. (1972) *Proc. Nat. Acad. Sci.* USA 69:2659-2662; Hochman et al. (1976) *Biochem* 15:2706-2710; and Ehrlich et al. (1980) *Biochem* 19:4091-4096.

A single chain Fv ("sFv") polypeptide is a covalently linked $V_H::V_L$ heterodimer which is expressed from a gene fusion including $V_H$- and $V_L$-encoding genes linked by a peptide-encoding linker. Huston et al. (1988) Proc. Nat. Acad. Sci. USA 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349:293-299; Lobuglio et al. (1989) Proc. Nat. Acad. Sci. USA 86:4220-4224; Shaw et al. (1987) J Immunol. 138:4534-4538; and Brown et al. (1987) Cancer Res. 47:3577-3583), rodent CDRs grafted into a human supporting FR prior to fusion with an appropriate human antibody constant domain (Riechmann et al. (1988) Nature 332:323-327; Verhoeyen et al. (1988) Science 239:1534-1536; and Jones et al. (1986) Nature 321:522-525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

As noted above, "peptides" are included as binding agents. The term peptide typically refers to a polymer of amino acid residues and to variants and synthetic analogues of the same. In certain embodiments, the term "peptide" refers to relatively short polypeptides, including peptides that consist of about 2, 3, 4, 5, 6, 7, 8, 9, 10, 11, 12, 13, 14, 15, 16, 17, 18, 19, 20, 25, 30, 35, 40, 45, or 50 amino acids, including all integers and ranges (e.g., 5-10, 8-12, 10-15) in between, and interact with an AspRS polypeptide, its cellular binding partner, or both. Peptides can be composed of naturally-occurring amino acids and/or non-naturally occurring amino acids, as described herein.

A binding agent may include a peptide mimetic or other small molecule. A "small molecule" refers to an organic compound that is of synthetic or biological origin (biomolecule), but is typically not a polymer. Organic compounds refer to a large class of chemical compounds whose molecules contain carbon, typically excluding those that contain only carbonates, simple oxides of carbon, or cyanides. A "biomolecule" refers generally to an organic molecule that is produced by a living organism, including large polymeric molecules (biopolymers) such as peptides, polysaccharides, and nucleic acids as well, and small molecules such as primary secondary metabolites, lipids, phospholipids, glycolipids, sterols, glycerolipids, vitamins, and hormones. A "polymer" refers generally to a large molecule or macromolecule composed of repeating structural units, which are typically connected by covalent chemical bond.

In certain embodiments, a small molecule has a molecular weight of less than 1000 Daltons, typically between about 300 and 700 Daltons, and including about 50, 100, 150, 200, 250, 300, 350, 400, 450, 500, 550, 500, 650, 600, 750, 700, 850, 800, 950, or 1000 Daltons.

Aptamers are also included as binding agents. Examples of aptamers included nucleic acid aptamers (e.g., DNA aptamers, RNA aptamers) and peptide aptamers. Nucleic acid aptamers refer generally to nucleic acid species that have been engineered through repeated rounds of in vitro selection or equivalent method, such as SELEX (systematic evolution of ligands by exponential enrichment), to bind to various molecular targets such as small molecules, proteins, nucleic acids, and even cells, tissues and organisms. Hence, included are nucleic acid aptamers that bind to the AspRS polypeptides described herein and/or their cellular binding partners.

Peptide aptamers typically include a variable peptide loop attached at both ends to a protein scaffold, a double structural constraint that typically increases the binding affinity of the peptide aptamer to levels comparable to that of an antibody's (e.g., in the nanomolar range). In certain embodiments, the variable loop length may be composed of about 10-20 amino acids (including all integers in between), and the scaffold may include any protein that has good solubility and compacity properties. Certain exemplary embodiments may utilize the bacterial protein Thioredoxin-A as a scaffold protein, the variable loop being inserted within the reducing active site (-Cys-Gly-Pro-Cys- loop in the wild protein), with the two cysteines lateral chains being able to form a disulfide bridge. Hence, included are peptide aptamers that bind to the AspRS polypeptides described herein and/or their cellular binding partners. Peptide aptamer selection can be performed using different systems known in the art, including the yeast two-hybrid system.

As noted above, the AspRS polypeptides and binding agents of the present invention can be used in any of the diagnostic, drug discovery, or therapeutic methods described herein.

In another embodiment of the invention, binding agents such as monoclonal antibodies of the present invention may be coupled to one or more agents of interest. For example, a therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used.

Formulation and Administration

The compositions of the invention (e.g., polypeptides, polynucleotides, antibodies, etc.) are generally formulated in pharmaceutically-acceptable or physiologically-acceptable solutions for administration to a cell, tissue or animal, either alone, or in combination with one or more other modalities of therapy. It will also be understood that, if desired, the compositions of the invention may be administered in combination with other agents as well, such as, e.g., other proteins or polypeptides or various pharmaceutically-active agents. There is virtually no limit to other components that may also be included in the compositions, provided that the additional agents do not adversely affect the desired effects desired to be achieved with an AspRS polypeptide of the invention.

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intracranial and intramuscular administration and formulation.

In certain applications, the pharmaceutical compositions disclosed herein may be delivered via oral administration to a subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein parenterally, intravenously, intramuscularly, or even intraperitoneally as described, for example, in U.S. Pat. Nos. 5,543,158; 5,641,515 and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., Remington's Pharmaceutical Sciences, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the pharmaceutical compositions may be delivered by intranasal sprays, inhalation, and/or other aerosol delivery vehicles. Methods for delivering genes, polynucleotides, and peptide compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

Kits Comprising Compositions of the Invention

The invention, in other aspects, provides kits comprising one or more containers filled with one or more of the polypeptides, polynucleotides, antibodies, multiunit complexes, compositions thereof, etc., of the invention, as described herein. The kits can include written instructions on how to use such compositions (e.g., to modulate cellular signaling, angiogenesis, cancer, inflammatory conditions, etc.).

The kits herein may also include a one or more additional therapeutic agents or other components suitable or desired for the indication being treated. An additional therapeutic agent may be contained in a second container, if desired. Examples of additional therapeutic agents include, but are not limited to antineoplastic agents, anti-inflammatory agents, antibacterial agents, antiviral agents, angiogenic agents, etc.

The kits herein can also include one or more syringes or other components necessary or desired to facilitate an intended mode of delivery (e.g., stents, implantable depots, etc.).

Methods of Use

Embodiments of the present invention also include methods of using the AspRS compositions or "agents" described herein for diagnostic, drug discovery, and/or therapeutic purposes. The term AspRS "agents" refers generally to the AspRS polynucleotides, AspRS polypeptides, binding agents, and other compounds described herein. For diagnostic purposes, the AspRS agents can be used in a variety of non-limiting ways, such as to distinguish between different cell types or different cellular states, or to identify subjects having a relevant disease or condition. For drug discovery purposes, the AspRS agents can be used to identify one or more cellular "binding partners" of an AspRS polypeptide, characterize one or more "non-canonical" activities of an AspRS polypeptide, identify agents that selectively or non-selectively agonize or antagonize the interaction of an AspRS polypeptide with its binding partner(s), and/or identify agents that selectively or non-selectively agonize or antagonize one or more "non-canonical" activities of an AspRS polypeptide. For therapeutic purposes, the AspRS agents or compositions provided herein can be used to treat a variety of diseases or conditions, detailed below.

A. Diagnostics

As noted above, AspRS agents described herein can be used in diagnostic assays. These embodiments include the detection of the AspRS polynucleotide sequence(s) or corresponding polypeptide sequence(s) or portions thereof of one or more newly identified AspRS protein fragments. In certain embodiments, the presence or levels of one or more newly identified AspRS sequences associates or correlates with one or more cellular types or cellular states. Hence, as noted above, the presence or levels of an AspRS sequence can be used to distinguish between different cellular types or different cellular states. The presence or levels of AspRS sequences can be detected according to polynucleotide and/or polypeptide-based diagnostic techniques.

Certain of the methods provided herein rely on the differential expression of an AspRS sequence to characterize the condition or state of a cell, tissue, or subject, and to distinguish it from another cell, tissue, or subject. Non-limiting examples include methods of detecting the presence or levels of an AspRS sequence in a biological sample to distinguish between cells or tissues of different species, cells of different tissues or organs, cellular developmental states such as neonatal and adult, cellular differentiation states, conditions such as healthy, diseased and treated, intracellular and extracellular fractions, in addition to primary cell cultures and other cell cultures, such as immortalized cell cultures.

Differential expression refers generally to a statistically significant difference in one or more gene expression levels of an AspRS polynucleotide or polypeptide sequence compared to the expression levels of the same sequence in an appropriate control. The statistically significant difference may relate to either an increase or a decrease in expression levels, as measured by RNA levels, protein levels, protein function, or any other relevant measure of gene expression such as those described herein.

A result is typically referred to as statistically significant if it is unlikely to have occurred by chance. The significance level of a test or result relates traditionally to a frequentist statistical hypothesis testing concept. In simple cases, statistical significance may be defined as the probability of making a decision to reject the null hypothesis when the null hypothesis is actually true (a decision known as a Type I error, or "false positive determination"). This decision is often made using the p-value: if the p-value is less than the significance level, then the null hypothesis is rejected. The smaller the p-value, the more significant the result. Bayes factors may also be utilized to determine statistical significance (see, e.g., Goodman S., *Ann Intern Med* 130:1005-13, 1999).

In more complicated, but practically important cases, the significance level of a test or result may reflect an analysis in which the probability of making a decision to reject the null hypothesis when the null hypothesis is actually true is no more than the stated probability. This type of analysis allows for those applications in which the probability of deciding to reject may be much smaller than the significance level for some sets of assumptions encompassed within the null hypothesis.

In certain exemplary embodiments, statistically significant differential expression may include situations wherein the expression level of a given AspRS sequence provides at least about a 1.2×, 1.3×, 1.4×, 1.5×, 1.6×, 1.7×, 1.8×, 1.9×. 2.0×, 2.2×, 2.4×, 2.6×, 2.8×, 3.0×, 4.0×, 5.0×, 6.0×, 7.0×, 8.0×, 9.0×, 10.0×, 15.0×, 20.0×, 50.0×, 100.0×, or greater difference in expression (i.e., differential expression that may be higher or lower expression) in a suspected biological sample as compared to an appropriate control, including all integers and decimal points in between (e.g., 1.24×, 1.25×, 2.1×, 2.5×, 60.0×, 75.0×, etc.). In certain embodiments, statistically significant differential expression may include situations wherein the expression level of a given AspRS sequence provides at least about 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000 percent (%) or greater difference in expression (i.e., differential expression that may be higher or lower) in a suspected biological sample as compared to an appropriate control, including all integers and decimal points in between.

As an additional example, differential expression may also be determined by performing Z-testing, i.e., calculating an absolute Z score, as described herein and known in the art (see Example 1). Z-testing is typically utilized to identify significant differences between a sample mean and a population mean. For example, as compared to a standard normal table (e.g., a control tissue), at a 95% confidence interval (i.e., at the 5% significance level), a Z-score with an absolute value greater than 1.96 indicates non-randomness. For a 99% confidence interval, if the absolute Z is greater than 2.58, it means that p<0.01, and the difference is even more significant—the null hypothesis can be rejected with greater confidence. In these and related embodiments, an absolute Z-score of 1.96, 2, 2.58, 3, 4, 5, 6, 7, 8, 9, 10, 11, 12, 13, 14, 15, 16, 17, 18, 19, 20 or more, including all decimal points in between (e.g., 10.1, 10.6, 11.2, etc.), may provide a strong measure of statistical significance. In certain embodiments, an absolute Z-score of greater than 6 may provide exceptionally high statistical significance.

Substantial similarly relates generally to the lack of a statistically significant difference in the expression levels between the biological sample and the reference control. Examples of substantially similar expression levels may include situations wherein the expression level of a given SSCIGS provides less than about a 0.05×, 0.1×, 0.2×, 0.3×, 0.4×, 0.5×, 0.6×, 0.7×, 0.8×, 0.9×. 1.0×, 1.1×, 1.2×, 1.3×, or 1.4× difference in expression (i.e., differential expression that may be higher or lower expression) in a suspected biological sample as compared to a reference sample, including all decimal points in between (e.g., 0.15×, 0.25×, 0.35×, etc.). In certain embodiments, differential expression may include situations wherein the expression level of a given AspRS sequence provides less than about 0.25. 0.5, 1, 2, 3, 4, 5, 6, 7, 8, 9, 10, 11, 12, 13, 14, 15, 16, 17, 18, 19, 20, 30, 40, 50 percent (%) difference in expression (i.e., differential expression that may be higher or lower) in a suspected biological sample as compared to a reference sample, including all decimal points in between.

In certain embodiments, such as when using an Affymetrix Microarray to measure the expression levels of an AspRS polynucleotide or polypeptide sequence, differential expression may also be determined by the mean expression value summarized by Affymetrix Microarray Suite 5 software (Affymetrix, Santa Clara, Calif.), or other similar software, typically with a scaled mean expression value of 1000.

Embodiments of the present invention include methods of detecting the presence or levels of an AspRS polynucleotide or polypeptide reference sequence or a portion thereof to distinguish between cells, tissues, or other biological samples of a different organism or species, wherein the presence or levels of that sequence associates with a selected organism or species. General examples include methods of distinguishing between humans and any combination of bacteria, fungi, plants, and other non-human animals. Included within animals are methods of distinguishing between humans and any combination of vertebrates and invertebrates, including vertebrates such as fish, amphibians, reptiles, birds, and non-human mammals, and invertebrates such as insects, mollusks, crustaceans, and corals. Included within non-human mammals are methods of distinguishing between humans and any combination of non-human mammals from the Order Afrosoricida, Macroscelidea, Tubulidentata, Hyracoidea, Proboscidea, Sirenia, Cingulata, Pilosa, Scandentia, Dermoptera, Primates, Rodentia, Lagomorpha, Erinaceomorpha, Soricomorpha, Chiroptera, Pholidota, Cetacea, Carnivora, Perissodactyla, or Artiodactyla. Included within the Primate Order are monkeys, apes, gorillas, and chimpanzees, among others known in the art. Accordingly, the presence or levels of an AspRS polynucleotide or polypeptide reference sequence or variant, as described herein, may be used to identify the source of a given biological sample, such as a cell, tissue, or organ, by distinguishing between any combination of these organisms, or by distinguishing between humans and any one or more of these organisms, such as a panel of organisms. In certain embodiments, the source of a given biological sample may also be determined by comparing the presence or levels of an AspRS sequence or a portion thereof to a pre-determined value.

Embodiments of the present invention include methods of detecting the presence or levels of an AspRS polynucleotide or polypeptide reference sequence or a portion thereof to distinguish between cells or other biological samples that originate from different tissues or organs. Non-limiting examples include methods of distinguishing between a cell or other biological sample that originates from any combination of skin (e.g., dermis, epidermis, subcutaneous layer), hair follicles, nervous system (e.g., brain, spinal cord, peripheral nerves), auditory system or balance organs (e.g., inner ear, middle ear, outer ear), respiratory system (e.g., nose, trachea, lungs), gastroesophogeal tissues, the gastrointestinal system (e.g., mouth, esophagus, stomach, small intestines, large intestines, rectum), vascular system (e.g., heart, blood vessels and arteries), liver, gallbladder, lymphatic/immune system (e.g., lymph nodes, lymphoid follicles, spleen, thymus, bone marrow), uro-genital system (e.g., kidneys, ureter, bladder, urethra, cervix, Fallopian tubes, ovaries, uterus, vulva, prostate, bulbourethral glands, epidiymis, prostate, seminal vesicles, testicles), musculoskeletal system (e.g., skeletal muscles, smooth muscles, bone, cartilage, tendons, ligaments), adipose tissue, mammaries, and the endocrine system (e.g., hypothalamus, pituitary, thyroid, pancreas, adrenal glands). Hence, based on the association of an AspRS polynucleotide or polypeptide sequence as described herein, these methods may be used to identify or characterize the tissue or organ from which a cell or other biological sample is derived.

Embodiments of the present invention include methods of detecting the presence or levels of an AspRS polynucleotide or polypeptide reference sequence or a portion thereof to distinguish between or characterize the developmental or differentiation state of the cell. Also included are methods of differentiating between germ cells, stem cells, and somatic cells. Examples of developmental states include neonatal and adult. Examples of cellular differentiation states include all of the discreet and identifiable stages between a totipotent cell, a pluripotent cell, a multipotent progenitor stem cell and a mature, fully differentiated cell.

A totipotent cell has total potential, typically arises during sexual and asexual reproduction, and includes and spores and zygotes, though in certain instances cells can dedifferentiate and regain totipotency. A pluripotent cell includes a stem cell that has the potential to differentiate into any of the three germ layers, including the endoderm (interior stomach lining, gastrointestinal tract, the lungs), the mesoderm (muscle, bone, blood, urogenital), and the ectoderm (epidermal tissues and nervous system). Multipotent progenitor cells are typically capable of differentiating into a limited number of tissue types. Examples of multipotent cells include, without limitation, hematopoietic stem cells (adult stem cells) from the bone marrow that give rise to immune cells such as red blood cells, white blood cells, and platelets, mesenchymal stem cells (adult stem cells) from the bone marrow that give rise to stromal cells, fat cells, and various types of bone cells, epithelial stem cells (progenitor cells) that give rise to the various types of skin cells, and muscle satellite cells (progenitor cells) that contribute to differentiated muscle tissue. Accordingly, the presence or levels of particular AspRS polynucleotide or polypeptide sequence can be used to distinguish between or characterize the above-noted cellular differentiation states, as compared to a control or a predetermined level.

Embodiments of the present invention include methods of detecting the presence or levels of an AspRS polynucleotide or polypeptide reference sequence to characterize or diagnose the condition or a cell, tissue, organ, or subject, in which that condition may be characterized as healthy, diseased, at risk for being diseased, or treated. For such diagnostic purposes, the term "diagnostic" or "diagnosed" includes identifying the presence or nature of a pathologic condition, characterizing the risk of developing such a condition, and/or measuring the change (or no change) of a pathologic condition in response to therapy. Diagnostic methods may differ in their sensitivity and specificity. In certain embodiments, the "sensitivity" of a diagnostic assay refers to the percentage of diseased cells, tissues or subjects which test positive (percent of "true positives"). Diseased cells, tissues or subjects not detected by the assay are typically referred to as "false negatives." Cells, tissues or subjects that are not diseased and which test negative in the assay may be termed "true negatives." In certain embodiments, the "specificity" of a diagnostic assay may be defined as one (1) minus the false positive rate, where the "false positive" rate is defined as the proportion of those samples or subjects without the disease and which test positive. While a particular diagnostic method may not provide a definitive diagnosis of a condition, it suffices if the method provides a positive indication that aids in diagnosis.

In certain instances, the presence or risk of developing a pathologic condition can be diagnosed by comparing the presence or levels of one or more selected AspRS polynucleotide or polypeptide reference sequences or portions thereof that correlate with the condition, whether by increased or decreased levels, as compared to a suitable control. A "suitable control" or "appropriate control" includes a value, level, feature, characteristic, or property determined in a cell or other biological sample of a tissue or organism, e.g., a control or normal cell, tissue or organism, exhibiting, for example, normal traits, such as the absence of the condition. In certain embodiments, a "suitable control" or "appropriate control" is a predefined value, level, feature, characteristic, or property. Other suitable controls will be apparent to persons skilled in the art. Examples of diseases and conditions are described elsewhere herein.

Embodiments of the present invention include AspRS polynucleotide or nucleic acid-based detection techniques, which offer certain advantages due to sensitivity of detection. Hence, certain embodiments relate to the use or detection of AspRS polynucleotides as part of a diagnostic method or assay. The presence and/or levels of AspRS polynucleotides may be measured by any method known in the art, including hybridization assays such as Northern blot, quantitative or qualitative polymerase chain reaction (PCR), quantitative or qualitative reverse transcriptase PCR (RT-PCR), microarray, dot or slot blots, or in situ hybridization such as fluorescent in situ hybridization (FISH), among others. Certain of these methods are described in greater detail below.

AspRS polynucleotides such as DNA and RNA can be collected and/or generated from blood, biological fluids, tissues, organs, cell lines, or other relevant sample using techniques known in the art, such as those described in Kingston. (2002 *Current Protocols in Molecular Biology*, Greene Publ. Assoc. Inc. & John Wiley & Sons, Inc., NY, N.Y. (see, e.g., as described by Nelson et al. *Proc Natl Acad Sci USA,* 99: 11890-11895, 2002) and elsewhere.

Complementary DNA (cDNA) libraries can be generated using techniques known in the art, such as those described in Ausubel et al. (2001 *Current Protocols in Molecular Biology*, Greene Publ. Assoc. Inc. & John Wiley & Sons, Inc., NY, N.Y.); Sambrook et al. (1989 *Molecular Cloning*, Second Ed., Cold Spring Harbor Laboratory, Plainview, N.Y.); Maniatis et al. (1982 *Molecular Cloning*, Cold Spring Harbor Laboratory, Plainview, N.Y.) and elsewhere.

Certain embodiments may employ hybridization methods for detecting AspRS polynucleotide sequences. Methods for conducting polynucleotide hybridization assays have been well developed in the art. Hybridization assay procedures and conditions will vary depending on the application and are selected in accordance with the general binding methods known including those referred to in: Maniatis et al. Molecular Cloning: A Laboratory Manual (2nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davism, P.N.A.S, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference Certain embodiments may employ nucleic acid amplification methods for detecting AspRS polynucleotide sequences. The term "amplification" or "nucleic acid amplification" refers to the production of multiple copies of a target nucleic acid that contains at least a portion of the intended specific target nucleic acid sequence. The multiple copies may be referred to as amplicons or amplification products. In certain embodiments, the amplified target contains less than the complete target gene sequence (introns and exons) or an expressed target gene sequence (spliced transcript of exons and flanking untranslated sequences). For example, specific amplicons may be produced by amplifying a portion of the target polynucleotide by using amplification primers that hybridize to, and initiate polymerization from, internal positions of the target polynucleotide. Preferably, the amplified portion contains a detectable target sequence that may be detected using any of a variety of well-known methods.

"Selective amplification" or "specific amplification," as used herein, refers to the amplification of a target nucleic acid sequence according to the present invention wherein detectable amplification of the target sequence is substantially limited to amplification of target sequence contributed by a nucleic acid sample of interest that is being tested and is not contributed by target nucleic acid sequence contributed by some other sample source, e.g., contamination present in reagents used during amplification reactions or in the environment in which amplification reactions are performed.

By "amplification conditions" is meant conditions permitting nucleic acid amplification according to the present invention. Amplification conditions may, in some embodiments, be less stringent than "stringent hybridization conditions" as described herein. Oligonucleotides used in the amplification reactions of the present invention hybridize to their intended targets under amplification conditions, but may or may not hybridize under stringent hybridization conditions. On the other hand, detection probes of the present invention typically hybridize under stringent hybridization conditions. Acceptable conditions to carry out nucleic acid amplifications according to the present invention can be easily ascertained by someone having ordinary skill in the art depending on the particular method of amplification employed.

Many well-known methods of nucleic acid amplification require thermocycling to alternately denature double-stranded nucleic acids and hybridize primers; however, other well-known methods of nucleic acid amplification are isothermal. The polymerase chain reaction (U.S. Pat. Nos. 4,683,195; 4,683,202; 4,800,159; 4,965,188), commonly referred to as PCR, uses multiple cycles of denaturation, annealing of primer pairs to opposite strands, and primer extension to exponentially increase copy numbers of the target sequence. In a variation called RT-PCR, reverse transcriptase (RT) is used to make a complementary DNA (cDNA) from mRNA, and the cDNA is then amplified by PCR to produce multiple copies of DNA.

As noted above, the term "PCR" refers to multiple amplification cycles that selectively amplify a target nucleic acid species. Included are quantitative PCR (qPCR), real-time PCR (RT-PCR), reverse transcription PCR (RT-PCR) and quantitative reverse transcription PCR (qRT-PCR) is well described in the art. The term "pPCR" refers to quantitative polymerase chain reaction, and the term "qRT-PCR" refers to quantitative reverse transcription polymerase chain reaction. qPCR and qRT-PCR may be used to amplify and simultaneously quantify a targeted cDNA molecule. It enables both detection and quantification of a specific sequence in a cDNA pool, such as a selected AspRS gene or transcript.

The term "real-time PCR" may use DNA-binding dye to bind to all double-stranded (ds) DNA in PCR, causing fluorescence of the dye. An increase in DNA product during PCR therefore leads to an increase in fluorescence intensity and is measured at each cycle, thus allowing DNA concentrations to be quantified. However, dsDNA dyes such as SYBR Green will bind to all dsDNA PCR products. Fluorescence is detected and measured in the real-time PCR thermocycler, and its geometric increase corresponding to exponential increase of the product is used to determine the threshold cycle ("Ct") in each reaction.

The term "Ct Score" refers to the threshold cycle number, which is the cycle at which PCR amplification has surpassed a threshold level. If there is a higher quantity of mRNA for a particular gene in a sample, it will cross the threshold earlier than a lowly expressed gene since there is more starting RNA to amplify. Therefore, a low Ct score indicates high gene expression in a sample and a high Ct score is indicative of low gene expression.

Certain embodiments may employ the ligase chain reaction (Weiss, R. 1991, Science 254: 1292), commonly referred to as LCR, which uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

In certain embodiments, other techniques may be used to evaluate RNA transcripts of the transcripts from a particular cDNA library, including microarray analysis (Han, M., et al., *Nat Biotechnol*, 19: 631-635, 2001; Bao, P., et al., *Anal Chem*, 74: 1792-1797, 2002; Schena et al., *Proc. Natl. Acad. Sci.* USA 93:10614-19, 1996; and Heller et al., *Proc. Natl. Acad. Sci.* USA 94:2150-55, 1997) and SAGE (serial analysis of gene expression). Like MPSS, SAGE is digital and can generate a large number of signature sequences. (see e.g., Velculescu, V. E., et al., *Trends Genet*, 16: 423-425, 2000; Tuteja R. and Tuteja N. *Bioassays*. 2004 August; 26(8):916-22), although orders of magnitude fewer than that are available from techniques such as MPSS.

In certain embodiments, the term "microarray" includes a "nucleic acid microarray" having a substrate-bound plurality of nucleic acids, hybridization to each of the plurality of bound nucleic acids being separately detectable. The substrate can be solid or porous, planar or non-planar, unitary or distributed. Nucleic acid microarrays include all the devices so called in Schena (ed.), DNA Microarrays: A Practical Approach (Practical Approach Series), Oxford University Press (1999); Nature Genet. 21(1) (suppl.): 1-60 (1999); Schena (ed.), Microarray Biochip: Tools and Technology, Eaton Publishing Company/BioTechniques Books Division (2000). Nucleic acid microarrays may include a substrate-bound plurality of nucleic acids in which the plurality of nucleic acids are disposed on a plurality of beads, rather than on a unitary planar substrate, as described, for example, in Brenner et al., *Proc. Natl. Acad. Sci.* USA 97(4): 1665-1670 (2000). Examples of nucleic acid microarrays may be found in U.S. Pat. Nos. 6,391,623, 6,383,754, 6,383,749, 6,380,377, 6,379,897, 6,376,191, 6,372,431, 6,351,712 6,344,316, 6,316,193, 6,312,906, 6,309,828, 6,309,824, 6,306,643, 6,300,063, 6,287,850, 6,284,497, 6,284,465, 6,280,954, 6,262,216, 6,251,601, 6,245,518, 6,263,287, 6,251,601, 6,238,866, 6,228,575, 6,214,587, 6,203,989, 6,171,797, 6,103,474, 6,083,726, 6,054,274, 6,040,138, 6,083,726, 6,004,755, 6,001,309, 5,958,342, 5,952,180, 5,936,731, 5,843,655, 5,814,454, 5,837,196, 5,436,327, 5,412,087, and 5,405,783, the disclosures of which are incorporated by reference.

Additional examples include nucleic acid arrays that are commercially available from Affymetrix (Santa Clara, Calif.) under the brand name GeneChip™. Further exemplary methods of manufacturing and using arrays are provided in, for example, U.S. Pat. Nos. 7,028,629; 7,011,949; 7,011,945; 6,936,419; 6,927,032; 6,924,103; 6,921,642; and 6,818,394.

The present invention as related to arrays and microarrays also contemplates many uses for polymers attached to solid substrates. These uses include gene expression monitoring, profiling, library screening, genotyping and diagnostics. Gene expression monitoring and profiling methods and methods useful for gene expression monitoring and profiling are shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598 (U.S. Application No. 2003/0036069), and U.S. Pat. Nos. 5,925,525, 6,268,141, 5,856,092, 6,267,152, 6,300,063, 6,525,185, 6,632,611, 5,858,659, 6,284,460, 6,361,947, 6,368,799, 6,673,579 and 6,333,179. Other methods of nucleic acid amplification, labeling and analysis that may be used in combination with the methods disclosed herein are embodied in U.S. Pat. Nos. 5,871,928, 5,902,723, 6,045,996, 5,541,061, and 6,197,506.

As will be apparent to persons skilled in the art, certain embodiments may employ oligonucleotides, such as primers or probes, for amplification or detection, as described herein. While the design and sequence of oligonucleotides depends on their function as described herein, several variables are generally taken into account. Among the most relevant are: length, melting temperature (Tm), specificity, complementarity with other oligonucleotides in the system, G/C content, polypyrimidine (T, C) or polypurine (A, G) stretches, and the 3'-end sequence.

Certain embodiments therefore include methods for detecting a target AspRS polynucleotide in a sample, typically wherein the polynucleotide comprises the sequence of a reference AspRS polynucleotide described herein, comprising a) hybridizing the sample with a probe comprising a sequence complementary to the target polynucleotide in the sample, and which probe specifically hybridizes to said target polynucleotide, under conditions whereby a hybridization complex is formed between said probe and said target polynucleotide or fragments thereof, and b) detecting the presence or absence of said hybridization complex, and optionally, if present, the amount thereof. Also included are methods for detecting a target AspRS polynucleotide in a sample, the polynucleotide comprising the sequence of a reference AspRS polynucleotide, as described herein, comprising a) amplifying the target polynucleotide or fragment thereof, and b) detecting the presence or absence of said amplified target polynucleotide or fragment thereof, and, optionally, if present, the amount thereof.

Embodiments of the present invention include a variety of AspRS polypeptide-based detection techniques, including antibody-based detection techniques. Included in these embodiments are the use of AspRS polypeptides to generate antibodies or other binders, which may then be used in diagnostic methods and compositions to detect or quantitate selected AspRS polypeptides in a cell or other biological sample, typically from a subject.

Certain embodiments may employ standard methodologies such as western blotting and immunoprecipitation, enzyme-linked immunosorbent assays (ELISA), flow cytometry, and immunofluorescence assays (IFA). These well-known methods typically utilize one or more monoclonal or polyclonal antibodies as described herein that specifically bind to a selected AspRS polypeptide of the invention, or a unique region of that AspRS polypeptide, and generally do not bind significantly to other AspRS polypeptides, such as a full-length AspRS polypeptide. In certain embodiments, the unique region of the AspRS polypeptide may be encoded by a unique splice junction or a particular three-dimensional structure of a newly identified alternate splice variant or protein fragment, such as a proteolytic fragment.

Certain embodiments may employ "arrays," such as "microarrays." In certain embodiments, a "microarray" may also refer to a "peptide microarray" or "protein microarray" having a substrate-bound collection or plurality of polypeptides, the binding to each of the plurality of bound polypeptides being separately detectable. Alternatively, the peptide microarray may have a plurality of binders, including but not limited to monoclonal antibodies, polyclonal antibodies, phage display binders, yeast 2 hybrid binders, and aptamers, which can specifically detect the binding of the AspRS polypeptides described herein. The array may be based on autoantibody detection of these AspRS polypeptides, as described, for example, in Robinson et al., *Nature Medicine* 8(3):295-301 (2002). Examples of peptide arrays may be found in WO 02/31463, WO 02/25288, WO 01/94946, WO 01/88162, WO 01/68671, WO 01/57259, WO 00/61806, WO 00/54046, WO 00/47774, WO 99/40434, WO 99/39210, and WO 97/42507 and U.S. Pat. Nos. 6,268,210, 5,766,960, and 5,143,854, each of which are incorporated by reference.

Certain embodiments may employ MS or other molecular weight-based methods for diagnostically detecting AspRS polypeptide sequences. Mass spectrometry (MS) refers generally to an analytical technique for determining the elemental composition of a sample or molecule. MS may also be used for determining the chemical structures of molecules, such as peptides and other chemical compounds.

Generally, the MS principle consists of ionizing chemical compounds to generate charged molecules or molecule fragments, and then measuring their mass-to-charge ratios. In an illustrative MS procedure: a sample is loaded onto the MS instrument, and undergoes vaporization, the components of the sample are ionized by one of a variety of methods (e.g., by impacting them with an electron beam), which results in the formation of positively charged particles, the positive ions are then accelerated by a magnetic field, computations are performed on the mass-to-charge ratio (m/z) of the particles based on the details of motion of the ions as they transit through electromagnetic fields, and, detection of the ions, which in step prior were sorted according to m/z.

An illustrative MS instruments has three modules: an ion source, which converts gas phase sample molecules into ions (or, in the case of electrospray ionization, move ions that exist in solution into the gas phase); a mass analyzer, which sorts the ions by their masses by applying electromagnetic fields; and a detector, which measures the value of an indicator quantity and thus provides data for calculating the abundances of each ion present.

The MS technique has both qualitative and quantitative uses, including identifying unknown compounds, determining the isotopic composition of elements in a molecule, and determining the structure of a compound by observing its fragmentation. Other uses include quantifying the amount of a compound in a sample or studying the fundamentals of gas phase ion chemistry (the chemistry of ions and neutrals in a vacuum). Accordingly, MS techniques may be used according to any of the methods provided herein to measure the presence or levels of an AspRS polypeptide of the invention in a biological sample, and to compare those levels to a control sample or a pre-determined value.

B. Discovery of Compounds and Therapeutic Agents

Certain embodiments relate to the use of AspRS polypeptide or AspRS polynucleotide references sequences in drug discovery, typically to identify agents that modulate one or more of the non-canonical activities of the reference AspRS. For example, certain embodiments include methods of identifying one or more "binding partners" of an AspRS reference polypeptide, or a polypeptide that comprises an AspRS reference sequence such as a cellular protein or other host molecule that associates with the AspRS polypeptide and participates in its non-canonical activity or activities. Also included are methods of identifying a compound (e.g., polypeptide) or other agent that agonizes or antagonizes the non-canonical activity of an AspRS reference polypeptide or active variant thereof, such as by interacting with the AspRS polypeptide and/or one or more of its cellular binding partners.

Certain embodiments therefore include methods of identifying a binding partner of an AspRS reference polypeptide, comprising a) combining the AspRS polypeptide with a biological sample under suitable conditions, and b) detecting specific binding of the AspRS polypeptide to a binding partner, thereby identifying a binding partner that specifically binds to the AspRS reference polypeptide. Also included are methods of screening for a compound that specifically binds to an AspRS reference polypeptide or a binding partner of the AspRS polypeptide, comprising a) combining the polypeptide or the binding partner with at least one test compound under suitable conditions, and b) detecting binding of the polypeptide or the binding partner to the test compound, thereby identifying a compound that specifically binds to the polypeptide or its binding partner. In certain embodiments, the compound is a polypeptide or peptide. In certain embodiments, the compound is a small molecule or other (e.g., non-biological) chemical compound. In certain embodiments, the compound is a peptide mimetic.

Any method suitable for detecting protein-protein interactions may be employed for identifying cellular proteins that interact with an AspRS reference polypeptide, interact with one or more of its cellular binding partners, or both. Examples of traditional methods that may be employed include co-immunoprecipitation, cross-linking, and co-purification through gradients or chromatographic columns of cell lysates or proteins obtained from cell lysates, mainly to identify proteins in the lysate that interact with the AspRS polypeptide.

In these and related embodiments, at least a portion of the amino acid sequence of a protein that interacts with an AspRS polypeptide or its binding partner can be ascertained using techniques well known to those of skill in the art, such as via the Edman degradation technique. See, e.g., Creighton Proteins: Structures and Molecular Principles, W. H. Freeman & Co., N.Y., pp. 34 49, 1983. The amino acid sequence obtained may be used as a guide for the generation of oligonucleotide mixtures that can be used to screen for gene sequences encoding such proteins. Screening may be accomplished, for example, by standard hybridization or PCR techniques, as described herein and known in the art. Techniques for the generation of oligonucleotide mixtures and the screening are well known. See, e.g., Ausubel et al. Current Protocols in Molecular Biology Green Publishing Associates and Wiley Interscience, N.Y., 1989; and Innis et al., eds. PCR Protocols: A Guide to Methods and Applications Academic Press, Inc., New York, 1990.

Additionally, methods may be employed in the simultaneous identification of genes that encode the binding partner or other polypeptide. These methods include, for example, probing expression libraries, in a manner similar to the well known technique of antibody probing of lambda-gt11 libraries, using labeled AspRS protein, or another polypeptide, peptide or fusion protein, e.g., a variant AspRS polypeptide or AspRS domain fused to a marker (e.g., an enzyme, fluor, luminescent protein, or dye), or an Ig-Fc domain.

One method that detects protein interactions in vivo is the two-hybrid system. An example of this system has been described (Chien et al., PNAS USA 88:9578 9582, 1991) and is commercially available from Clontech (Palo Alto, Calif.). In certain instances, the two-hybrid system or other such methodology may be used to screen activation domain libraries for proteins that interact with the "bait" gene product. By way of example, and not by way of limitation, an AspRS reference polypeptide or variant may be used as the bait gene product. An AspRS binding partner may also be used as a "bait" gene product. Total genomic or cDNA sequences are fused to the DNA encoding an activation domain. This library and a plasmid encoding a hybrid of a bait AspRS gene product fused to the DNA-binding domain are co-transformed into a yeast reporter strain, and the resulting transformants are screened for those that express the reporter gene.

Also included are three-hybrid systems, which allow the detection of RNA-protein interactions in yeast. See, e.g., Hook et al., RNA. 11:227-233, 2005. Accordingly, these and related methods can be used to identify a cellular binding partner of an AspRS polypeptide. These and related methods can also be used to identify other compounds such as binding agents or nucleic acids that interact with the AspRS polypeptide, its cellular binding partner, or both.

As noted above, once isolated, binding partners can be identified and can, in turn, be used in conjunction with standard techniques to identify proteins or other compounds with which it interacts. Certain embodiments thus relate to methods of screening for a compound that specifically binds to the binding partner of an AspRS reference polypeptide, comprising a) combining the binding partner with at least one test compound under suitable conditions, and b) detecting binding of the binding partner to the test compound, thereby identifying a compound that specifically binds to the binding partner. In certain embodiments, the test compound is a polypeptide. In certain embodiments, the test compound is a chemical compound, such as a small molecule compound or peptide mimetic.

Certain embodiments include methods of screening for a compound that modulates the activity of an AspRS reference polypeptide, comprising a) combining the polypeptide with at least one test compound under conditions permissive for the activity of the polypeptide, b) assessing the activity of the polypeptide in the presence of the test compound, and c) comparing the activity of the polypeptide in the presence of the test compound with the activity of the polypeptide in the absence of the test compound, wherein a change in activity of the polypeptide in the presence of the test compound is indicative of a compound that modulates the activity of the polypeptide.

Certain embodiments include methods of screening for a compound that modulates the activity of a binding partner of an AspRS reference polypeptide, comprising a) combining the polypeptide with at least one test compound under conditions permissive for the activity of the binding partner, b) assessing the activity of the binding partner in the presence of the test compound, and c) comparing the activity of the binding partner in the presence of the test compound with the activity of the binding partner in the absence of the test compound, wherein a change in the activity of the binding partner in the presence of the test compound is indicative of a compound that modulates the activity of the binding partner. Typically, these and related embodiments include assessing a selected non-canonical activity that is associated with the AspRS polypeptide or its binding partner. Included are in vitro and in vivo conditions, such as cell culture conditions.

Certain embodiments include methods of screening a compound for effectiveness as a full or partial agonist of an AspRS reference polypeptide or an active fragment or variant thereof, comprising a) exposing a sample comprising the polypeptide to a compound, and b) detecting agonist activity in the sample, typically by measuring an increase in the non-canonical activity of the AspRS polypeptide. Certain methods include a) exposing a sample comprising a binding partner of the AspRS polypeptide to a compound, and b) detecting agonist activity in the sample, typically by measuring an increase in the selected non-canonical activity of the AspRS polypeptide. Certain embodiments include compositions that comprise an agonist compound identified by the method and a pharmaceutically acceptable carrier or excipient.

Also included are methods of screening a compound for effectiveness as a full or partial antagonist of an AspRS reference polypeptide, comprising a) exposing a sample comprising the polypeptide to a compound, and b) detecting antagonist activity in the sample, typically by measuring a decrease in the non-canonical activity of the AspRS polypeptide. Certain methods include a) exposing a sample comprising a binding partner of the AspRS polypeptide to a compound, and b) detecting antagonist activity in the sample, typically by measuring a decrease in the selected non-canonical activity of the AspRS polypeptide. Certain embodiments include compositions that comprise an antagonist compound identified by the method and a pharmaceutically acceptable carrier or excipient.

In certain embodiments, in vitro systems may be designed to identify compounds capable of interacting with or modulating an AspRS reference sequence or its binding partner. Certain of the compounds identified by such systems may be useful, for example, in modulating the activity of the pathway, and in elaborating components of the pathway itself. They may also be used in screens for identifying compounds that disrupt interactions between components of the pathway; or may disrupt such interactions directly. One exemplary approach involves preparing a reaction mixture of the AspRS polypeptide and a test compound under conditions and for a time sufficient to allow the two to interact and bind, thus forming a complex that can be removed from and/or detected in the reaction mixture In vitro screening assays can be conducted in a variety of ways. For example, an AspRS polypeptide, a cellular binding partner, or test compound(s) can be anchored onto a solid phase. In these and related embodiments, the resulting complexes may be captured and detected on the solid phase at the end of the reaction. In one example of such a method, the AspRS polypeptide and/or its binding partner are anchored onto a solid surface, and the test compound(s), which are not anchored, may be labeled, either directly or indirectly, so that their capture by the component on the solid surface can be detected. In other examples, the test compound(s) are anchored to the solid surface, and the AspRS polypeptide and/or its binding partner, which are not anchored, are labeled or in some way detectable. In certain embodiments, microtiter plates may conveniently be utilized as the solid phase. The anchored component (or test compound) may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

To conduct an exemplary assay, the non-immobilized component is typically added to the coated surface containing the anchored component. After the reaction is complete, un-reacted components are removed (e.g., by washing) under conditions such that any specific complexes formed will remain immobilized on the solid surface. The detection of complexes anchored on the solid surface can be accomplished in a number of ways. For instance, where previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, the presence or absence of binding of a test compound can be determined, for example, using surface plasmon resonance (SPR) and the change in the resonance angle as an index, wherein an AspRS polypeptide or a cellular binding partner is immobilized onto the surface of a commercially available sensorchip (e.g., manufactured by Biacore™) according to a conventional method, the test compound is contacted therewith, and the sensorchip is illuminated with a light of a particular wavelength from a particular angle. The binding of a test compound can also be measured by detecting the appearance of a peak corresponding to the test compound by a method wherein an AspRS polypeptide or a cellular binding partner is immobilized onto the surface of a protein chip adaptable to a mass spectrometer, a test compound is contacted therewith, and an ionization method such as MALDI-MS, ESI-MS, FAB-MS and the like is combined with a mass spectrometer (e.g., double-focusing mass spectrometer, quadrupole mass spectrometer, time-of-flight mass spectrometer, Fourier transformation mass spectrometer, ion cyclotron mass spectrometer and the like).

In certain embodiments, cell-based assays, membrane vesicle-based assays, or membrane fraction-based assays can be used to identify compounds that modulate interactions in the non-canonical pathway of the selected AspRS polypeptide. To this end, cell lines that express an AspRS polypeptide and/or a binding partner, or a fusion protein containing a domain or fragment of such proteins (or a combination thereof), or cell lines (e.g., COS cells, CHO cells, HEK293 cells, Hela cells etc.) that have been genetically engineered to express such protein(s) or fusion protein(s) can be used. Test compound(s) that influence the non-canonical activity can be identified by monitoring a change (e.g., a statistically significant change) in that activity as compared to a control or a predetermined amount.

For embodiments that relate to antisense and RNAi agents, for example, also included are methods of screening a compound for effectiveness in altering expression of an AspRS reference polynucleotide, comprising a) exposing a sample comprising the AspRS reference polynucleotide to a compound such as a potential antisense oligonucleotide, and b) detecting altered expression of the AspRS polynucleotide. In certain non-limiting examples, these and related embodiments can be employed in cell-based assays or in cell-free translation assays, according to routine techniques in the art. Also included are the antisense and RNAi agents identified by such methods.

Also included are any of the above methods, or other screening methods known in the art, which are adapted for high-throughput screening (HTS). HTS typically uses automation to run a screen of an assay against a library of candidate compounds, for instance, an assay that measures an increase or a decrease in a non-canonical activity, as described herein.

C. Methods of Treatment

In another aspect, the present invention relates to methods of using the compositions of the present invention for treating a cell, tissue or subject with a composition as described herein. The cells or tissue that may be modulated by the present invention are preferably mammalian cells, or more preferably human cells. Such cells can be of a healthy state or of a diseased state.

Accordingly, the AspRS agents described herein, including AspRS polypeptides, AspRS polynucleotides, AspRS polynucleotide-based vectors, antisense oligonucleotides, RNAi agents, as well as binding agents such as peptides, antibodies and antigen-binding fragments, peptide mimetics and other small molecules, can be used to treat a variety of non-limiting diseases or conditions associated with the non-canonical activities of a reference AspRS. Examples of such non-canonical activities include modulation of cell proliferation, modulation of cell migration, modulation of cell differentiation (e.g., hematopoiesis), modulation of apoptosis or other forms of cell death, modulation of cell signaling, modulation of angiogenesis, modulation of cell binding, modulation of cellular metabolism, modulation of cytokine production or activity, modulation of cytokine receptor activity, modulation of inflammation, and the like.

Included are polynucleotide-based therapies, such as antisense therapies and RNAi interference therapies, which typically relate to reducing the expression of a target molecule, such as a particular splice variant of an AspRS polypeptide or a cellular binding partner of an AspRS polypeptide, which otherwise contributes to its non-canonical activity. Antisense or RNAi therapies typically antagonize the non-canonical activity, such as by reducing expression of the AspRS reference polypeptide. Also included are polypeptides, antibodies, peptide mimetics, or other small molecule-based therapies, which either agonize or antagonize the non-canonical activity of an AspRS reference polypeptide, such as by interacting directly with the AspRS polypeptide, its cellular binding partner(s), or both.

In certain embodiments, for example, methods are provided for modulating therapeutically relevant cellular activities including, but not limited to, cellular metabolism, cell differentiation, cell proliferation, cell death, cell mobilization, cell migration, gene transcription, mRNA translation, cell impedance, cytokine production, and the like, comprising contacting a cell with an AspRS composition as described herein. Accordingly, the AspRS compositions may be employed in treating essentially any cell or tissue or subject that would benefit from modulation of one or more such activities.

The AspRS compositions may also be used in any of a number of therapeutic contexts including, for example, those relating to the treatment or prevention of neoplastic diseases, immune system diseases (e.g., autoimmunediseases and inflammation), infectious diseases, metabolic diseases, neuronal/neurological diseases, muscular/cardiovascular diseases, diseases associated with aberrant hematopoiesis, diseases associated with aberrant angiogenesis, diseases associated with aberrant cell survival, and others.

For example, in certain illustrative embodiments, the AspRS compositions of the invention may be used to modulate angiogenesis, e.g., via modulation of endothelial cell proliferation and/or signaling. Endothelial cell proliferation and/or cell signaling may be monitored using an appropriate cell line (e.g., Human microvascular endothelial lung cells (HMVEC-L) and Human umbilical vein endothelial cells (HUVEC)), and using an appropriate assay (e.g., endothelial cell migration assays, endothelial cell proliferation assays, tube-forming assays, matrigel plug assays, etc.), many of which are known and available in the art.

Therefore, in related embodiments, the compositions of the invention may be employed in the treatment of essentially any cell or tissue or subject that would benefit from modulation of angiogenesis. For example, in some embodiments, a cell or tissue or subject experiencing or susceptible to angiogenesis (e.g., an angiogenic condition) may be contacted with a suitable composition of the invention to inhibit an angiogenic condition. In other embodiments, a cell or tissue experiencing or susceptible to insufficient angiogenesis (e.g., an angiostatic condition) may be contacted with an appropriate composition of the invention in order to interfere with angiostatic activity and/or promote angiogenesis.

Illustrative examples of angiogenic conditions include, but are not limited to, age-related macular degeneration (AMD), cancer (both solid and hematologic), developmental abnormalities (organogenesis), diabetic blindness, endometriosis, ocular neovascularization, psoriasis, rheumatoid arthritis (RA), and skin discolorations (e.g., hemangioma, nevus flammeus or nevus simplex). Examples of anti-angiogenic conditions include, but are not limited to, cardiovascular disease, restenosis, tissue damage after reperfusion of ischemic tissue or cardiac failure, chronic inflammation and wound healing.

The compositions of the invention may also be useful as immunomodulators for treating anti- or pro-inflammatory indications by modulating the cells that mediate, either directly or indirectly, autoimmune and/or inflammatory disease, conditions and disorders. The utility of the compositions of the invention as immunomodulators can be monitored using any of a number of known and available techniques in the art including, for example, migration assays (e.g., using leukocytes or lymphocytes), cytokine production assays, or cell viability assays (e.g., using B-cells, T-cells, monocytes or NK cells).

"Inflammation" refers generally to the biological response of tissues to harmful stimuli, such as pathogens, damaged cells (e.g., wounds), and irritants. The term "inflammatory response" refers to the specific mechanisms by which inflammation is achieved and regulated, including, merely by way of illustration, immune cell activation or migration, cytokine production, vasodilation, including kinin release, fibrinolysis, and coagulation, among others described herein and known in the art. Ideally, inflammation is a protective attempt by the body to both remove the injurious stimuli and initiate the healing process for the affected tissue or tissues. In the absence of inflammation, wounds and infections would never heal, creating a situation in which progressive destruction of the tissue would threaten survival. On the other hand, excessive or chronic inflammation may associate with a variety of diseases, such as hay fever, atherosclerosis, and rheumatoid arthritis, among others described herein and known in the art.

Clinical signs of chronic inflammation are dependent upon duration of the illness, inflammatory lesions, cause and anatomical area affected. (see, e.g., Kumar et al., Robbins Basic Pathology-8$^{th}$ Ed., 2009 Elsevier, London; Miller, L M, Pathology Lecture Notes, Atlantic Veterinary College, Charlottetown, PEI, Canada). Chronic inflammation is associated with a variety of pathological conditions or diseases, including, for example, allergies, Alzheimer's disease, anemia, aortic valve stenosis, arthritis such as rheumatoid arthritis and osteoarthritis, cancer, congestive heart failure, fibromyalgia, fibrosis, heart attack, kidney failure, lupus, pancreatitis, stroke, surgical complications, inflammatory lung disease, inflammatory bowel disease, atherosclerosis, neurological disorders, diabetes, metabolic disorders, obesity, and psoriasis, among others described herein and known in the art. Hence, AspRS compositions may be used to treat or manage chronic inflammation, modulate any of one or more of the individual chronic inflammatory responses, or treat any one or more diseases or conditions associated with chronic inflammation.

Certain specific inflammatory responses include cytokine production and activity, and related pathways. For instance, certain exemplary embodiments relate to modulating cell-signaling through nuclear factor-kB (NF-kB), such as by increasing the downstream activities of this transcription factor. In certain instances, increases in NF-kB activity can lead to increases in cytokine signaling or activity, such as pro-inflammatory cytokines (e.g., TNF-α), and anti-inflammatory cytokines (e.g., IL-10).

Criteria for assessing the signs and symptoms of inflammatory and other conditions, including for purposes of making differential diagnosis and also for monitoring treatments such as determining whether a therapeutically effective dose has been administered in the course of treatment, e.g., by determining improvement according to accepted clinical criteria, will be apparent to those skilled in the art and are exemplified by the teachings of e.g., Berkow et al., eds., The Merck Manual, 16$^{th}$ edition, Merck and Co., Rahway, N.J., 1992; Goodman et al., eds., Goodman and Gilman's The Pharmacological Basis of Therapeutics, 10$^{th}$ edition, Pergamon Press, Inc., Elmsford, N.Y., (2001); Avery's Drug Treatment: Principles and Practice of Clinical Pharmacology and Therapeutics, 3rd edition, ADIS Press, Ltd., Williams and Wilkins, Baltimore, Md. (1987); Ebadi, Pharmacology, Little, Brown and Co., Boston, (1985); Osolci al., eds., Remington's Pharmaceutical Sciences, 18$^{th}$ edition, Mack Publishing Co., Easton, Pa. (1990); Katzung, Basic and Clinical Pharmacology, Appleton and Lange, Norwalk, Conn. (1992).

Also included are methods of modulating an immune response, such as an innate immune response. As used herein, the term "immune response" includes a measurable or observable reaction to an antigen, vaccine composition, or immunomodulatory molecule mediated by one or more cells of the immune system. An immune response typically begins with an antigen or immunomodulatory molecule binding to an immune system cell. A reaction to an antigen or immunomodulatory molecule may be mediated by many cell types, including a cell that initially binds to an antigen or immunomodulatory molecule and cells that participate in mediating an innate, humoral, cell-mediated immune response.

An "innate immune response," as used herein, may involve binding of pathogen-associated molecular patterns (PAMPs) or an AspRS polypeptide to cell surface receptors, such as toll-like receptors. Activation of toll-like receptors and Ipaf-signaling pathways in response to PAMPs or other signals leads to the production of immunomodulatory molecules, such as cytokines and co-stimulatory molecules, which induce and/or enhance an immune response. Cells involved in the innate immune response include, for example, dendritic cells, macrophages, natural killer cells, and neutrophils, among others.

Certain embodiments relate to increasing an innate immune response. Other embodiments relate to decreasing an innate immune response. In certain aspects, an innate immune response is mediated by one or more toll-like receptors (TLRs), such as TLR2 and/or TLR4. Certain AspRS polypeptides of the invention bind to TLRS such as TLR2 and/or TLR4. TLRs recognize PAMPs that distinguish infectious agents from self and mediating the production of immunomodulatory molecules, such as cytokines, necessary for the development of effective adaptive immunity (Aderem, A and Ulevitch, R. J. Nature 406: 782-787 (2000) and Brightbill, H. D., Immunology 101: 1-10 (2000), herein incorporated by reference). Members of the toll-like receptor family recognize a variety of antigen types and can discriminate between pathogens. For example, TLR2 recognizes various fungal, Gram-positive, and mycobacterial components, TLR4 recognizes the Gram-negative product lipopolysaccharide (LPS), and TLR9 recognizes nucleic acids such as CpG repeats in bacterial DNA.

AspRS compositions that stimulate innate immunity (e.g., via TLR2 and/r TLR4) can be useful in the treatment of a wide variety of conditions, either alone or in combination with other therapies. Specific examples of such conditions include infectious diseases, such as bacterial, viral, and parasitic infectious diseases. AspRS compositions that stimulate innate immunity can also be useful as vaccine adjuvants, to enhance a subject's immune response to the primary antigen, whether in a live, attenuated, or other type of vaccine.

Examples of viral infectious diseases or agents (and their corresponding vaccines) include, but are not limited to, Hepatitis A, Hepatitis B, Hepatitis C, Hepatitis E, Calicivi-ruses associated diarrhoea, Rotavirus diarrhoea, *Haemophilus influenzae* B pneumonia and invasive disease, influenza, measles, mumps, rubella, Parainfluenza associated pneumonia, Respiratory syncytial virus (RSV) pneumonia, Severe Acute Respiratory Syndrome (SARS), Human papillomavirus, Herpes simplex type 2 genital ulcers, HIV/AIDS, Dengue Fever, Japanese encephalitis, Tick-borne encephalitis, West-Nile virus associated disease, Yellow Fever, Epstein-Barr virus, Lassa fever, Crimean-Congo haemorrhagic fever, Ebola haemorrhagic fever, Marburg haemorrhagic fever, Rabies, Rift Valley fever, Smallpox, leprosy, upper and lower respiratory infections, poliomyelitis, among others described elsewhere herein.

Examples of bacterial infections disease or agents include, but are not limited to, *Bacillus antracis, Borellia burgdorferi, Brucella abortus, Brucella canus, Brucella melitensis, Brucella suis, Campylobacter jejuni, Chlamydia pneumoniae, Chlamydia psitacci, Chlamydia trachomatis, Clostridium botulinum, C. difficile, C. perfringens, C. tetani, Corynebacterium diphtheriae* (i.e., diphtheria), *Enterococ-* cus, *Escherichia coli, Haemophilus influenza, Helicobacter pylori, Legionella pneumophila, Leptospira, Listeria monocytogenes, Mycobacterium leprae, M. tuberculosis, Mycoplasma pneumoniae, Neisseria gonorrhea, N. meningitidis, Pseudomonas aeruginosa, Rickettsia recketisii, Salmonella typhi, S. typhimurium, Shigella sonnei, Staphylococcus aureus, S. epidermidis, S. saprophyticus, Streptococcus agalactiae, S. pneumoniae, S. pyogenes, Treponema pallidum, Vibrio cholera, Yersinia pestis, Bordatella pertussis*, and otitis media (e.g., often caused by *Streptococcus pneumoniae, Haemophilus influenzae*, or *Moraxella catarrhalis*), among others described elsewhere herein.

Examples of parasitic infectious diseases include, but are not limited to, Amoebiasis (e.g., *Entemoeba histolytica*), Hookworm Disease (e.g., nematode parasites such as *Necator americanus* and *Ancylostoma duodenale*), Leishmaniasis, Malaria (four species of the protozoan parasite *Plasmodium; P. falciparum, P. vivax, P. ovale*, and *P. malariae*), Schistosomiasis (parasitic *Schistosoma; S. mansoni, S. haematobium*, and *S. japonicum*), *Onchocerca volvulus* (River blindness), *Trypanosoma cruzi* (Chagas disease/American sleeping sickness), and *Dracunculus medinensis*, lymphatic filariasis.

Certain AspRS compositions may be useful in the treatment or reduction of endotoxic shock, which often results from exposure to foreign antigens, such as lipopolysaccharide (LPS). Because endotoxic shock can be mediated by TLR signaling, and naturally-occurring endogenous AspRS fragments may stimulate TLRs, certain of the binding agents, antisense agents, or RNAi agents provided herein may render a subject more resistant to endotoxic shock by antagonizing or otherwise reducing the endogenous AspRS fragment-mediated stimulation of TLR2 and/or TLR4.

Also included are methods of treating immune diseases. Illustrative immune system diseases, disorders or conditions that may be treated according to the present invention include, but are not limited to, primary immunodeficiencies, immune-mediated thrombocytopenia, Kawasaki syndrome, bone marrow transplant (for example, recent bone marrow transplant in adults or children), chronic B cell lymphocytic leukemia, HIV infection (for example, adult or pediatric HIV infection), chronic inflammatory demyelinating polyneuropathy, post-transfusion purpura, and the like.

Additionally, further diseases, disorders and conditions include Guillain-Barre syndrome, anemia (for example, anemia associated with parvovirus B19, patients with stable multiple myeloma who are at high risk for infection (for example, recurrent infection), autoimmune hemolytic anemia (for example, warm-type autoimmune hemolytic anemia), thrombocytopenia (for example, neonatal thrombocytopenia), and immune-mediated neutropenia), transplantation (for example, cytomegalovirus (CMV)-negative recipients of CMV-positive organs), hypogammaglobulinemia (for example, hypogammaglobulinemic neonates with risk factor for infection or morbidity), epilepsy (for example, intractable epilepsy), systemic vasculitic syndromes, myasthenia gravis (for example, decompensation in myasthenia gravis), dermatomyositis, and polymyositis.

Further autoimmune diseases, disorders and conditions include but are not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (for example, IgA nephropathy), multiple sclerosis, neuritis, uveitis ophthalmia, polyendocrinopathies, purpura (for example, Henloch-Scoenlein purpura), Reiter's disease, stiff-man syndrome, autoimmune pulmonary inflammation, Guillain-Barre Syndrome, insulin dependent diabetes mellitus, and autoimmune inflammatory eye disease.

Additional autoimmune diseases, disorders or conditions include, but are not limited to, autoimmune thyroiditis; hypothyroidism, including Hashimoto's thyroiditis and thyroiditis characterized, for example, by cell-mediated and humoral thyroid cytotoxicity; SLE (which is often characterized, for example, by circulating and locally generated immune complexes); Goodpasture's syndrome (which is often characterized, for example, by anti-basement membrane antibodies); pemphigus (which is often characterized, for example, by epidermal acantholytic antibodies); receptor autoimmunities such as, for example, Graves' disease (which is often characterized, for example, by antibodies to a thyroid stimulating hormone receptor; myasthenia gravis, which is often characterized, for example, by acetylcholine receptor antibodies); insulin resistance (which is often characterized, for example, by insulin receptor antibodies); autoimmune hemolytic anemia (which is often characterized, for example, by phagocytosis of antibody-sensitized red blood cells); and autoimmune thrombocytopenic purpura (which is often characterized, for example, by phagocytosis of antibody-sensitized platelets).

Further autoimmune diseases, disorders or conditions include, but are not limited to, rheumatoid arthritis (which is often characterized, for example, by immune complexes in joints); scleroderma with anti-collagen antibodies (which is often characterized, for example, by nucleolar and other nuclear antibodies); mixed connective tissue disease, (which is often characterized, for example, by antibodies to extractable nuclear antigens, for example, ribonucleoprotein); polymyositis/dermatomyositis (which is often characterized, for example, by nonhistone anti-nuclear antibodies); pernicious anemia (which is often characterized, for example, by antiparietal cell, antimicrosome, and anti-intrinsic factor antibodies); idiopathic Addison's disease (which is often characterized, for example, by humoral and cell-mediated adrenal cytotoxicity); infertility (which is often characterized, for example, by antispennatozoal antibodies); glomerulonephritis (which is often characterized, for example, by glomerular basement membrane antibodies or immune complexes); by primary glomerulonephritis, by IgA nephropathy; bullous pemphigoid (which is often characterized, for example, by IgG and complement in the basement membrane); Sjogren's syndrome (which is often characterized, for example, by multiple tissue antibodies and/or the specific nonhistone antinuclear antibody (SS-B)); diabetes mellitus (which is often characterized, for example, by cell-mediated and humoral islet cell antibodies); and adrenergic drug resistance, including adrenergic drug resistance with asthma or cystic fibrosis (which is often characterized, for example, by beta-adrenergic receptor antibodies).

Still further autoimmune diseases, disorders or conditions include, but are not limited to chronic active hepatitis (which is often characterized, for example by smooth muscle antibodies); primary biliary cirrhosis (which is often characterized, for example, by anti-mitochondrial antibodies); other endocrine gland failure (which is characterized, for example, by specific tissue antibodies in some cases); vitiligo (which is often characterized, for example, by anti-melanocyte antibodies); vasculitis (which is often characterized, for example, by immunoglobulin and complement in vessel walls and/or low serum complement); post-myocardial infarction conditions (which are often characterized, for example, by anti-myocardial antibodies); cardiotomy syndrome (which is often characterized, for example, by antimyocardial antibodies); urticaria (which is often characterized, for example, by IgG and IgM antibodies to IgE); atopic dermatitis (which is often characterized, for example, by IgG and IgM antibodies to IgE); asthma (which is often characterized, for example, by IgG and IgM antibodies to IgE); inflammatory myopathies; and other inflammatory, granulomatous, degenerative, and atrophic disorders.

Also included are methods of modulating hematopoiesis and related conditions. Examples of hematopoietic processes that may be modulated by the AspRS polypeptides of the invention include, without limitation, the formation of myeloid cells (e.g., erythroid cells, mast cells monocytes/macrophages, myeloid dendritic cells, granulocytes such as basophils, neutrophils, and eosinophils, megakaryocytes, platelets) and lymphoid cells (e.g., natural killer cells, lymphoid dendritic cells, B-cells, and T-cells). Certain specific hematopoietic processes include erythropoiesis, granulopoiesis, lymphopoiesis, megakaryopoiesis, thrombopoiesis, and others. Also included are methods of modulating the trafficking or mobilization of hematopoietic cells, including hematopoietic stem cells, progenitor cells, erythrocytes, granulocytes, lymphocytes, megakaryocytes, and thrombocytes.

The methods of modulating hematopoiesis may be practiced in vivo, in vitro, ex vivo, or in any combination thereof. These methods can be practiced on any biological sample, cell culture, or tissue that contains hematopoietic stem cells, hematopoietic progenitor cells, or other stem or progenitor cells that are capable of differentiating along the hematopoietic lineage (e.g., adipose tissue derived stem cells). For in vitro and ex vivo methods, stem cells and progenitor cells, whether of hematopoietic origin or otherwise, can be isolated and/or identified according to the techniques and characteristics described herein and known in the art.

In other embodiments, the AspRS compositions of the invention may be used to modulate cellular proliferation and/or survival and, accordingly, for treating or preventing diseases, disorders or conditions characterized by abnormalities in cellular proliferation and/or survival. For example, in certain embodiments, the AspRS compositions may be used to modulate apoptosis and/or to treat diseases or conditions associated with abnormal apoptosis. Apoptosis is the term used to describe the cell signaling cascade known as programmed cell death. Various therapeutic indications exist for molecules that induce apoptosis (e.g. cancer), as well as those that inhibit apoptosis (i.e. stroke, myocardial infarction, sepsis, etc.). Apoptosis can be monitored by any of a number of available techniques known and available in the art including, for example, assays that measure fragmentation of DNA, alterations in membrane asymmetry, activation of apoptotic caspases and/or release of cytochrome C and AIF.

Illustrative diseases associated with increased cell survival, or the inhibition of apoptosis include, but are not limited to, cancers (such as follicular lymphomas, carcinomas, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Graves' disease, Hashimoto's thyroiditis, autoimmune diabetes, biliary cirrhosis, Behcet's disease, Crohn's disease, polymyositis, systemic lupus erythematosus and immune-related glomerulonephritis, autoimmune gastritis, autoimmune thrombocytopenic purpura, and rheumatoid arthritis) and viral infections (such as herpes viruses, pox viruses and adenoviruses), inflammation, graft vs. host disease (acute and/or chronic), acute graft rejection, and chronic graft rejection.

Further illustrative diseases or conditions associated with increased cell survival include, but are not limited to, progression and/or metastases of malignancies and related disorders such as leukemia (including acute leukemias (for example, acute lymphocytic leukemia, acute myelocytic leukemia, including myeloblastic, promyelocytic, myelomonocytic, monocytic, and erythroleukemia)) and chronic leukemias (for example, chronic myelocytic (granulocytic) leukemia and chronic lymphocytic leukemia), myelodysplastic syndrome polycythemia vera, lymphomas (for example, Hodgkin's disease and non-Hodgkin's disease), multiple myeloma, Waldenstrom's macroglobulinemia, heavy chain diseases, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Illustrative diseases associated with increased apoptosis include, but are not limited to, AIDS (such as HIV-induced nephropathy and HIV encephalitis), neurodegenerative disorders (such as Alzheimer's disease, Parkinson's disease, amyotrophic lateral sclerosis, retinitis pigmentosa, cerebellar degeneration and brain tumor or prior associated disease), autoimmune disorders such as multiple sclerosis, Sjogren's syndrome, Graves' disease, Hashimoto's thyroiditis, autoimmune diabetes, biliary cirrhosis, Behcet's disease, Crohn's disease, polymyositis, systemic lupus erythematosus, immune-related glomerulonephritis, autoimmune gastritis, thrombocytopenic purpura, and rheumatoid arthritis, myelodysplastic syndromes (such as aplastic anemia), graft vs. host disease (acute and/or chronic), ischemic injury (such as that caused by myocardial infarction, stroke and reperfusion injury), liver injury or disease (for example, hepatitis related liver injury, cirrhosis, ischemia/reperfusion injury, cholestosis (bile duct injury) and liver cancer), toxin-induced liver disease (such as that caused by alcohol), septic shock, ulcerative colitis, cachexia, and anorexia.

In still further embodiments, the compositions of the invention may be used in the treatment of neuronal/neurological diseases or disorders, illustrative examples of which include Parkinson's disease, Alzheimer's disease, Pick's disease, Creutzfeldt-Jacob disease, Huntington's chorea, alternating hemiplegia, amyotrophic lateral sclerosis, ataxia, cerebral palsy, chronic fatigue syndrome, chronic pain syndromes, congenital neurological anomalies, cranial nerve diseases, delirium, dementia, demyelinating diseases, dysautonomia, epilepsy, headaches, Huntington's disease, hydrocephalus, meningitis, movement disorders, muscle diseases, nervous system neoplasms, neurocutaneous syndromes, neurodegenerative diseases, neurotoxicity syndromes, ocular motility disorders, peripheral nervous system disorders, pituitary disorders, porencephaly, Rett syndrome, sleep disorders, spinal cord disorders, stroke, sydenham's chorea, tourette syndrome, nervous system trauma and injuries, etc.

Furthermore, additional embodiments relate to the use of the compositions of the invention in the treatment of metabolic disorders such as adrenoleukodystrophy, Krabbe's disease (globoid cell leukodystrophy), metachromatic leukodystrophy, Alexander's disease, Canavan's disease (spongiform leukodystrophy), Pelizaeus-Merzbacher disease, Cockayne's syndrome, Hurler's disease, Lowe's syndrome, Leigh's disease, Wilson's disease, Hallervorden-Spatz disease, Tay-Sachs disease, etc. The utility of the compositions of the invention in modulating metabolic processes may be monitored using any of a variety of techniques known and available in the art including, for example, assays which measure adipocyte lipogenesis or adipocyte lipolysis.

In more specific embodiments of the invention, the AspRS compositions of the invention may be used to modulate cellular signaling, for example, via cell signaling proteins (e.g., Akt). Cell signaling may be monitored using any of a number of well known assays. For example, the induction of general cell signaling events can be monitored through altered phosphorylation patterns of a variety of target proteins. Detection of cell signaling activities in response to treatment of cells with AspRS polypeptides therefore serves as an indicator of distinct biological effects. Target proteins used for this assay may be selected so as to encompass key components of major cellular signaling cascades, thereby providing a broad picture of the cell signaling landscape and its therapeutic relevance. Generally, such assays involve cell treatment with AspRS polypeptides followed by immunodetection with antibodies that specifically detect the phosphorylated (activated) forms of the target proteins.

Illustrative target proteins used for monitoring therapeutically relevant cell signaling events may include, but are not limited to: p38 MAPK (mitogen-activated protein kinase; activated by cellular stress and inflammatory cytokines; involved in cell differentiation and apoptosis); SAPK/JNK (stress-activated protein kinase/Jun-amino-terminal kinase; activated by cellular stresses and inflammatory cytokines); Erk1/2, p44/42 MAPK (mitogen-activated protein kinase Erk1 and Erk2; activated by wide variety of extracellular signals; involved in regulation of cell growth and differentiation); and Akt (activated by insulin and various growth or survival factors; involved in inhibition of apoptosis, regulation of glycogen synthesis, cell cycle regulation and cell growth). General phosphorylation of tyrosine residues may also be monitored as a general indicator of changes in cell signaling mediated by phosphorylation.

Of course, it will be recognized that other classes of proteins, such as cell adhesion molecules (e.g., cadherins, integrins, claudins, catenins, selectins, etc.) and/or ion channel proteins may also be assayed for monitoring cellular events or activities modulated by the compositions of the invention.

In other specific embodiments of the invention, the AspRS compositions of the invention may be used to modulate cytokine production by cells, for example, by immune cells such as monocytes and/or leukocytes. Cytokine production may be monitored using any of a number of assays known in the art (i.e., RT-PCR, ELISA, ELISpot, flow cytometry, etc.). Generally, such assays involve cell treatment with AspRS polypeptides followed by detection of cytokine mRNA or polypeptides to measure changes in cytokine production. Detection of increases and/or decreases in cytokine production in response to treatment of cells with AspRS polypeptides therefore serves as an indicator of distinct biological effects. AspRS polypeptides of the invention may induce, enhance, and/or inhibit an immune or inflammatory response by modulating cytokine production. For example, AspRS polypeptides and compositions of the invention may be used to alter a cytokine profile (i.e., type 1 vs. type 2) in a subject. Illustrative cytokines that may measured for monitoring biological effects of the AspRS compositions include, but are not limited to IL-1ra, IL-1α, IL-1β, IL-2, IL-3, IL-4, IL-5, IL-6, IL-7, IL-8, IL-10, IL-12, IL-12p40, IL-15, IL-18, IL-23 TGF-β, TNF-α, IFN-α, IFN-β, IFN-γ, RANTES, MIP-1α, MIP-1β, MCP-1, GRO-α, GM-CSF, G-CSF, etc.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Generation of Human Aspartyl-tRNA Synthetase (AspRS) Fragments

Full-length recombinant human AspRS having an amino acid sequence as set forth in SEQ ID NO: 1 was expressed and purified from *E. coli* using nickel IMAC chromatography. To generate fragments of AspRS by controlled proteolysis, the full-length protein was treated with 42 nM human neutrophil elastase for 30 minutes before separation of the fragments by SDS-PAGE run in 4-12% MOPS or 12% MES buffer (FIGS. 1C and D). Digestions run on SDS-PAGE gels in 4-12% MOPS revealed only a single protein fragment at approximately 19 kDa (FIG. 1C), while digestions run on SDS-PAGE gels in 12% MES buffer revealed at least three additional smaller peptide fragments between 3 and 6 kDa (FIG. 1D).

Example 2

AspRS Fragments Activate Akt in Endothelial Cells

Pools of AspRS fragments were generated by adding 42 nM neutrophil elastase to 2 ug full-length recombinant AspRS for 30 minutes at 37° C. Reactions were stopped by the addition of alpha 1-antitrypsin (Serpin A1) in 10-fold excess of the protease. Bovine aortic endothelial cells (bAEC) were treated with pools of 50 nM full-length AspRS protein uncleaved or cleaved with neutrophil elastase. Cells were incubated with AspRS fragments for 10 and 15 minutes, harvested and subjected to Western blotting with an antibody that specifically recognizes only the phosphorylated (activated) form of the signaling molecule Akt. This treatment resulted in strong, reproducible activation of Akt via phosphorylation (FIGS. 2A and 2B). This effect is significant due to the role of Akt in the regulation of apoptosis, glycogen synthesis, cell cycle regulation, and cell growth.

Example 3

Identification of Neutrophil Elastase Cleavage Sites on AspRS

Fragments generated by cleavage with neutrophil elastase (FIG. 1D) were analyzed using LC/MS/MS to determine accurate masses for each fragment. In addition, individual fragments were excised from an SDS-PAGE gel run in 4-12% MOPS or 12% MES buffer and subjected to in-gel trypsin digestion followed by LC/MS/MS analysis to identify the portion of the full-length protein from which the fragment was generated and to identify non-trypsin cleavage sites that could be attributed to neutrophil elastase. The identity of these peptide boundaries is summarized in Table 2.

TABLE 2

AspRS peptide boundaries

| Fragment | Whole mass (Da) | Protease used | N-term. boundary | C-term boundary |
|---|---|---|---|---|
| D1 | 19437 18370 | elastase | 1 | 154 |
| D2 | 21590 | elastase | 1 | 174 |
| D3 | 4367 4468 | elastase | 1 | 31 |
| D4 | 3309 | elastase | 399 | 425 |
| D5 | 2517 | elastase | 413 | 476 |
| D6 | 3479 | elastase | 397 | 425 |

Example 4

AspRS Fragment Increases TNF-α Secretion from PBMCs

Peripheral blood mononuclear cells (PBMCs) from healthy donors were treated with 100 nM doses of full-length AspRS protein and a fragment of AspRS, D1 (Table 2), for 24 hours. EMAPII (Endothelial-monocyte-activating polypeptide II), which is known to increase TNF-α secretion from PBMCs, was used as a positive control. An increase in TNF-α secretion was observed in response to the full-length AspRS and this increase was similar in magnitude to that observed for the EMAPII positive control. Unexpectedly, however, the D1 fragment of AspRS induced TNF-α secretion at a level nearly 6-fold higher than that observed for either full length AspRS or the EMAPII positive control (FIG. 3). Thus, the D1 fragment of AspRS has a novel function that is largely masked within the full length protein.

Example 5

Figure 4:
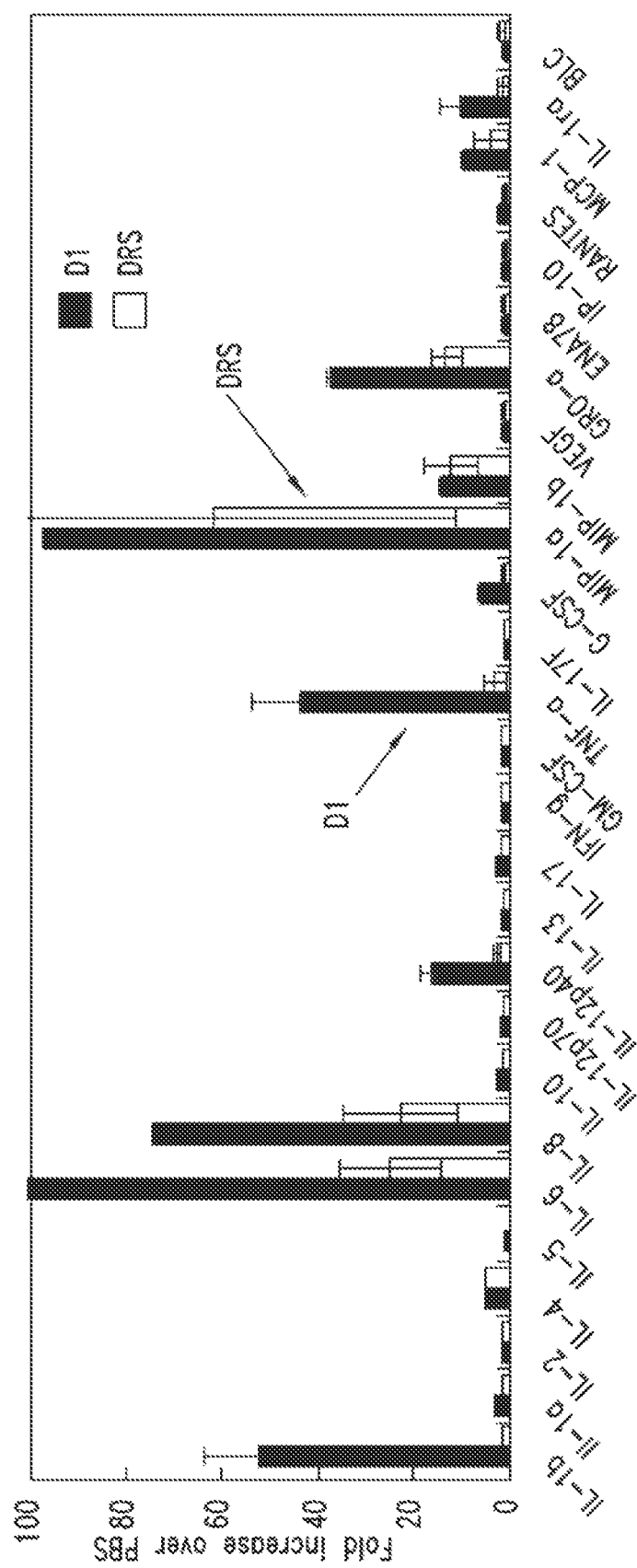
FIG. 4 shows illustrative cytokines that are secreted following treatment of PBMCs with AspRS fragment D1. PBMCs were treated for 24 hours, assayed for secretion of 27 different cytokines, and found to increase secretion of IL1-β, IL-6, IL-8, IL-10, IL-12p40, MIP1-α, MIP-1β, GRO-α, MCP-1, and IL-1ra.

AspRS Fragment D1 Induces In Vitro Secretion of Cytokines Distinct from Full Length AspRS Full length AspRS (100 nM) or a fragment of AspRS, D1 (100 nM), were incubated with $1 \times 10^6$ Peripheral Blood Mononuclear Cells (PBMC) for 24 hours. After 24 hours of incubation, supernatants were harvested, snap frozen in liquid nitrogen and then analyzed for multiple cytokines. Supernatants were measured for 27 distinct cytokines and compared to buffer-treated PBMC supernatants. Error bars are representative of 2 biological replicates. As shown in FIG. 4, AspRS fragment D1 showed a large stimulation of numerous cytokines above and beyond stimulations observed with full length AspRS (e.g., IL1-13, IL-6, IL-8, IL-10, IL-12p40, MIP1-α, MIP-1β, GRO-α, MCP-1, and IL-1ra).

Example 6

AspRS Fragment Induces CD71 Marker Upregulation in Monocytes

Figure 5:
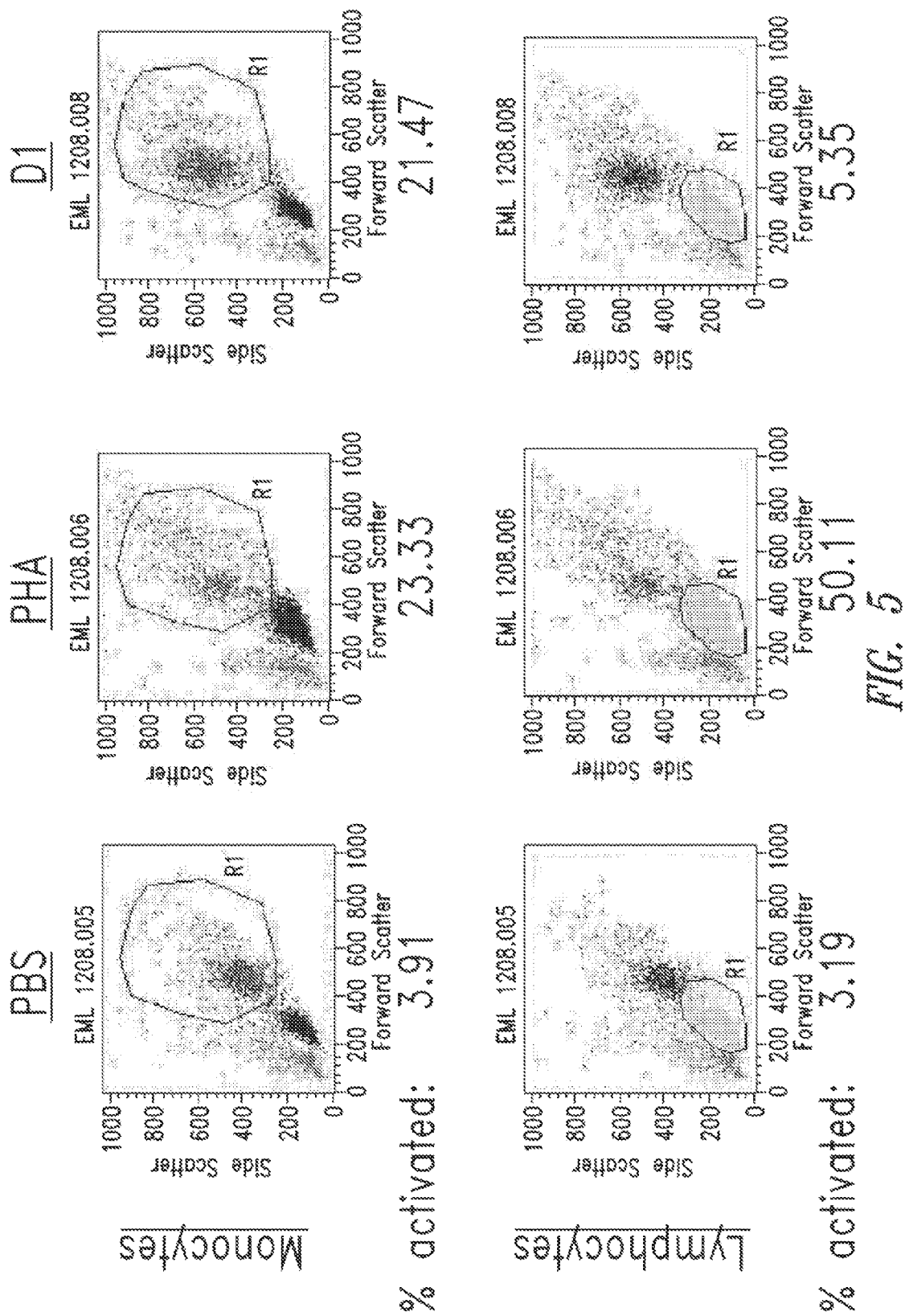
FIG. 5 shows that the AspRS fragment D1 activates monocytes in a cell type specific manner. PBMCs were treated for 24 hours with PBS as a negative control, PHA as a positive control, and AspRS fragment D1, and assayed to detect cell-surface markers of activation on monocytes and lymphocytes.

Peripheral blood mononuclear cells (PBMC's) were isolated from a normal blood donor. $1.5 \times 10^6$ PBMC's were treated with a 200 nM dose of the AspRS fragment D1 (consisting of the first 154 amino acids of the full length protein) for 24 hours. PBMC's treated with 10 µg/mL of the plant lectin phytohemagglutinin (PHA) served as a positive control. As shown in FIG. 5, upregulation of the CD71 proliferation marker was seen in the D1-treated gated monocytes after staining with an anti-CD71 antibody (Beckton-Dickinson) and analyzing the samples by flow cytometry. There was no significant increase in CD71 upregulation in the gated lymphocyte population of the same samples. Thus, D1 has a cell type specific ability to activate monocytes in a PBMC mixture.

Example 7

AspRS Fragment Increases TNF-α Secretion from Monocytes and Macrophages

Figure 6:
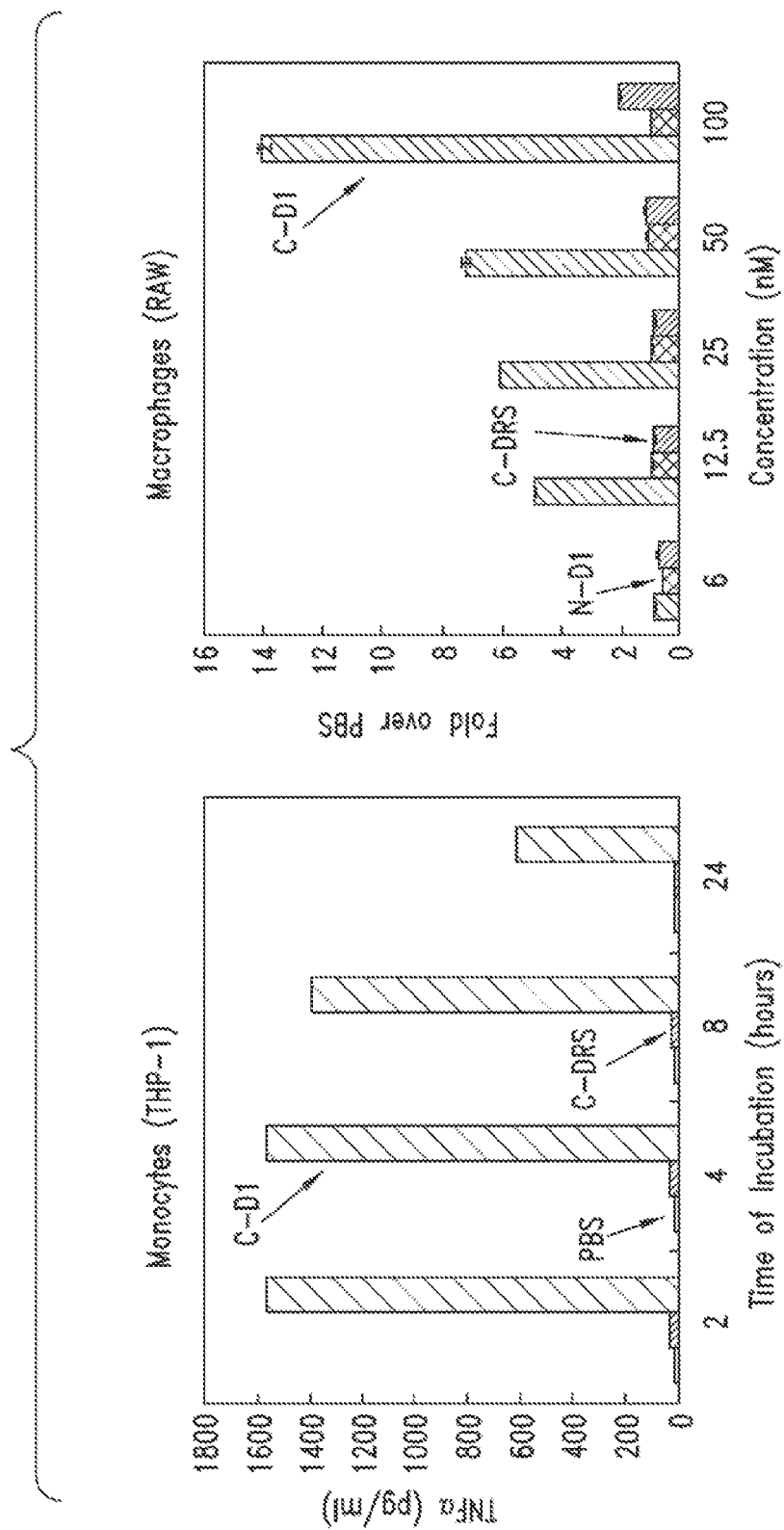
FIG. 6 shows that the AspRS fragment D1 induces secretion of TNF-α from monocyte (e.g., THP-1) and macrophage (e.g., RAW 267.7) cell lines.

Both monocyte (THP-1) and macrophage (RAW 264.7) cell lines were treated with C-terminally tagged D1 (C-D1) or full length AspRS (C-DRS) at 100 nM. Supernatant was collected at 2, 4, 8 and 24, hours and then analyzed for TNF-α secretion. As shown in FIG. 6, the maximal amount of TNF-α secretion after treatment with C-D1 was seen between 2 and 4 hours, but then decreased at 8 and 24 hours. TNF-α secretion following treatment with C-DRS was negligible at all time points examined. The increase in TNF-α secretion following treatment with C-D1 was dose-dependent. In addition, treatment of cells with 100 nM, 50 nM, 25 nM, 12.5 nM, and 6 nM C-D1, N-D1, and C-DRS for 4 hours demonstrated that only C-D1 treatment increased TNF-α secretion.

Example 8

DRS Fragment D1 Induces Chemotaxis of a Macrophage Cell Line

Figure 7:
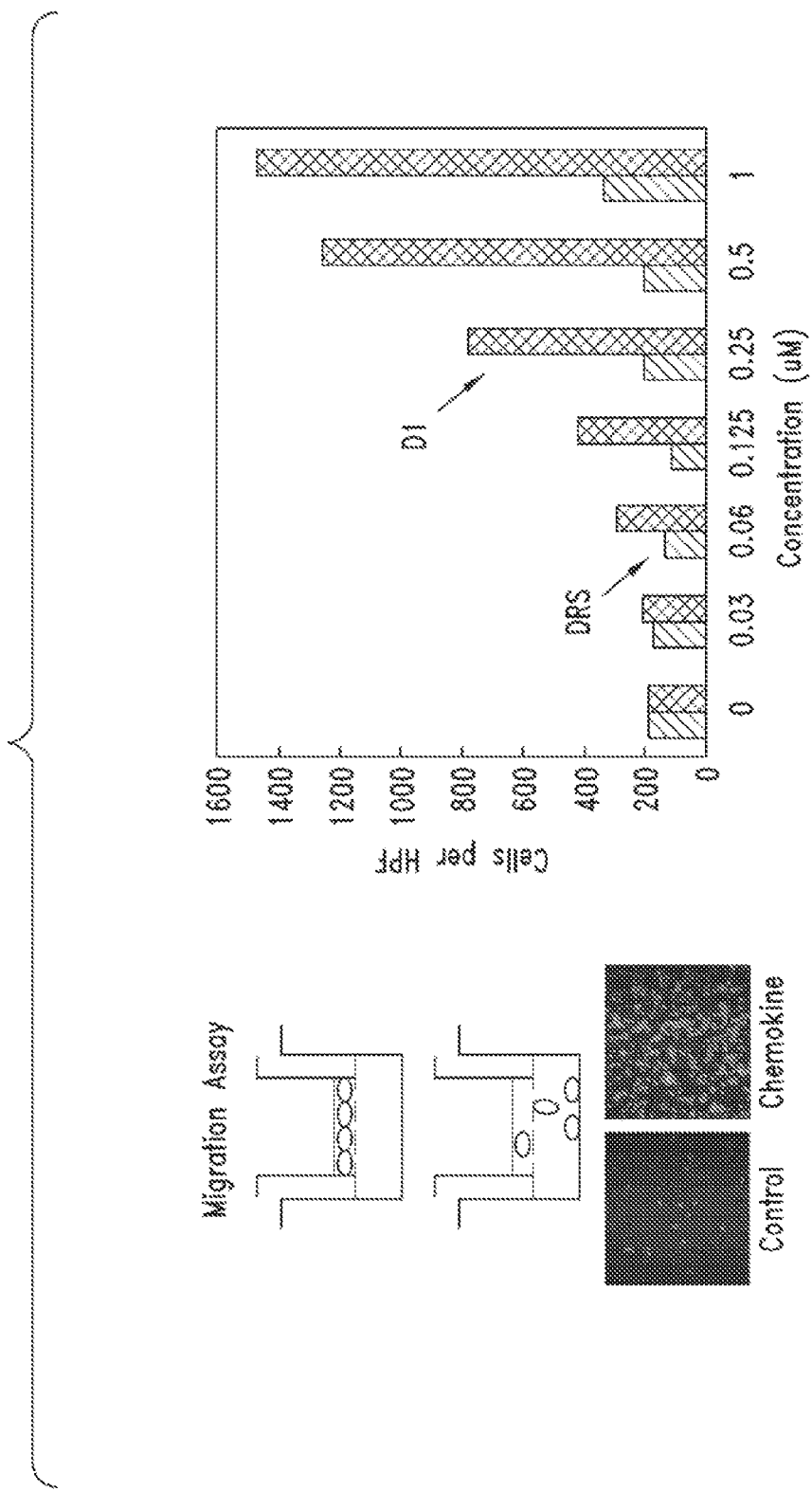
FIG. 7 shows that the AspRS fragment D1 induces chemotaxis of a macrophage cell line.

To assess cell migration in vitro, 24-well Transwell chambers with polycarbonate membranes (5 µm pore size, Costar) were coated with 0.5 mg/ml gelatin in PBS and allowed to air dry. Detached RAW 264.7 cells (mouse monocyte/macrophage cell line) were washed once with fresh DMEM and suspended into $2 \times 10^7$ cells/ml with 0.1% BSA/DMEM. Full-length AspRS (DRS) or D1 was diluted with 0.1% BSA/DMEM into different concentrations. RAW 264.7 cells were added to the upper chamber at $2 \times 10^6$ cells in 100 µl per well. The lower chambers were filled with 500 µl per well of media containing DRS or D1. After 24 hours at 37° C., calcein AM (Invitrogen) was added to lower chambers at a final concentration of 8 μM to stain migrated cells. Following a 30 minute incubation, cells that had not migrated were removed from the upper surface of the Transwell membrane with a cotton swab. Migrating cells on the lower membrane surface were counted under fluorescence microscope in high power fields. As shown in FIG. 7, D1 induced migration in a dose dependent manner, whereas little to no migration was stimulated by full length AspRS at the same concentrations.

Example 9

AspRS Fragment Induced TNF-α Secretion Macrophages can be Inhibited by U0126

Figure 8:
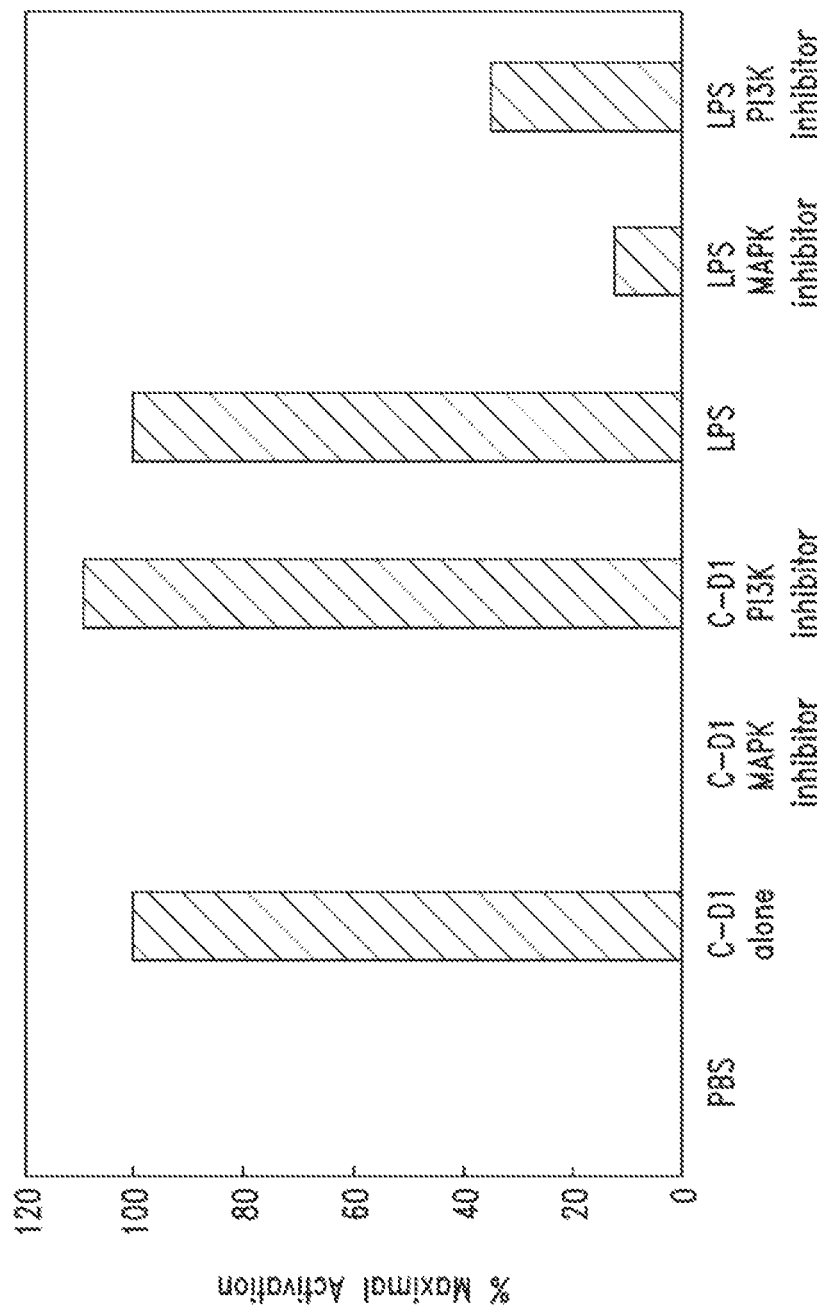
FIG. 8 shows that the TNF-α secretion mediated by the AspRS fragment D1 in THP-1 monocytes is inhibited by an inhibitor of MEK (U0126), a key component in the MAP kinase signaling pathway, but not by an inhibitor of PI3 kinase signaling (LY294022). LPS is used as a positive control and its activity is blocked by both inhibitors.

Macrophage (RAW 264.7) cells were pre-treated with the small-molecule inhibitors U0126 or LY294022 at 100 nM for one hour followed by treatment with D1 at 50 nM or LPS at 1 ng/ml for an additional 4 hours. Supernatant was collected and analyzed for TNF-α secretion. As shown in FIG. 8, secretion of TNF-α was inhibited by U0126 in D1 and LPS treated cells. However, LY294022 only inhibited TNF-α secretion in LPS treated cells.

Example 10

AspRS Fragment D1 Inhibits VEGF-Induced Angiogenesis

Figure 9:
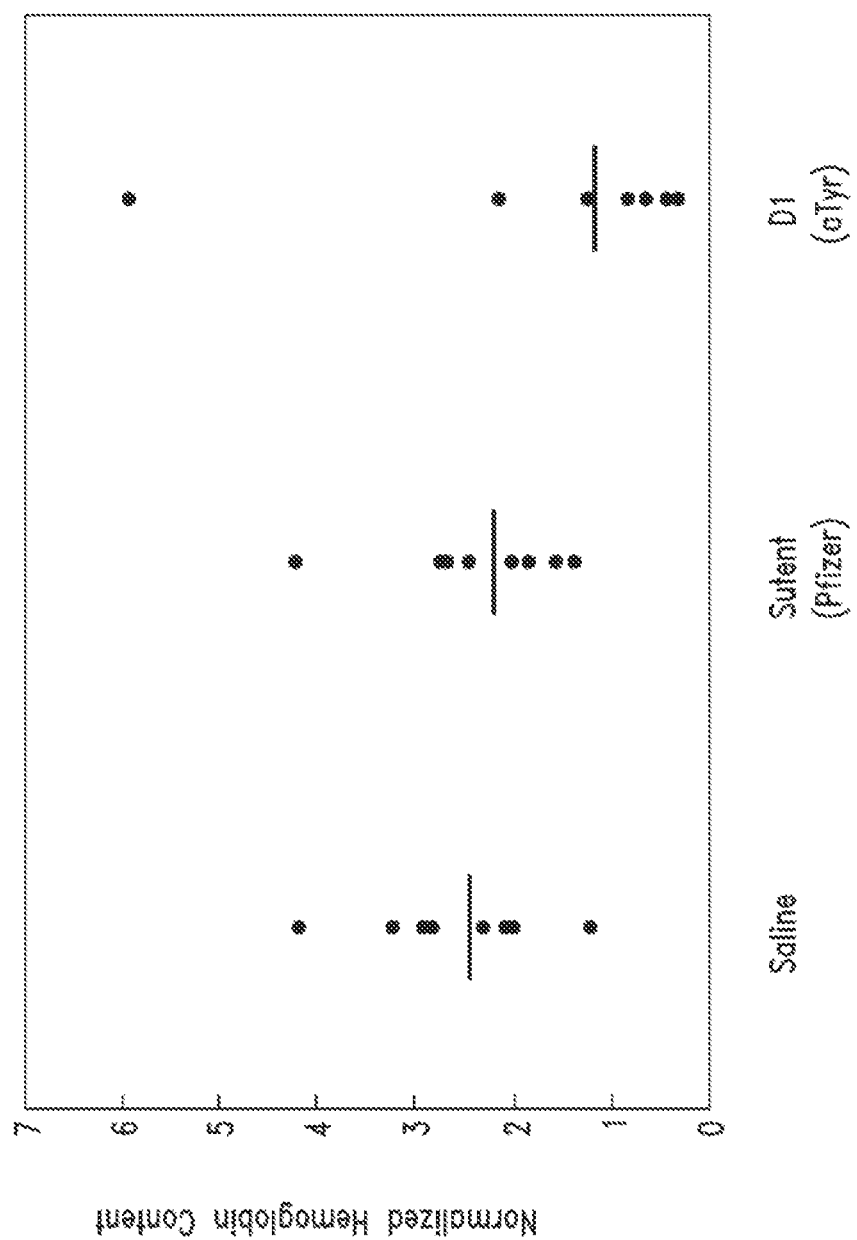
FIG. 9 shows that the AspRS fragment D1 inhibits VEGF-induced angiogenesis. Matrigel solutions containing PBS, sutent, or D1 fragment in combination with VEGF were implanted into mice and analyzed for new blood vessel infiltration into the matrigel plug.

The purpose of this experiment was to evaluate the anti-angiogenic activity of the D1 fragment of AspRS. D1 protein was directly incorporated into Matrigel® plugs to determine its' ability to inhibit VEGF-induced angiogenesis in a Modified Matrigel® Plug Assay. Briefly, female NCR Nude mice (8 mice/group) were obtained that weighed 21-25 g on Day 1 of the experiment. Air pouches were generated in test animals by injecting 1 ml air into the subcutaneous space between the scapulae on Days 1, 4, and 6 using a 27-gauge needle. On Day 7, 0.5 ml Matrigel® (VWR) containing VEGF (Cell Sciences)+Saline, VEGF+ Sutent (Pfizer Pharmaceuticals), or VEGF+D1 protein was injected into the previously created air pouches. On Day 13 (6 days after implant) animals were euthanized and the Matrigel® plugs were excised, photographed, and weighed. The primary endpoint used to evaluate activity was the hemoglobin content per mg of wet Matrigel® plug weight. As Shown in FIG. 9, D1 caused an inhibition of VEGF-induced angiogenesis.

Example 11

C-Terminally Tagged AspRS Fragment Induced TNF-α Secretion in Monocytes

Figure 10:
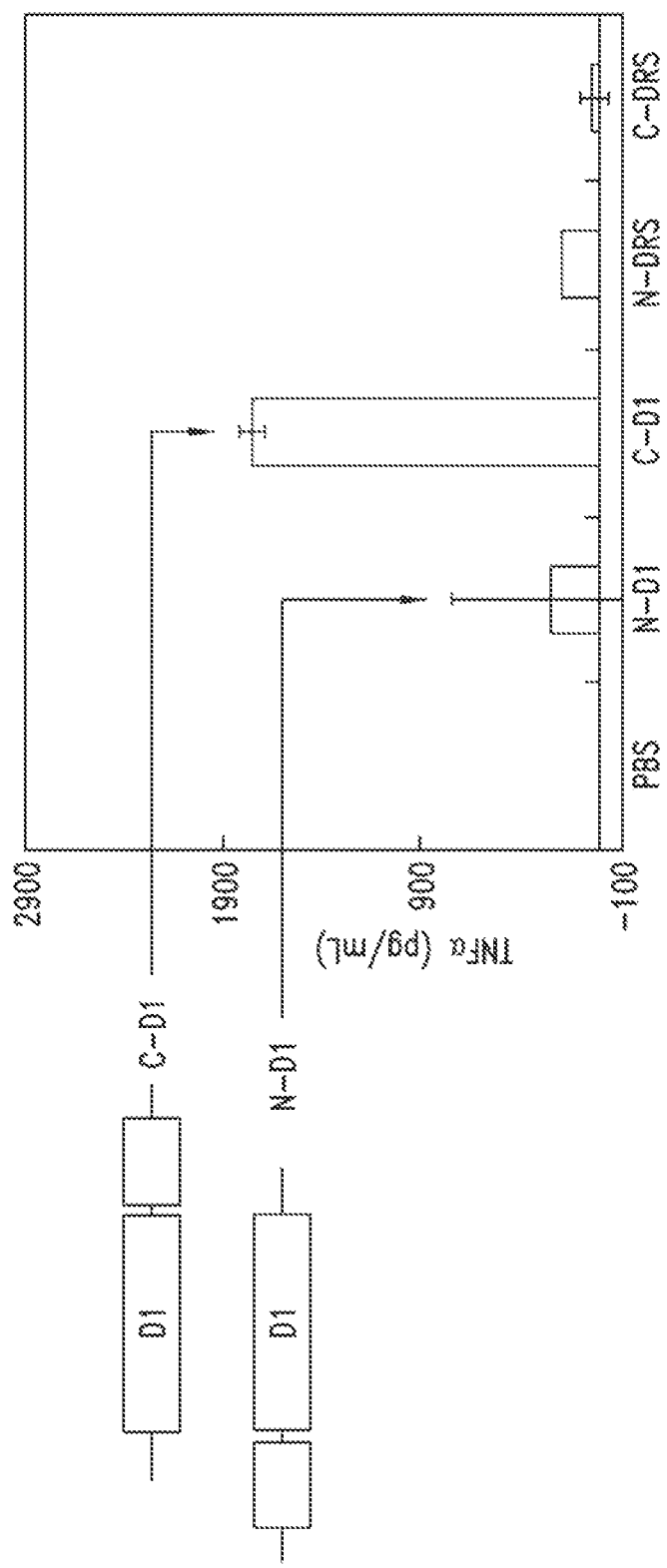
FIG. 10 shows the results of an experiment which suggests that the N-terminal region of the AspRS fragment D1 is responsible for its cytokine activity. The presence of a 6×his affinity tag on the N-terminus of D1, as compared to on the C-terminus of D1, reduces the TNF-α secretion activity of the fragment.

Monocyte (THP-1) cells were treated with C- or N-terminally tagged D1 or full length AspRS at 100 nM for four hours. After which, supernatant was collected and analyzed for TNF-α secretion. As shown in FIG. 10, induction of TNF-α secretion was the greatest in cells treated with C-terminally tagged D1. N-terminally tagged D1 induced a much smaller response, indicating the N-terminus region of the D1 fragment likely plays an important role in its cytokine activity. All other treatment groups had significantly lower induction of TNF-α secretion.

Example 12

AspRS Fragment D1 Contains a Mammalian-Specific Domain of Human Drs

Figure 11:
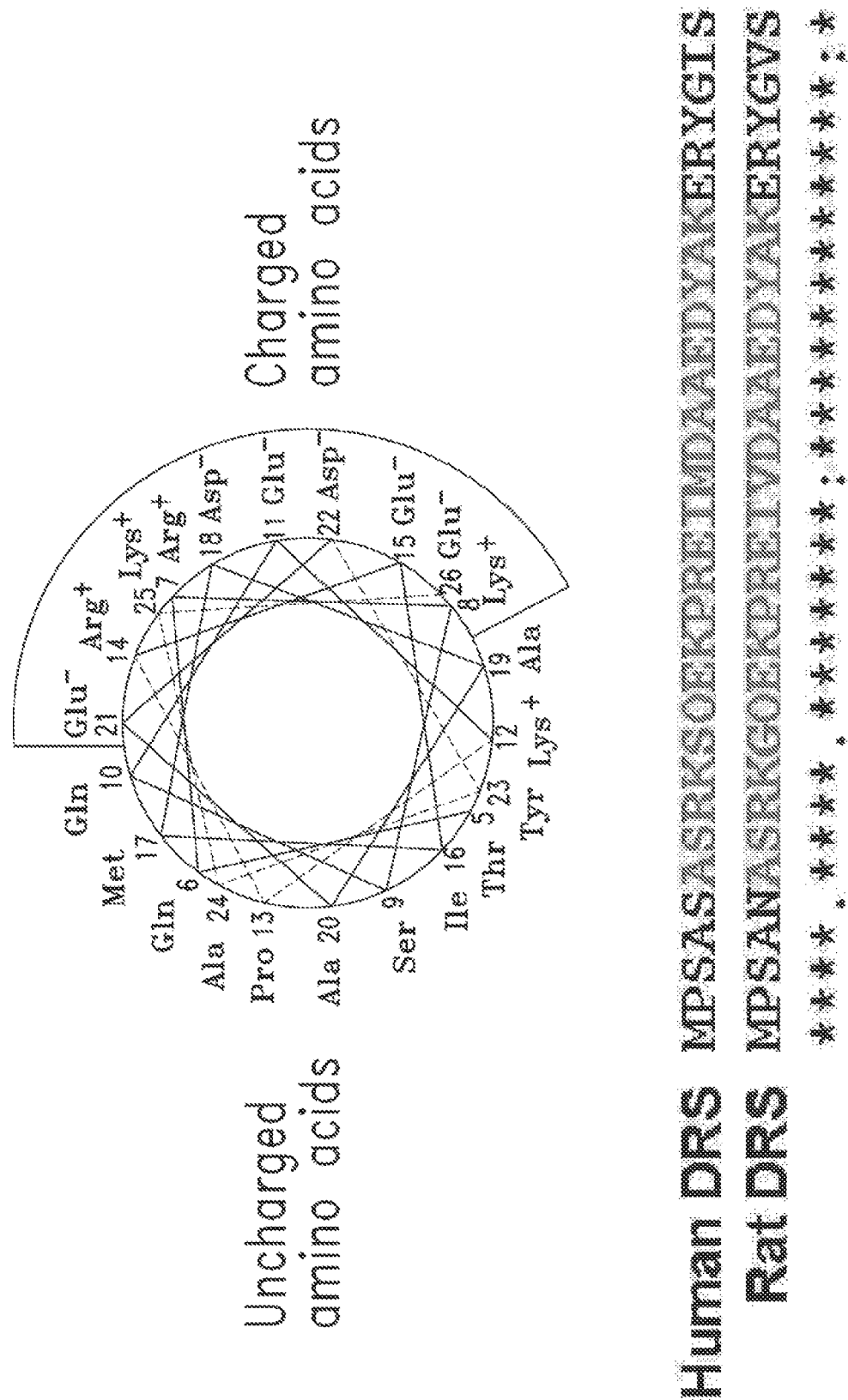
FIG. 11 shows that the AspRS fragment D1 contains a mammalian-specific 32 amino acid sequence at its N-terminus SEQ ID NO:3 is the human AspRS 32 amino acid peptide and SEQ ID NO:4 is the rat AspRS 32 amino acid peptide. A 32 amino acid peptide found only at the N-terminus of mammalian AspRS, and not found in yeast AspRS, is dispensable for canonical tRNA synthetase activity and predicted to contain a putative helix (see Jacobo-Molina and Yang (1989); and Escalante and Yang, *JBC* (1992)).

As shown in FIG. 11, a 32 amino acid peptide is found only at the N-terminus of mammalian DRS and is not found in yeast DRS. This region of the protein is dispensable for canonical tRNA synthetase aminoacylation activity and is predicted to contain a putative amphiphilic helix (reported in Jacobo-Molina and Yang (1989), Escalante and Yang, JBC (1992)). Based on the observed importance of the N-terminus of D1 in relation to its cytokine activity, this unique region may be an important mediator of the cytokine activity reported here for D1.

Example 13

Identification of Endogenous D1 Fragment from Macrophages

Figure 12A:
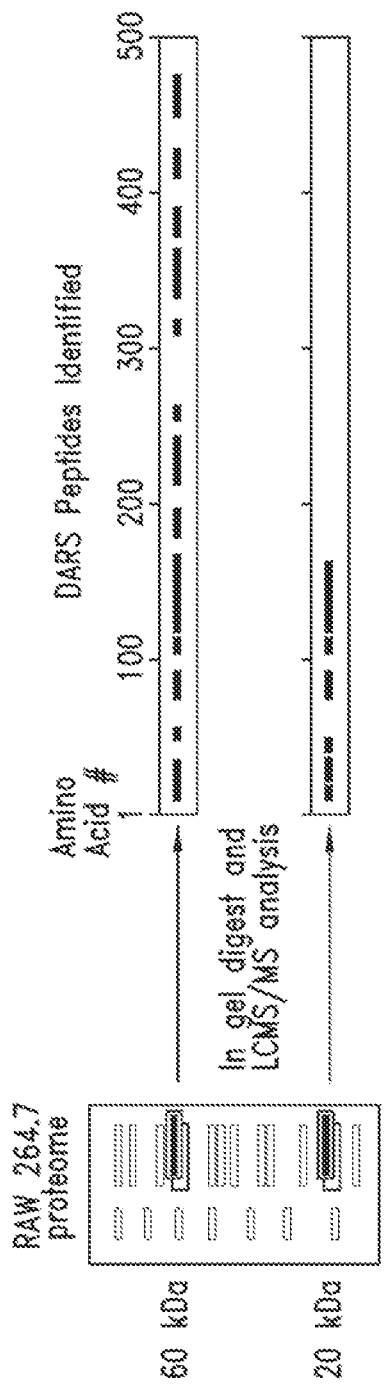
FIGS. 12A-12C show the identification, evolution and crystallization of human AspRS fragment D1.
Figure 12B:
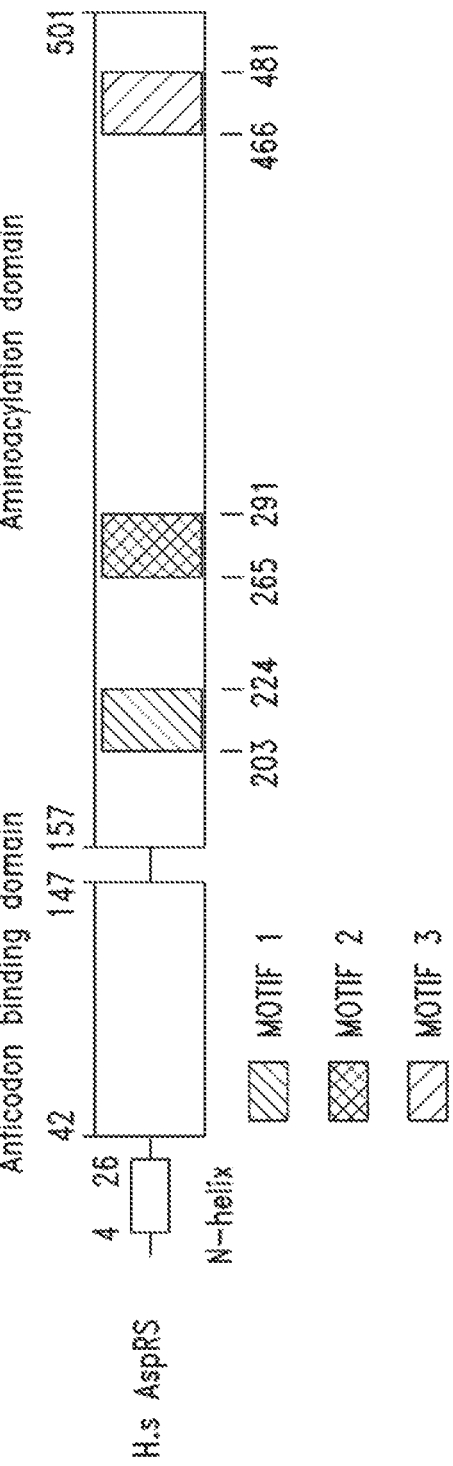

As illustrated in FIG. 12A, a fragment of AspRS was detected in a mouse macrophage cell line (RAW264.7) using LC/MS/MS proteomics analysis. FIG. 12A shows the steps by which RAW264.7 mouse macrophages were subjected to SDS-PAGE analysis; protein bands were cut out and analyzed by LC MS/MS, and an N-terminal fragment of AspRS was identified as D1. This mass spectral analysis revealed that the D1 fragment comprises the N-terminal portion of the 501 residue monomer unit of the AspRS homodimer (consisting approximately of residues 1-171 of full-length AspRS). The D1 fragment includes the anticodon-binding domain of human AspRS (see FIG. 12B), and has structural similarity to the EMAPII-cytokine that contains a highly similar OB-fold domain. The EMAPII cytokine is found as a distinct domain in p43 (a protein that is bound in the multi-tRNA synthetases complex of mammalian cells) where, under apoptotic conditions, it is resected and secreted to serve as an immunomodulatory cytokine. A similar EMAPII-like domain exists in the C-terminal region of human TyrRS. However, in contrast to EMAP-II and the homologous domains found in TyrRS and p43, D1 has a unique 22 amino acid extension at the N-terminus that is found only in higher eukaryotes and forms an amphiphilic helix.

Example 14

Structural Analysis of AspRS

Figure 12C:
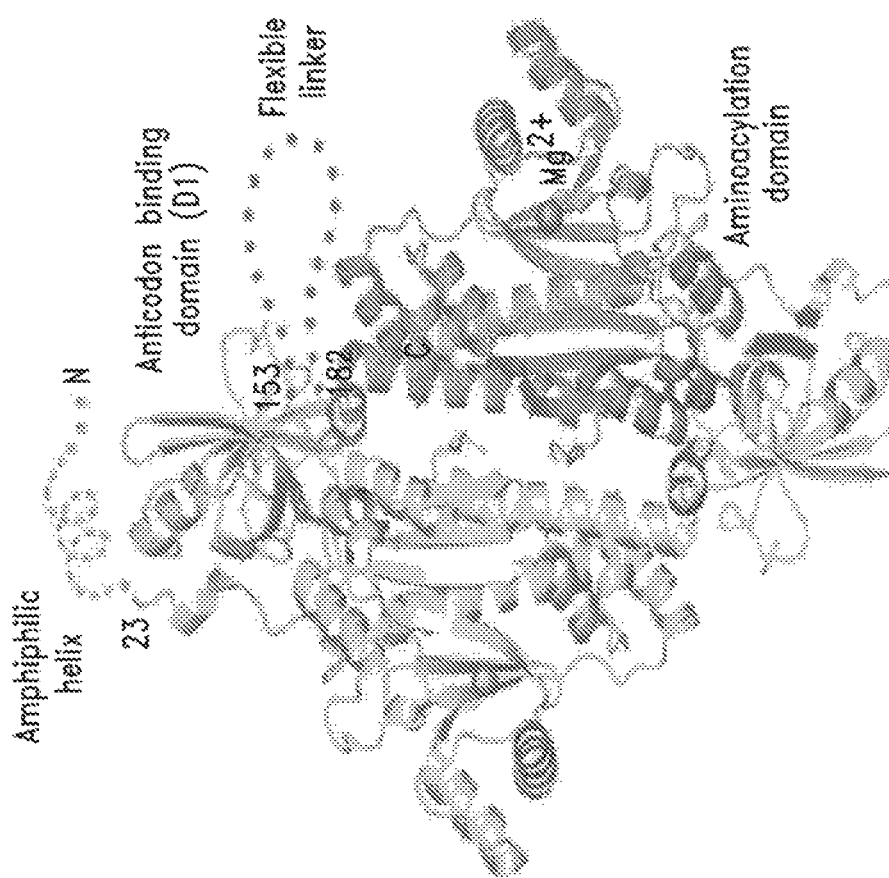

To better understand the structure and physiological origin of D1, native human AspRS was crystallized and its 3-dimensional structure was determined to a resolution of 1.9 Å (see FIG. 12C). The part of the structure corresponding to D1 forms a separate OB-fold-containing domain, while the C-terminal catalytic domain quite resembles that of yeast and bacterial AspRS. The linker encompassing residues 154 and 182 that connect the D1 fragment and the catalytic domain was structurally disordered, suggesting its high flexibility. The flexibility of this linker region and its apparent accessibility to proteases, suggested that its cleavage by endogenous proteases should liberate D1 from native AspRS. Treatment of recombinant native human AspRS with PMN elastase confirmed this expectation by cleavage and clean release of D1 at residue 154 (see Example 3).

Example 15

AspRS Fragment D1 Induces In Vivo and In Vitro Secretion of Cytokines and Binds to Immune Cells Macrophages are key players in innate immunity, and produce and secrete a large number of protein cytokines including those involved in cellular metabolism and inflammation. To probe the possible connection between the D1 fragment of AspRS and inflammation, D1 protein (10 mg/kg) was injected intravenously into healthy mice, and changes were measured in inflammatory cytokines (both pro- and anti-inflammatory) secreted into the bloodstream relative to vehicle controls. Because human and mouse AspRS and D1 have 96.8% sequence identity, recombinant human AspRS and D1 was used for all studies.

Figure 13A:
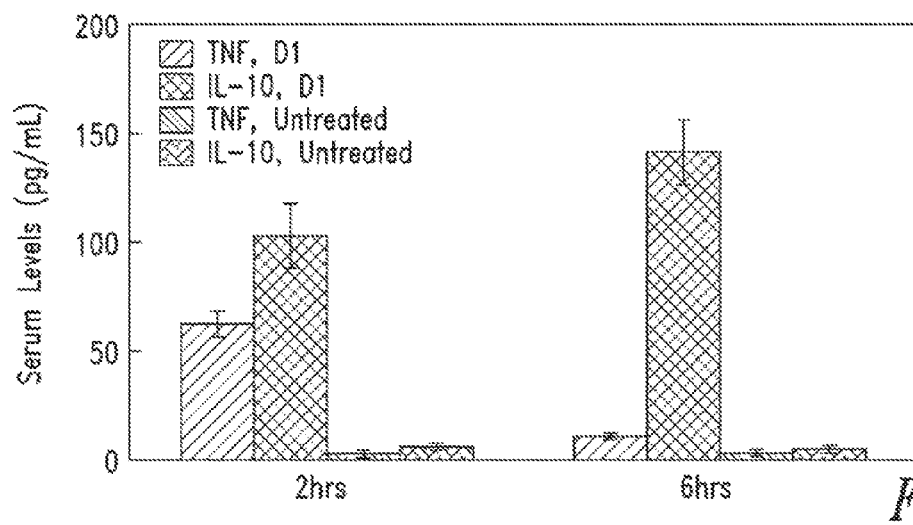
FIGS. 13A-13C show that D1 induces pro-inflammatory and anti-inflammatory cytokine secretion in vivo and in vitro.
Figure 13B:
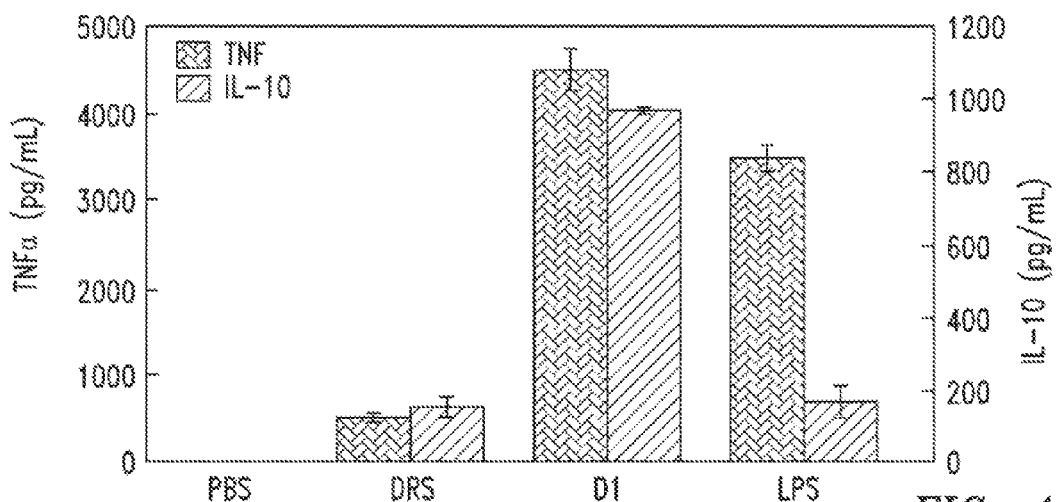

FIG. 13A shows in vivo TNF-α and IL-10 serum levels from mice injected intravenously with 10 mg/kg D1. Mice show an increase in TNF-α after 2 hours that is quickly cleared by 6 hours while IL-10 levels continue to increase. To confirm these in vivo results, PBMCs representing a mixture of both monocytes and lymphocytes and isolated from human donors were also exposed to the D1 protein in vitro (as well as the full-length AspRS protein) and tested the media for the secretion of either TNF-α or IL-10 in response to treatment. Similar to the effects observed in vivo, treatment with D1 resulted in secretion of both TNF-α and IL-10 from this mixed cell population (FIG. 13B). The effects were specific to D1 and were not seen with native AspRS, illustrating the effects of isolating this N-terminal domain from the parent tRNA synthetase by the process of resection.

Figure 13C:
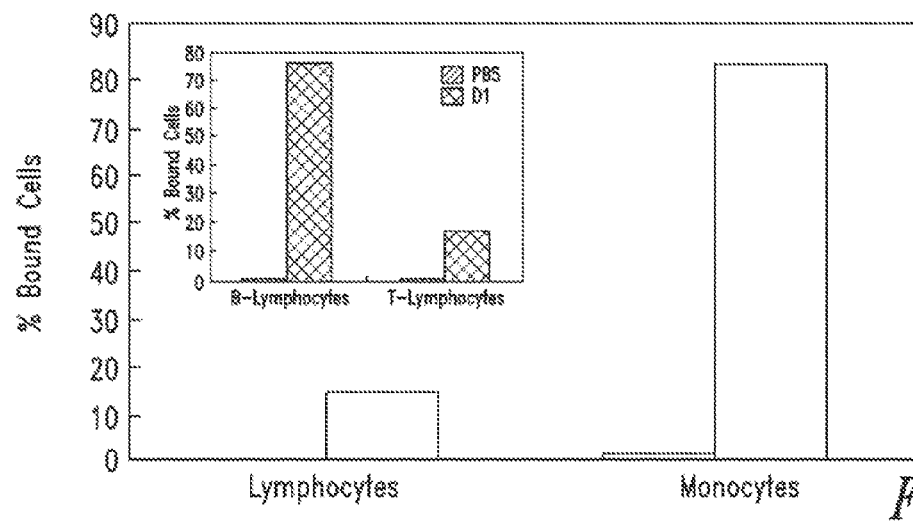

To investigate which cells within the PBMC mixture were targeted by D1, its binding to the different subpopulations of cells within the mixture was analyzed using flow cytometry. As shown in FIG. 13C, robust binding of D1 to monocytes was observed, with almost 100% of monocytes in the mixture bound by a D1 molecule. In contrast, no binding of native AspRS to monocytes was detected (data not shown). Binding of the D1 protein was also observed for a subset of lymphocytes (~14%). Further analysis of the bound lymphocyte population revealed that D1 binding occurs on both B cells (~80% of total B cells were bound) and T cells (~20% of total T cells were bound) (see FIG. 13C, inset). For both monocytes and lymphocytes, the effects were specific to D1 and were not seen with native AspRS (data not shown). These data support a role for D1 in directly binding and perhaps modulating cells involved in the immune response.

Example 16

D1 Signals Through Nuclear Factor-kB (NF-κB)

Nuclear factor-kB (NF-kB) is a transcription factor thought to play an important role in onset of inflammation through stimulating transcription of pro-inflammatory cytokines (like TNF-α) and, during the resolution of inflammation, to then stimulate expression of anti-inflammatory cytokines like IL-10. NF-κB also plays a central role in directing cellular responses to many stimuli, including oxidative stress, viral and bacterial pathogens, and inflammatory cytokines. The effects of D1 on the activation of NF-κB in macrophages were therefore investigated.

Figure 14A:
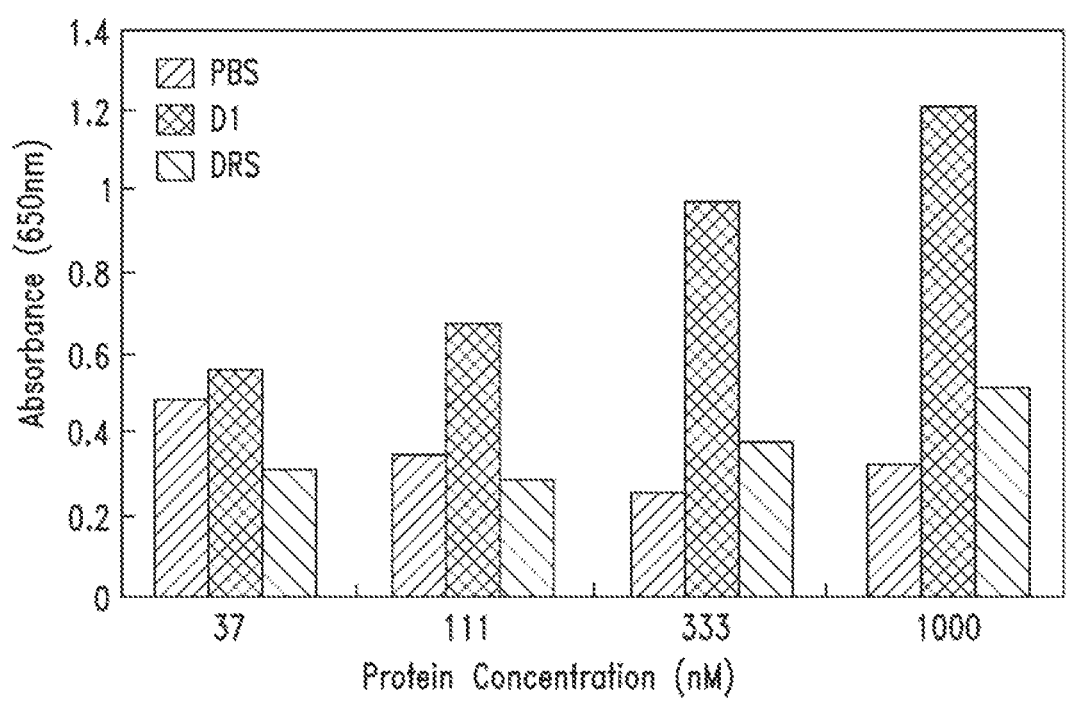
FIGS. 14A-14C show that D1 activates NF-kB via toll-like receptors 2 and 4 (TLR2 and TLR4).

For this experiment, RAW-Blue cells encoding an NF-κB-inducible secreted embryonic alkaline phosphatase reporter gene were incubated with PBS, D1, or full-length AspRS. As shown in FIG. 14A, the treated cells showed a strong dose-dependent activation of NF-κB with D1, as compared to the lack of activation by full-length AspRS or PBS.

Example 17

D1 Binds to and Signals Through TLR2 and TLR4

Figure 14B:
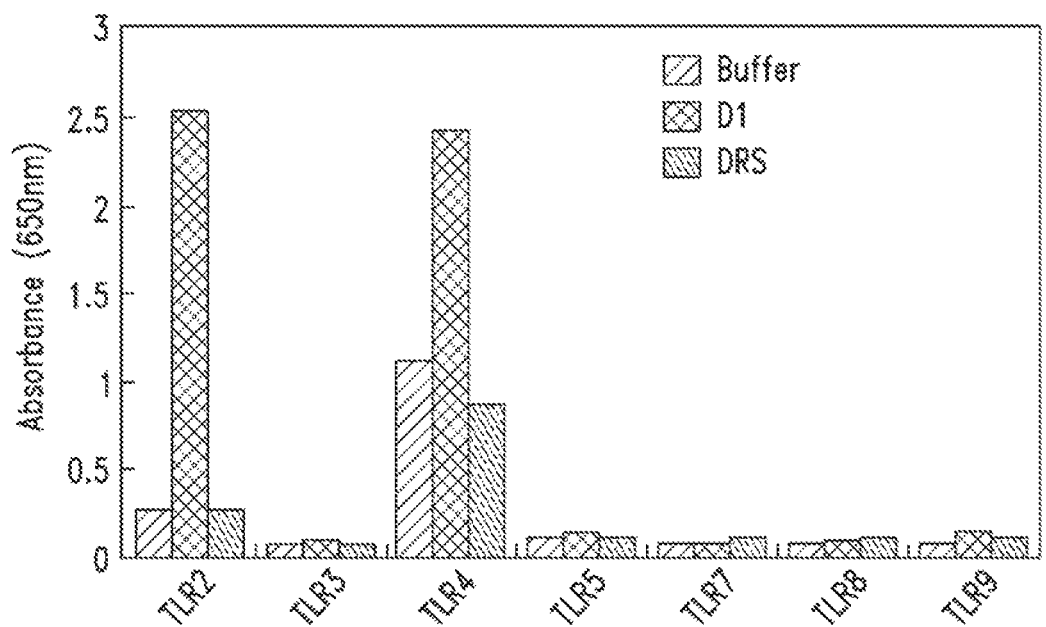

NF-κB can be triggered through a number of macrophage cell surface receptors including the pattern-recognizing toll-like receptors (TLRs). To investigate the potential link to the TLR receptor family, 7 different HEK293 cell lines were stably co-transfected with NF-κB inducible reporter genes (encoding secreted embryonic alkaline phosphatase) and genes encoding a panel of separate toll-like receptors (TLR2, TLR3, TLR4, TLR 5, TLR 7, TLR 8, and TLR9). As shown in FIG. 14B, D1-induced activation of NF-κB was observed only through TLR2 or TLR4 and not TLRs 3, 5, 7, 8, or 9.

Figure 14C:
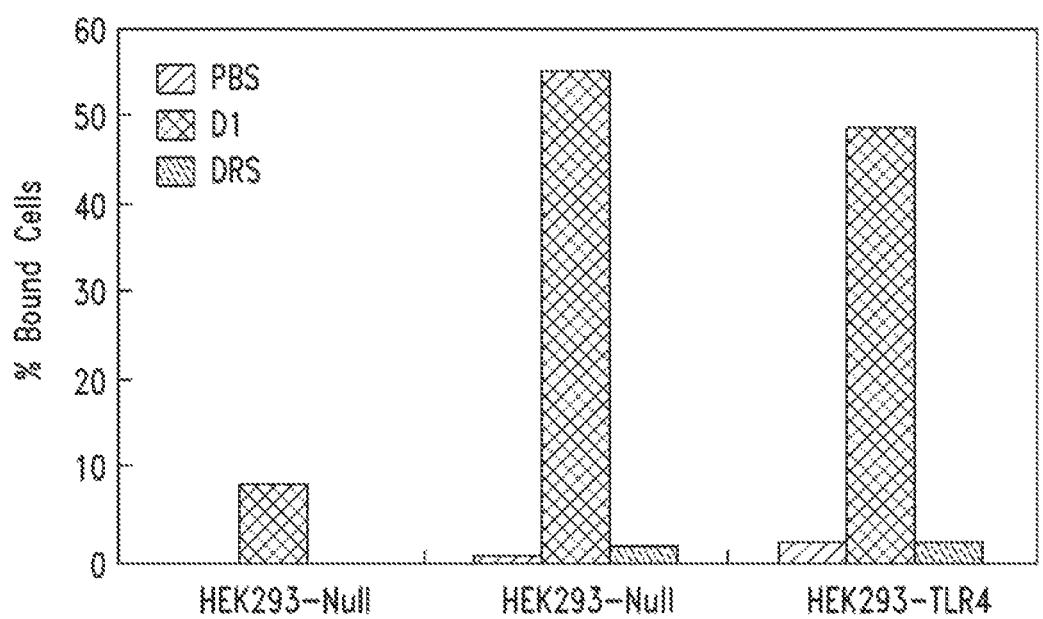

Flow cytometry experiments were utilized to establish whether D2 binds to TLR2 and/or TLR4. In these experiments, V5-tagged D1 (100 nM) or AspRS (100 nM) was incubated with HEK293 cells stably expressing TLR2 or TLR4. Empty vector transfected HEK293 cells served as the null binding control. Binding was assessed by FITC-V5 detection using flow cytometry. FIG. 14C shows that D1 bound strongly to stably transfected HEK cells over-expressing TLR2 or TLR4, but bound much less so to HEK cells that were transfected with vector alone, and which did not express TLR2 or TLR4.

Example 18

The Amphiphilic Helix in D1 Activity

Prior work established LPSs as ligands for TLR2 and 4. Indeed, a lipid A agonist (OM174) ligand for TLR2 and 4 demonstrated similar effects in vivo to what has been observed for D1, namely, transient release of TNF-α (1-2 hours) and subsequent increases in IL-10 secretion. D1 encodes an EMAP-II-like OB-fold. Like D1, the EMAP-II domain, when released by proteolytic cleavage from p43, stimulates secretion of TNF-α from monocytes. The EMAP-II domain also shows additional activity on neutrophils (stimulating migration and secretion of myeloperoxidase). D1, however, did not act on neutrophils (data not shown). One distinction between EMAP-II and D1 is the unique amphiphilic helix contained within the first 22 amino acids of D1. The role of the amphiphilic helix in D1 activity was therefore investigated.

Figures 15A, 15B:
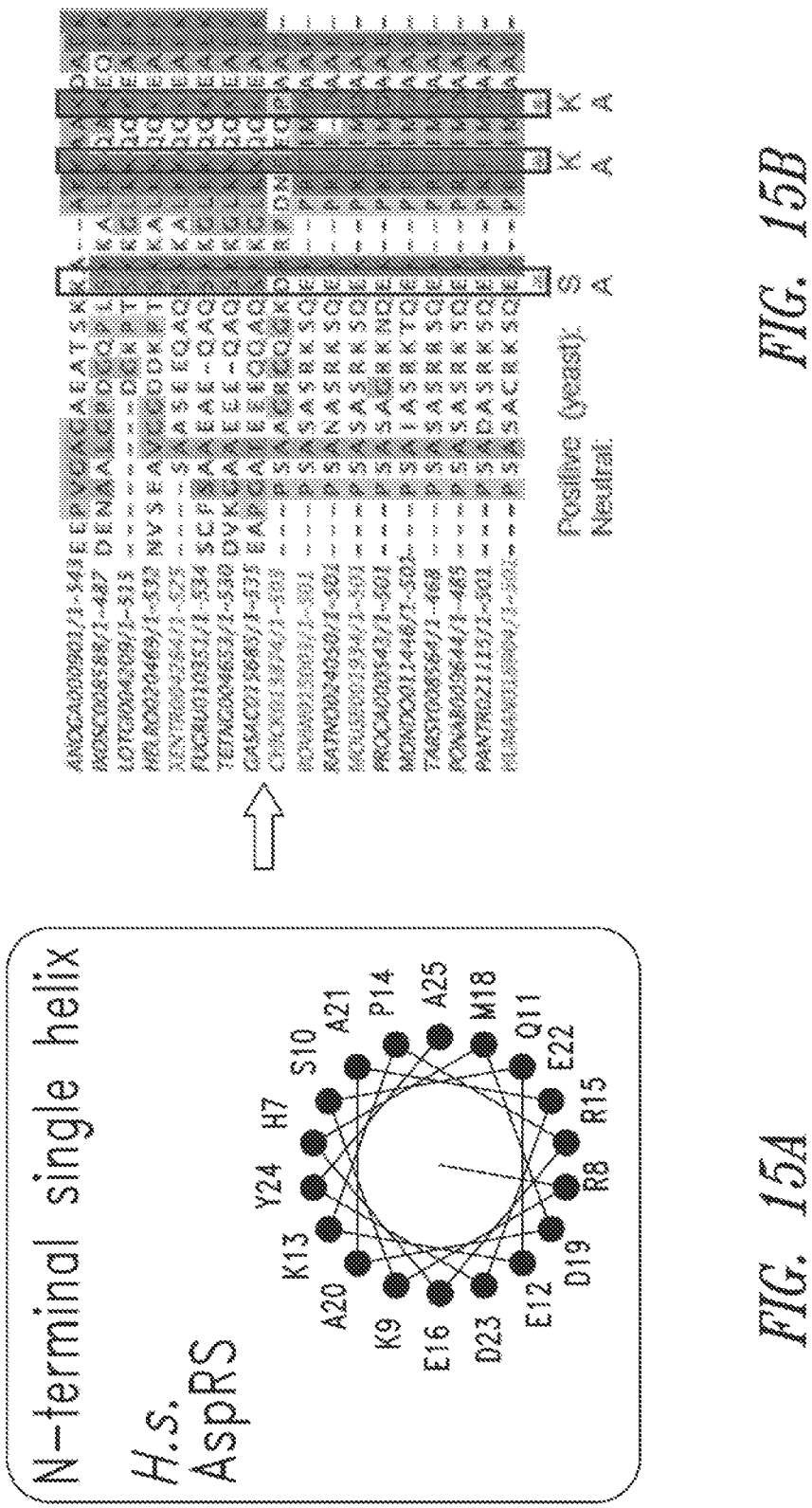
FIGS. 15A-15D show a characterization of D1 activity, relating in part to the N-terminal amphiphilic helix. The helical wheel in FIG. 15A depicts the N-terminus of human AspRS, and reveals an amphiphilic helix. The alignment in FIG. 15B (SEQ ID NOS:6-23, from top to bottom) illustrates two D1 mutants that were designed in view of the N-terminal helix; a triple alanine (AAA) mutation to neutralize the negatively charged residues, and a partial charge reversal mutant (SKK) that represents the yeast sequence.

Initially, the entire amphiphilic helix region of 22 amino acids was deleted from D1 to give Δ22 D1. Certain point mutations were also generated. For instance, as an amphiphilic helix, the human D1 N-terminal helix contains positively charged residues on one side of the helix and negatively charged residues on the other. D1 of lower eukaryotes has a slightly longer helix that is positively charged on both sides. The positively charged residues of this helix have been demonstrated to strengthen tRNA binding, with the consensus sequence LSKKXLKKXXK (SEQ ID NO:6) being particularly important. The evolution of this helix from a positively charged to an amphiphilic helix (through the progression from lower to higher eukaryotic AspRSs) occurs via a concerted switch of 3 highly conserved residues to create a cluster of negative charges on one side of the helix that is strictly conserved in higher eukaryotes (FIGS. 4A and B). It was hypothesized that these negatively charged residues in particular, when in the context of the EMAP-II-like OB-fold, may be contribute to the activity of the novel 22-amino acid helix that is appended to D1. To explore this possibility, substitutions were made at the 3 conserved residues of the negatively charged higher eukaryotic cluster (E12, E16, D19) (see FIG. 15B) to switch them back to the lower eukaryotic form (E12S, E16K, D19K) with its positively charged cluster (SKK D1).

Figure 15C:
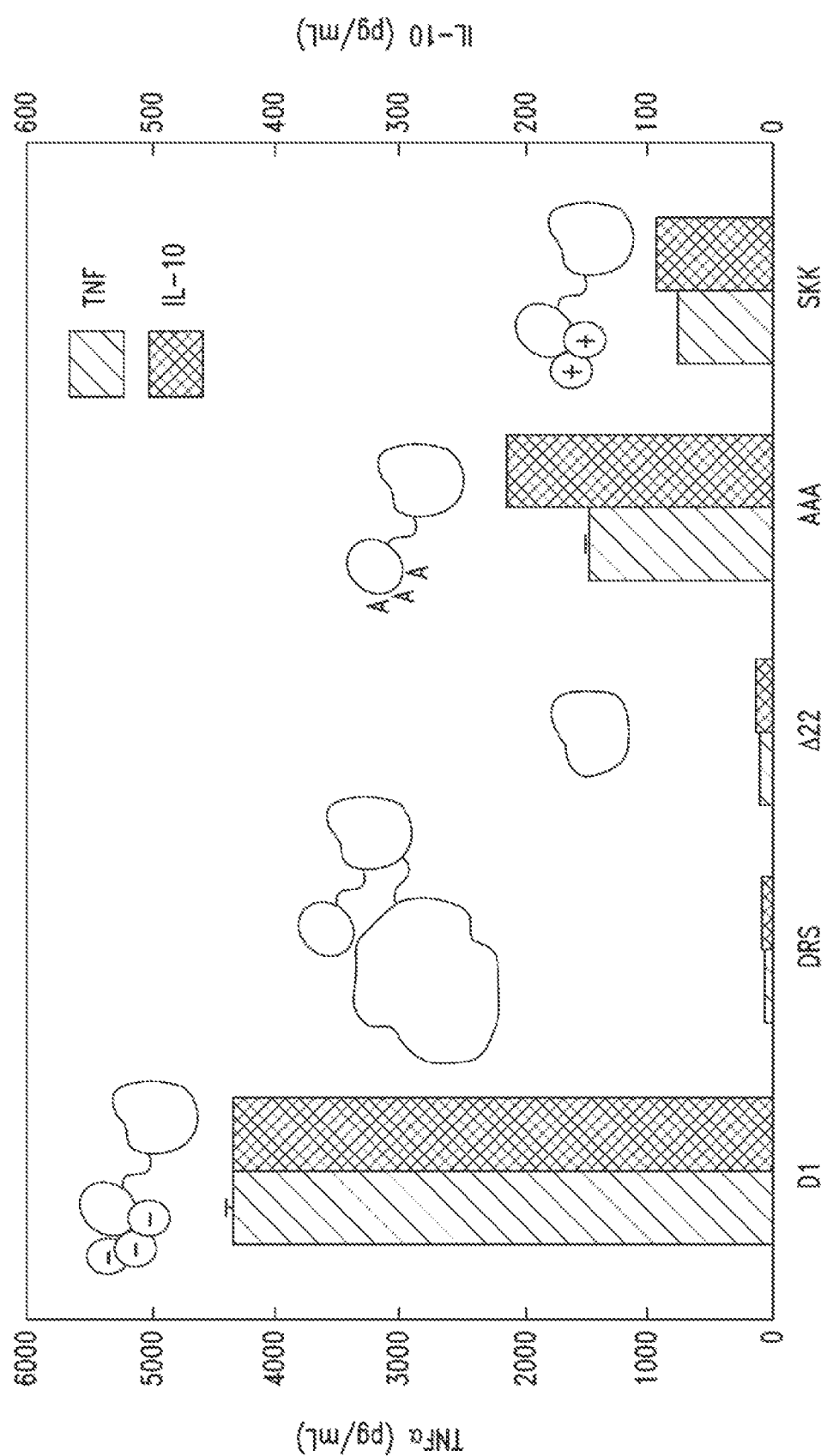
Figure 15D:
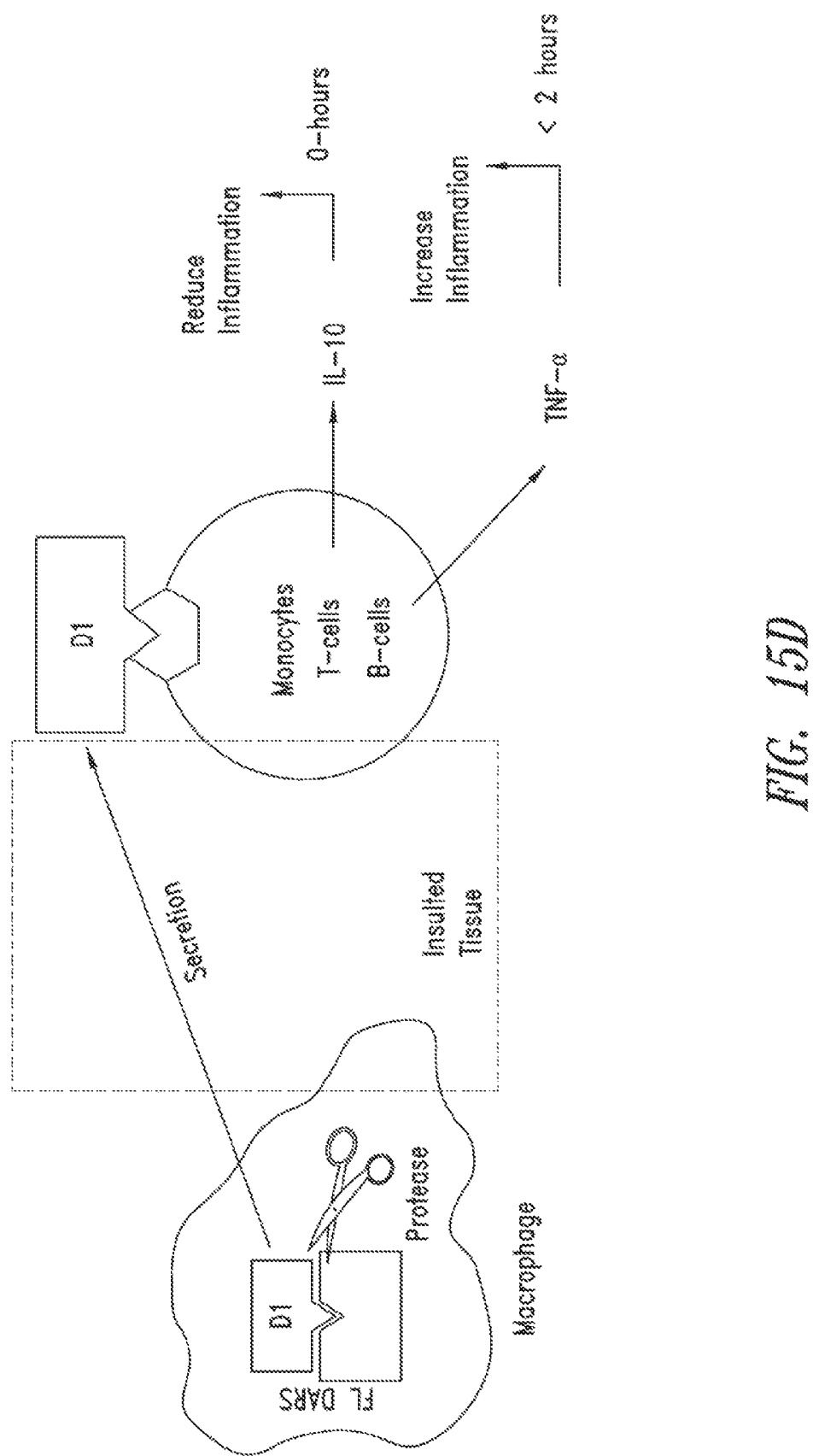

PBMCs were then treated with 50 nm D1, full-length AspRS, the Δ22 mutant, and charge mutants AAA and SKK. Compared to intact D1, Δ22 D1 induced very little TNF-α or IL-10 release from PBMCs (see FIG. 15C). The AAK and SKK D1 mutants also had reduced (~4-fold for SKK) activity for both TNF-α and IL-10 secretion, as compared to D1. These observations suggest a role for the N-terminal amphiphilic helix in receptor binding.

In further support of this conclusion, an N-V5-D1, with the V5-tag at the N-rather than the C-terminus, was also constructed and tested in both TNF-α release and binding assays. The N-V5-D1 was unable to bind or induce TNF-α secretion from PBMCs (data not shown). Thus, the activity of D1 can be reduced with a peptide fusion at the N-terminus, further supporting the role of the N-terminal amphiphilic region in D1 activity.

Example 19

D1 Activity is not Due to Endotoxin Contamination

The recombinant D1 used in these studies was purified from *E. coli* and shown to have an LPS-containing bacterial endotoxin level of less than 12 EU/mg. Nonetheless, LPS is a strong stimulant of TLR2 and TLR4 signaling, and experiments were performed to remove any possibility of trace endotoxin being responsible for the results seen with D1. For this purpose, a gene encoding D1 with a secretion sequence was expressed in transfected HEK293 cells. Conditioned media containing secreted D1 was collected, concentrated, and incubated with PBMCs.

Figure 16A:
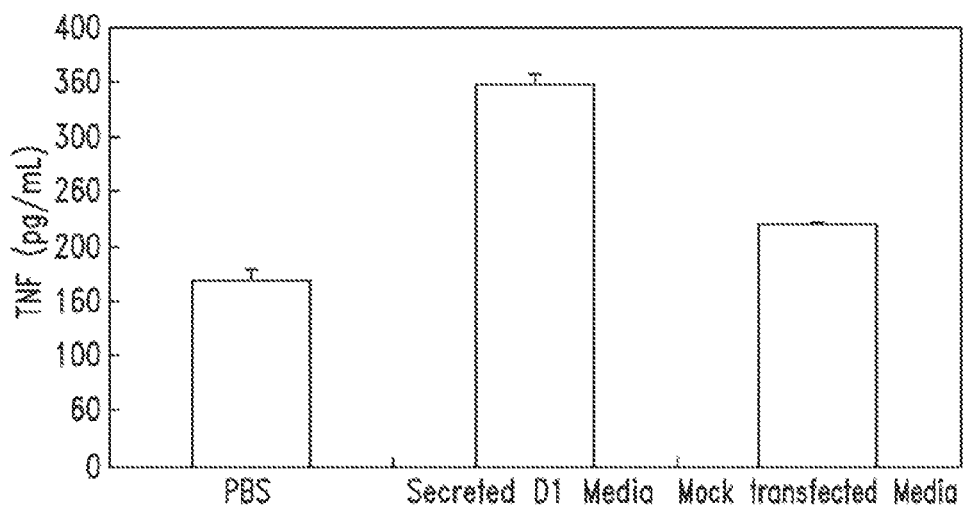
FIGS. 16A-16C show that D1 activity is not due to endotoxin contamination.
Figure 16B:
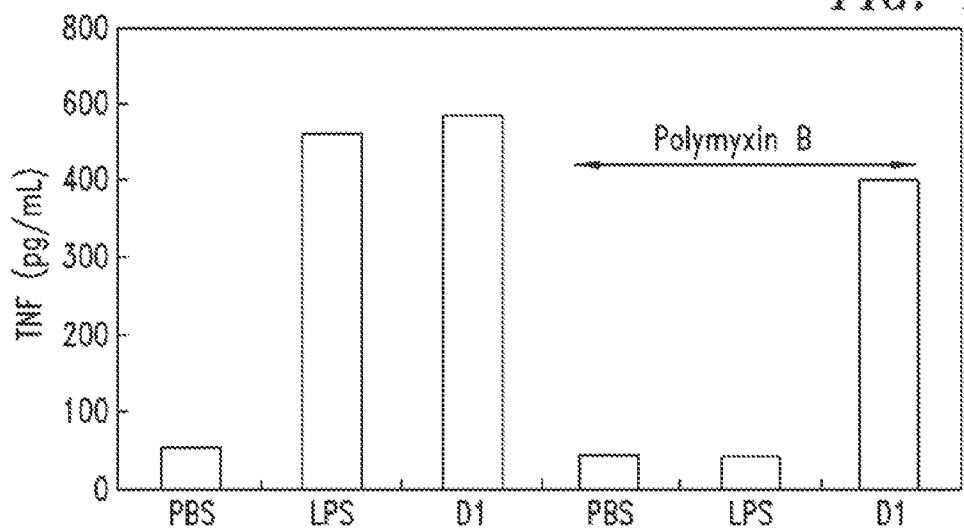
Figure 16C:
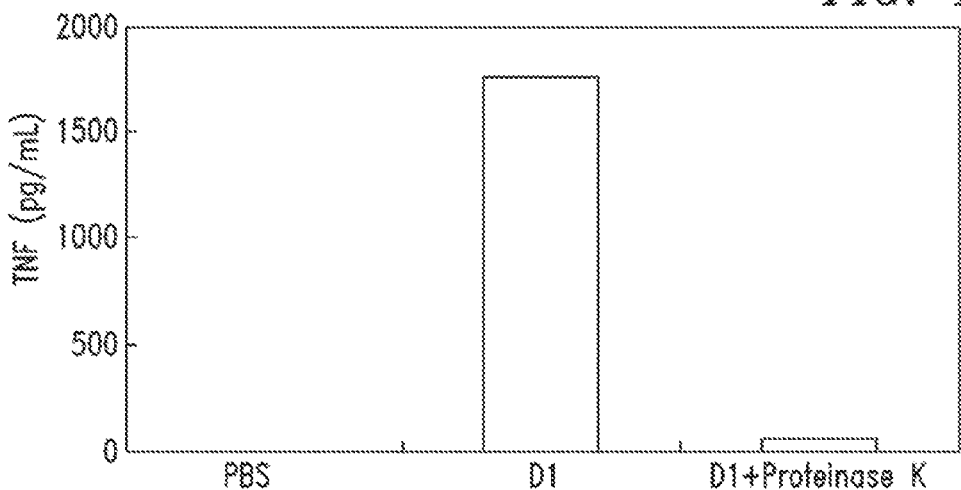

As shown in FIG. 16A, these media stimulated secretion of TNF-α, while media from cells transfected with vector alone did not stimulate secretion. Further, D1-stimulated TNF-α release was unaffected by polymyxin B, a known inactivator of endotoxin (see FIG. 16B). In contrast, as also shown in FIG. 16B, LPS-stimulated activation of secretion of TNF-α was completely blocked by polymyxin B. As shown in FIG. 16C, D1 treated with proteinase K, which completely digests proteins but not endotoxin, resulted in complete abrogation of TNF-α activity in PBMCs. D1 activity is therefore not due to endotoxin contamination.

Example 20

Δ22 AspRS In Vivo Mouse Knock-in Experiments

Because the Δ22 variant of AspRS does not stimulate TNF-α secretion through TLR2 and TLR4, as shown above, the generation of a Δ22 AspRS knock-in mouse allows examination of the physiological effects of the N-terminus of AspRS without compromising the canonical and essential aminoacylation activity of AspRS. Initial experiments focus one examining the potential protective effects of removal of the Δ22 region of AspRS, which has been shown to contribute to AspRS activity as a TLR2 and TLR4 endogenous ligand.

An endotoxic shock experiment is performed to test whether mice with a Δ22 AspRS knock-in are more resistant to endotoxic shock because of their lack of an endogenous ligand for TLR2 and TLR4. In this experiment, wild-type and Δ22 AspRS knock-in mice are injected intraperitoneally with LPS (1 μg/mouse) in combination with D-GalN (20 mg) in a saline solution of 200 μL per dose. This is a commonly used model for endotoxic shock or sepsis that results in near complete lethality in wild-type mice (see Car et al., *J Exp Med*, 179:1437-44, 1994). It is believed that by removing an endogenous pro-inflammatory toll-like receptor ligand (i.e., the AspRS region represented by Δ22) the mice should be resistant to endotoxic shock induced lethality.

An LPS tolerance experiment is performed to test whether macrophages from Δ22 AspRS mice are less tolerant to LPS stimulation due to the lack of a desensitization of toll-like receptor signaling. Macrophages from these knock-in mice should not have been exposed to the pro-inflammatory effects of an endogenous TLR2 & TLR4 ligand (i.e., the AspRS region represented by Δ22). To examine this possibility, wild-type and Δ22 AspRS knock-in mouse peritoneal macrophages are stimulated ex vivo with LPS (100 ng/mL) for 24 hrs, which results in an activation and production of cytokines that can be analyzed by ELISA (see Sato et al., *J Immunol*. 165:7096-101, 2000). Macrophages from the Δ22 AspRS mice should demonstrate a stronger response to LPS due to the lack of a pro-inflammatory signal that otherwise contributes to the induction of tolerance.

As noted, the disclosure above is descriptive, illustrative and exemplary and is not to be taken as limiting the scope defined by the appended claims which follow.

---

The invention claimed is:

1. A pharmaceutical composition, comprising a physiologically-acceptable carrier and an aspartyl-tRNA synthetase (AspRS) polypeptide of up to 200 amino acids in length that comprises (a) an amino acid sequence that is at least 95% identical to residues 1-154, 1-171, or 1-174 of SEQ ID NO:1, or (b) an active fragment of (a) which is 140 or more contiguous amino acids of (a), wherein the AspRS polypeptide or active fragment thereof comprises an OB-fold domain and an amphiphilic helix, wherein the polypeptide has a non-canonical activity selected from induction of IL-10 and binding to TLR2, TLR4, or both, and wherein the composition has an LPS-containing bacterial endotoxin level of less than about 12 EU/mg.

2. The pharmaceutical composition of claim 1, wherein the AspRS polypeptide consists of an amino acid sequence that is at least 98% identical to residues 1-154, 1-171, or 1-174 of SEQ ID NO:1.

3. The pharmaceutical composition of claim 1, wherein the AspRS polypeptide consists essentially of amino acid residues 1-154, 1-171, or 1-174 of SEQ ID NO:1.

4. The pharmaceutical composition of claim 3, wherein the AspRS polypeptide consists essentially of amino acid residues 1-154 of SEQ ID NO:1.

5. The pharmaceutical composition of claim 1, wherein the AspRS polypeptide is modified by pegylation.

6. The pharmaceutical composition of claim 1, wherein the AspRS polypeptide is fused to a heterologous fusion partner.

7. The pharmaceutical composition of claim 6, wherein the heterologous fusion partner comprises an Fc fragment.

8. The pharmaceutical composition of claim 1, wherein the composition is formulated for oral, parenteral, intravenous, intranasal, inhalation, aerosol, intracranial, or intramuscular administration.

9. A method of treating an inflammatory or autoimmune disease in a subject in need thereof, comprising administering to the subject a pharmaceutical composition of claim 1.

* * * * *